US012039584B2

(12) United States Patent
Ketchel, III

(10) Patent No.: US 12,039,584 B2
(45) Date of Patent: *Jul. 16, 2024

(54) SELECTIVELY REDEEMABLE TELEHEALTH SERVICES

(71) Applicant: MDSAVE SHARED SERVICES INC., Brentwood, TN (US)

(72) Inventor: Paul J. Ketchel, III, Brentwood, TN (US)

(73) Assignee: MDSAVE SHARED SERVICES INC., Brentwood, TN (US)

( * ) Notice: Subject to any disclaimer, the term of this patent is extended or adjusted under 35 U.S.C. 154(b) by 147 days.

This patent is subject to a terminal disclaimer.

(21) Appl. No.: 17/984,304

(22) Filed: Nov. 10, 2022

(65) Prior Publication Data

US 2023/0097995 A1 Mar. 30, 2023

Related U.S. Application Data

(63) Continuation of application No. 17/938,931, filed on Sep. 6, 2022, which is a continuation of application
(Continued)

(51) Int. Cl.
*G06Q 40/00* (2023.01)
*G06Q 30/0601* (2023.01)
(Continued)

(52) U.S. Cl.
CPC ....... *G06Q 30/0621* (2013.01); *G06Q 20/065* (2013.01); *G06Q 20/10* (2013.01);
(Continued)

(58) Field of Classification Search
CPC .... G06Q 40/00; G06Q 30/0621; G06Q 20/65; G06Q 20/10; G06Q 20/381;
(Continued)

(56) References Cited

U.S. PATENT DOCUMENTS 7,034,691 B1 4/2006 Rapaport
7,895,061 B2 2/2011 Schoenberg
(Continued)

FOREIGN PATENT DOCUMENTS

CA 2447731 4/2005
CA 3088562 11/2020
(Continued)

OTHER PUBLICATIONS

The strategy that will fix health care ME Porter, TH Lee—Harvard business review, 2013—aerodigestive.us (Year: 2013).*
(Continued)

*Primary Examiner* — Lalita M Hamilton
(74) *Attorney, Agent, or Firm* — Morrison & Foerster LLP

(57) ABSTRACT

The invention relates to receiving a selection of a bundled set of healthcare services comprising at least one selectively redeemable healthcare service, the bundled set to be provided by a plurality of providers; generating an electronic health record comprising a purchase data record identified by and with a unique confirmation number; presetting an initial individual redemption status in the purchase data record for each selectively redeemable healthcare service of the bundled set of healthcare services as unredeemed; and providing a user access to the purchase data record to receive each selectively redeemable healthcare service. A service may be provided via an in-person visit. A service may be provided at a patient location remote from a provider location, via a telehealth visit. The telehealth visit may result in a prescription or referral for additional services such as imaging, using patient medical data updated based on symptom assessment during the telehealth visit.

27 Claims, 20 Drawing Sheets

Related U.S. Application Data

No. 17/543,723, filed on Dec. 6, 2021, now Pat. No. 11,475,498, which is a continuation-in-part of application No. 17/411,494, filed on Aug. 25, 2021, now Pat. No. 11,315,160, which is a continuation of application No. 17/209,117, filed on Mar. 22, 2021, now Pat. No. 11,170,423, which is a continuation of application No. 16/913,662, filed on Jun. 26, 2020, now Pat. No. 10,991,021, which is a continuation-in-part of application No. 16/685,888, filed on Nov. 15, 2019, now Pat. No. 11,030,666, which is a continuation-in-part of application No. 16/520,906, filed on Jul. 24, 2019, now Pat. No. 11,030,665, which is a continuation-in-part of application No. 15/055,076, filed on Feb. 26, 2016, now abandoned, which is a continuation-in-part of application No. 14/874,004, filed on Oct. 2, 2015, now abandoned, which is a continuation of application No. 14/827,026, filed on Aug. 14, 2015, now abandoned, which is a continuation-in-part of application No. 14/461,209, filed on Aug. 15, 2014, now Pat. No. 9,123,072.

(60) Provisional application No. 61/866,922, filed on Aug. 16, 2013.

(51) Int. Cl.
  *G06Q 50/22* (2018.01)
  *G06Q 30/0201* (2023.01)
  *G06Q 30/0207* (2023.01)
  *G06Q 20/06* (2012.01)
  *G06Q 20/10* (2012.01)
  *G06Q 20/38* (2012.01)
  *G16H 40/20* (2018.01)
  *G16H 10/60* (2018.01)
  *G16H 20/00* (2018.01)

(52) U.S. Cl.
  CPC ....... *G06Q 20/381* (2013.01); *G06Q 30/0206* (2013.01); *G06Q 30/0239* (2013.01); *G06Q 30/0613* (2013.01); *G06Q 30/0629* (2013.01); *G06Q 30/0633* (2013.01); *G06Q 50/22* (2013.01); *G16H 10/60* (2018.01); *G16H 40/20* (2018.01); *G16H 20/00* (2018.01)

(58) Field of Classification Search
  CPC ........... G06Q 30/0206; G06Q 30/0239; G06Q 30/0613; G06Q 30/0629; G06Q 30/0633; G06Q 50/22; G06N 40/20; G06N 20/00; G06H 10/60
  See application file for complete search history.

(56) References Cited

U.S. PATENT DOCUMENTS

| | | | |
|---|---|---|---|
| 8,428,964 | B2 | 4/2013 | Picken |
| 8,494,881 | B1 | 7/2013 | Wizig |
| 8,612,267 | B1 | 12/2013 | Shrivastava |
| 9,123,072 | B2 | 9/2015 | Ketchel, III |
| 10,373,158 | B1 | 8/2019 | James et al. |
| 10,600,050 | B1 | 3/2020 | Anton et al. |
| 10,708,042 | B1 | 7/2020 | Rubenstein et al. |
| 10,991,021 | B2 | 4/2021 | Ketchel, III et al. |
| 11,012,429 | B2 | 5/2021 | Dhanabalan et al. |
| 2002/0004782 | A1 | 1/2002 | Cincotta |
| 2002/0059082 | A1 | 5/2002 | Moczygemba |
| 2002/0065758 | A1 | 5/2002 | Henley |
| 2002/0103672 | A1 | 8/2002 | Torres et al. |
| 2003/0009402 | A1 | 1/2003 | Mullen |
| 2003/0018530 | A1 | 1/2003 | Walker et al. |
| 2005/0010440 | A1 | 1/2005 | Merkin |
| 2005/0021455 | A1 | 1/2005 | Webster |
| 2005/0075975 | A1 | 4/2005 | Rosner |
| 2007/0043595 | A1 | 2/2007 | Pederson |
| 2007/0088580 | A1 | 4/2007 | Richards, Jr. |
| 2007/0150986 | A1 | 6/2007 | Jung |
| 2008/0021827 | A1 | 1/2008 | Willis |
| 2009/0144088 | A1 | 6/2009 | Zubiller |
| 2009/0210251 | A1 | 8/2009 | Callas |
| 2010/0070295 | A1 | 3/2010 | Kharraz Tavakol et al. |
| 2010/0121727 | A1 | 5/2010 | Butler |
| 2010/0250271 | A1 | 9/2010 | Pearce et al. |
| 2010/0306013 | A1 | 12/2010 | Mark |
| 2011/0106593 | A1 | 5/2011 | Schoenberg |
| 2011/0145149 | A1 | 6/2011 | Valdes |
| 2012/0053963 | A1 | 3/2012 | Seymour |
| 2012/0054119 | A1 | 3/2012 | Zecchini |
| 2012/0215563 | A1 | 8/2012 | Lassen et al. |
| 2012/0232936 | A1 | 9/2012 | Bravata et al. |
| 2012/0239560 | A1 | 9/2012 | Pourfallah et al. |
| 2012/0245953 | A1 | 9/2012 | Morris |
| 2013/0096937 | A1 | 4/2013 | Campbell et al. |
| 2013/0179194 | A1 | 7/2013 | Lorsch |
| 2013/0198025 | A1 | 8/2013 | Picken |
| 2014/0067406 | A1 | 3/2014 | Hyatt et al. |
| 2014/0149135 | A1 | 5/2014 | Boerger et al. |
| 2014/0195370 | A1 | 7/2014 | Devasia |
| 2014/0365240 | A1 | 12/2014 | Canton |
| 2015/0052009 | A1 | 2/2015 | Ketchell, III |
| 2015/0178808 | A1 | 6/2015 | Grossman et al. |
| 2015/0250271 | A1 | 9/2015 | Ogilvie |
| 2015/0294338 | A1 | 10/2015 | Ketchel, III et al. |
| 2015/0332283 | A1 | 11/2015 | Witchey |
| 2015/0356663 | A1 | 12/2015 | Ketchel, III et al. |
| 2016/0027085 | A1 | 1/2016 | Ketchel, III et al. |
| 2016/0071225 | A1 | 3/2016 | Chmait |
| 2016/0253731 | A1 | 9/2016 | Ketchel, III et al. |
| 2018/0240191 | A1 | 8/2018 | Aronson |
| 2019/0266597 | A1 | 8/2019 | Mohtar |
| 2019/0333033 | A1 | 10/2019 | Finlow-Bates |
| 2019/0340946 | A1 | 11/2019 | Elmessiry et al. |
| 2019/0378121 | A1 | 12/2019 | Marshall |
| 2019/0378227 | A1 | 12/2019 | Vanzetta |
| 2020/0076884 | A1 | 3/2020 | Li et al. |
| 2020/0111092 | A1 | 4/2020 | Wood et al. |
| 2020/0134612 | A1 | 4/2020 | Fostiropulo et al. |
| 2020/0167871 | A1 | 5/2020 | Basu |
| 2020/0175506 | A1 | 6/2020 | Snow |
| 2020/0193764 | A1 | 6/2020 | Ovalle |
| 2020/0219089 | A1 | 7/2020 | Crumb et al. |
| 2020/0294038 | A1 | 9/2020 | Kreiser et al. |
| 2020/0304518 | A1 | 9/2020 | Thekadath et al. |
| 2020/0334727 | A1 | 10/2020 | Ketchel, III et al. |
| 2021/0065267 | A1 | 3/2021 | Smith |
| 2021/0082044 | A1 | 3/2021 | Sliwka et al. |
| 2021/0097484 | A1 | 4/2021 | Ramos et al. |
| 2021/0099313 | A1 | 4/2021 | Kondrashov et al. |
| 2021/0124722 | A1 | 4/2021 | Srivastava |
| 2021/0133735 | A1 | 5/2021 | Maim |
| 2021/0150653 | A1 | 5/2021 | Hjertstedt |
| 2021/0158441 | A1 | 5/2021 | Cella |
| 2021/0326939 | A1 | 10/2021 | Navar |

FOREIGN PATENT DOCUMENTS

| | | | | |
|---|---|---|---|---|
| CA | 3088562 A1 | * | 11/2020 | ........... G06Q 20/208 |
| JP | 2003-22409 | | 1/2003 | |
| JP | 2004050619 A | * | 2/2004 | |
| WO | 03/090010 | | 10/2003 | |
| WO | 2018039312 | | 3/2018 | |

OTHER PUBLICATIONS

Proquest, "Medical Instruments & Supplies; MedAssets Addresses Payment Reform with Bundled Reimbursement Solution", Obesity, Fitness & Wellness Week, retrieved from <http://search.proquest.com/docview/732996687?1:Accountid=14753>, Aug. 7, 2010, 2 pages.

(56) References Cited

OTHER PUBLICATIONS

International Search Report and Written Opinion received for PCT Patent Application No. PCT/US2015/037751, dated Sep. 17, 2015, 15 pages.
Extended European Search Report received for European Patent Application No. 14836898.8, dated Dec. 22, 2016, 9 pages.
Office Action (Communication pursuant to Article 94(3) EPC) received for EP Patent Application No. 14836898.8, dated Oct. 31, 2017, 10 pages.
Miller, Julie. Nimble Payment Models; Managed Healthcare Executive; Monmouth Junction vol. 20, Iss. 4, (Apr. 2010): 12-16. (Year: 2010).
Credit Management Tools.com: Credit Tools: Discount and Prepayment, 2009, pp. 1-3 (Year: 2009).
International Search Report and Written Opinion received for PCT Patent Application No. PCT/US2021/025022, dated Jun. 28, 2021.
When Does Prepaying Expenses Accelerate Tax Deductions? Zimmerman, John C, CPA. Practical Tax Strategies; Boston vol. 79, Iss. 5, (Nov. 2007): 260-262,264-266. (Year: 2007.

\* cited by examiner

Pre-Paid Medical Voucher
Confirmation Number: 979110096
408 → Voucher Number: 17605096
Order Date: 08/15/2013

Patient Information — 402

| Name | DOB | Phone Number | Email address |
|---|---|---|---|
| Sarah Doe | 08/23/1989 | 619-915-8150 | sample@sample.com — 404 |

Purchase Information — 406

| Procedure | Provider | Phone Number |
|---|---|---|
| 29877 - Surgical arthroscopy of knee with chodroplasty (1) | John Smith | 1-877-461-2491 |
| 1382 Anesthesia for diagnostic arthroscopic procedure on knee (1) | David Jackson | 1-877-461-2491 |
| Facility Fee | Brentwood Surgery Center | 615-915-9330 |
| Total Pre-Paid Price: $1554.1 | | |

410 → How to use your MDSave Medical Voucher:
You have three different options to present this voucher to the receptionist at the time of your appointment.
1. Pull up your MDSave email receipt on your smart phone.
2. Write down the Confirmation Number and the Voucher Number.
3. Or Simply print this page and take the copy with you.

FIG. 4B 700  702

RADIOLOGY

PAYOUT RATES LISTED ARE SUGGESTED RATES ONLY. ALL RATES ARE TO BE DETERMINED BY THE HOSPITAL SYSTEM

| SPECIFIC LOCALITY | 704c | 704d | | RECOMMENDED RATE | |
|---|---|---|---|---|---|
| FACILITY | ABILENE MEDICAL CENTER | 0.773 | | FACILITY | 130% |
| PHYSICIAN | REST OF TEXAS | 0.97 | | PHYSICIAN | 130% |

704a  704b  704  706b  706a

ADVANCED

☐ SELECT MDSAVE RADIOLOGY GROUP PRICING    713    ✓EXPAND ALL ▲COLLAPSE ALL ☐ EXPORT TO EXCEL

| PROCEDURE | REC. FACILITY PRICE | REC. PHYS. PRICE | MDSAVE FEE | TOTAL AMOUNT |
|---|---|---|---|---|
| BONE DENSIOMETRY | 711 | 712 | 714 | 715 |
| ✓ BONE DENSITY DXA EXTREMITY | $66.68 | $12.60 | $12.00 | $91.28 |
| DESCRIPTION  CPT CODE | CMS FACILITY | CMS PHYSICIAN | FACILITY REC. RATE 130% | PHYSICIAN REC. RATE 130% |
| DXA BONE DENSITY/PERIPHERAL  77081 | $59.37 | $11.08 | $66.68 | $13.97 |
| FRACTURE ASSESSMENT VIA DXA  77085 | $59.37 | $9.90 | $66.69 | $11.22 |
| AVERAGES $ | | | 66.68 | 12.60 |
| | | | 711b | 711a  708 |
| > BONE DENSITY DXA SCAN | $103.99 | $16.24 | $12.00 | $132.23 |
| FLUOROSCOPY | | | | |
| > VIDEOFLUOROSCOPIC SWALLOWING STUDY | $114.21 | $126.69 | $60.00 | $300.90 |
| > BARIUM ENEMA WITH AIR | $169.58 | $64.02 | $60.00 | $293.60 |
| > BARIUM SWALLOW | $114.21 | $29.76 | $60.00 | $203.97 |
| > CYSCOGRAM (VCYG) | $297.90 | $78.45 | $60.00 | $436.35 |
| > FISTULOGRAM | $378.52 | $33.82 | $60.00 | $472.04 |
| > HYSTEROSALPINGOGRAM (HSG) TEST | $378.52 | $99.64 | $60.00 | $538.16 |
| > BARIUM ENEMA | $169.58 | $44.64 | $60.00 | $274.22 |
| RADIOLOGY (X-RAY) | | | | |
| > X-RAY | $64.41 | $13.20 | $12.00 | $89.61 |
| > COMPLEX X-RAY | $102.08 | $18.49 | $12.00 | $132.57 |
| CT | | | | |
| > CT SCAN WITH CONTRAST | $279.65 | $79.66 | $60.00 | $419.31 |
| > CT SCAN WITH & WITHOUT CONTRAST | $314.92 | $84.62 | $60.00 | $459.54 |
| > CT SCAN WITHOUT CONTRAST | $142.04 | $69.15 | $60.00 | $271.19 |
| > CT SCAN OF ABDOMEN & PELVIS WITHOUT CONTRAST | $271.55 | $112.03 | $60.00 | $443.58 |
| > CT SCAN WITH MYELOGRAM | $689.90 | $59.05 | $60.00 | $808.95 |
| > CT SCAN OF ABDOMEN & PELVIS WITH AND WITHOUT CONTRAST | $438.15 | $129.19 | $60.00 | $627.34 |
| > CT SCAN OF ABDOMEN & PELVIS WITH CONTRAST | $438.15 | $117.00 | $60.00 | $615.15 |
| CTA | | | | |
| > CT ANGIOGRAPHY CARDIAC ASSESSMENT | $249.34 | $134.38 | $60.00 | $443.72 |
| > CT CORONARY ANGIOGRAPHY | $249.34 | $150.42 | $60.00 | $459.76 |
| > CT ANGIOGRAPHY WITH AND WITHOUT CONTRAST | $327.90 | $117.45 | $60.00 | $605.35 |

[EMAIL PRICES] [SAVE CHANGES] [TAKE LIVE]
710a  710b  710c

| GENERAL SURGERY ▾ |
PAYOUT RATES LISTED ARE SUGGESTED RATES ONLY. ALL RATES ARE TO BE DETERMINED BY THE HOSPITAL SYSTEM.

SPECIFIC LOCALITY    704e    704f    706c    RECOMMENDED RATE

| | | | | | |
|---|---|---|---|---|---|
| ANESTHESIA | NATIONAL RATE | 1 | ANESTHESIA | 100% | |
| FACILITY | ABILENE MEDICAL CENTER | 0.773 | FACILITY | 130% | |
| PHYSICIAN | REST OF TEXAS | 0.97 | PHYSICIAN | 130% | |

716

☐ ANESTHESIS    ˅EXPAND ALL   ˄COLLAPSE ALL   ☐ EXPORT TO EXCEL   ADVANCED

| PROCEDURE | REC. FACILITY PRICE | REC. PHYS. PRICE | REC. ANESTHESIA PRICE | MDSAVE FEE | TOTAL AMOUNT |
|---|---|---|---|---|---|
| GENERAL SURGERY | | | | | |
| › COLONOSCOPY | $877.68 | $334.01 | $250.00 | $125.00 | $1,586.70 |
| ˅ INGUINAL HERNIA REPAIR | $3,004.76 | $787.49 | $250.00 | $125.00 | $4,167.25 |

| DESCRIPTION | CPT CODE | CMS FACILITY | CMS PHYSICIAN | CMS ANESTHESIA | FACILITY REC. RATE 130% | PHYSICIAN REC. RATE 130% | ANESTHESIA REC. RATE 130% |
|---|---|---|---|---|---|---|---|
| REPAIR INGUINA HERNIA, SLIDING ANY AGE | 49525 | $2,675.43 | $590.67 | $250.00 | $3,004.76 | $744.83 | $250.00 |
| SURGICAL REPAIR OF INGUINAL HERNIA | 49505 | $2,675.43 | $536.68 | $250.00 | $3,004.76 | $676.75 | $250.00 |
| REPAIR RECURRENT INGUINAL HERNIA | 49520 | $2,675.43 | $652.17 | $250.00 | $3,004.76 | $822.39 | $250.00 |
| INCARCERATED OR STRANGULATED | 49521 | $2,675.43 | $739.06 | $250.00 | $3,004.76 | $931.94 | $250.00 |
| INCARCERATED OR STRANGULATED | 49507 | $2,675.43 | $603.90 | $250.00 | $3,004.76 | $761.52 | $250.00 |
| | | | | AVERAGE $ | 3004.76 | 787.49 | 250.00 |

711b    711a    711c

| › LAPAROSCOPIC-ASSISTED VAGINAL HYSTERECTOMY | $6,153.59 | $1,047.82 | $250.00 | $125.00 | $7,576.41 |
|---|---|---|---|---|---|
| › APPENDECTOMY | $2,567.30 | $836.81 | $250.00 | $125.00 | $3,779.11 |
| › HYSTERECTOMY ABLATION | $4,469.00 | $438.69 | $250.00 | $125.00 | $5,282.69 |
| › TOTAL ABDOMINAL HYSTERECTOMY | $0.00 | $1,384.16 | $250.00 | $125.00 | $1,759.16 |
| › UPPER ENDOSCOPY (EGD) | $892.54 | $224.78 | $250.00 | $125.00 | $1,492.32 |
| › VAGINAL HYSTERECTOMY | $4,469.00 | $1,169.70 | $250.00 | $125.00 | $6,013.70 |
| › LAPAROSCOPIC CHOLECYSTECTOMY (LAPAROSCOPIC GALL BLADDER REMOVAL) | $4,244.63 | $1,078.63 | $250.00 | $125.00 | $5,698.26 |
| › LAPAROSCOPIC TUBAL LIGATION | $4,244.63 | $914.81 | $250.00 | $125.00 | $5,534.44 |
| › LAPAROSCOPIC APPENDECTOMY | $4,244.63 | $782.25 | $250.00 | $125.00 | $5,401.88 |

[EMAIL PRICES] [SAVE CHANGES] [TAKE LIVE]

| GI | |

PAYOUT RATES LISTED ARE SUGGESTED RATES ONLY. ALL RATES ARE TO BE DETERMINED BY THE HOSPITAL SYSTEM

SPECIFIC LOCALITY                                          RECOMMENDED RATE

FACILITY   ABILENE MEDICAL CENTER   0.773      FACILITY   130%
PHYSICIAN   REST OF TEXAS   0.97      PHYSICIAN   130%

717                                      ADVANCED

○ ANESTHESIA   ● SEDATION   ☐ PATHOLOGY            ⌄EXPAND ALL   ⌃COLLAPSE ALL   ☐ EXPORT TO EXCEL

| PROCEDURE | REC. FACILITY PRICE | REC. PHYS. PRICE | PATHOLOGY PRICE | MDSAVE FEE | TOTAL AMOUNT |
|---|---|---|---|---|---|
| GI | | | | | |
| > COLONOSCOPY | $577.69 | $334.01 | $130.00 | $125.00 | $1,466.70 |
| > FLEXIBLE SIGMOIDOSCOPY | $704.39 | $143.19 | $130.00 | $125.00 | $1,102.58 |
| ⌄ TRANSNASAL ESOPHAGOSCOPY (TNE) | $837.38 | $119.03 | $0.00 | $125.00 | $1,081.41 |

| DESCRIPTION | CPT CODE | CMS FACILITY | CMS PHYSICIAN | FACILITY REC. RATE 130% | PHYSICIAN REC. RATE 130% | PATHOLOGY REC. RATE |
|---|---|---|---|---|---|---|
| ESOPHAGOSCOPY FLEX DOC BRUSH | 43197 | $745.60 | $85.81 | $837.38 | $108.21 | $0.00 |
| ESOPHAGOSCOPY FLEX TMSN BIOPY | 43198 | $745.60 | $102.97 | $837.38 | $129.03 | $0.00 |
| | | | AVERAGES $ | 837.38 | 119.03 | 0.00 |
| | | | | | $125.00 | 711d |

| PROCEDURE | REC. FACILITY PRICE | REC. PHYS. PRICE | PATHOLOGY PRICE | MDSAVE FEE | TOTAL AMOUNT |
|---|---|---|---|---|---|
| > ESOPHAGEAL MANOMETRY | $369.20 | $91.98 | $0.00 | $125.00 | $586.18 |
| > HEMORRHOID BANDING | $496.98 | $249.32 | $0.00 | $125.00 | $871.30 |
| > BRAVO 48 HOUR PH MONITOR | $369.20 | $107.31 | $0.00 | $125.00 | $601.51 |
| > ABDOMINAL PARACENTESIS | $549.59 | $120.15 | $130.00 | $125.00 | $924.74 |
| > HEMORRHOIDECTOMY | $2,180.41 | $513.44 | $0.00 | $125.00 | $2,818.85 |
| > FEEDING TUBE PLACEMENT | $219.23 | $52.22 | $0.00 | $125.00 | $406.45 |
| > CAPSULE ENDOSCOPY | $957.36 | $246.17 | $0.00 | $125.00 | $1,328.53 |
| > FEEDING TUBE PLACEMENT (PEG) | $1,195.94 | $275.48 | $0.00 | $125.00 | $1,596.42 |
| > UPPER ENDOSCOPY (EGD) | $892.54 | $224.78 | $0.00 | $125.00 | $1,242.32 |
| > EGD WITH COLONOSCOPY | $1,203.96 | $736.42 | $0.00 | $125.00 | $2,065.38 |

[EMAIL PRICES] [SAVE CHANGES] [TAKE LIVE]

FIG. 7C

SELECTIVELY REDEEMABLE TELEHEALTH SERVICES

CROSS REFERENCE TO RELATED APPLICATIONS

This application is a continuation of Ser. No. 17/938,931 filed Sep. 6, 2022, which is a continuation of Ser. No. 17/543,723 filed Dec. 6, 2021, now issued U.S. Pat. No. 11,475,498, which is a continuation-in-part of U.S. application Ser. No. 17/411,494 filed Aug. 25, 2021, now issued U.S. Pat. No. 11,315,160, which is a continuation of U.S. application Ser. No. 17/209,117 filed Mar. 22, 2021, now issued U.S. Pat. No. 11,170,423, which is a continuation of U.S. application Ser. No. 16/913,662 filed Jun. 26, 2020, now issued U.S. Pat. No. 10,991,021, which is a continuation-in-part of U.S. application Ser. No. 16/685,888 filed Nov. 15, 2019, now issued U.S. Pat. No. 11,030,666, which is a continuation-in-part of U.S. application Ser. No. 16/520,906 filed Jul. 24, 2019, now issued U.S. Pat. No. 11,030,665, which is a continuation-in-part of U.S. application Ser. No. 15/055,076 filed Feb. 26, 2016, which is a continuation-in-part of U.S. application Ser. No. 14/874,004 filed Oct. 2, 2015, which is a continuation of U.S. application Ser. No. 14/827,026 filed Aug. 14, 2015, which is a continuation-in-part of U.S. application Ser. No. 14/461,209 filed Aug. 15, 2014, now issued U.S. Pat. No. 9,123,072, which claims the benefit of Provisional Appl. 61/866,922 filed Aug. 16, 2013, the contents of which are all incorporated herein in their entirety by reference thereto. In addition, said U.S. application Ser. No. 15/055,076 filed Feb. 26, 2016, is also a continuation-in-part of U.S. application Ser. No. 14/750,081 filed Jun. 25, 2015, which is a continuation-in-part of U.S. application Ser. No. 14/461,209 filed Aug. 15, 2014, now issued U.S. Pat. No. 9,123,072, which claims the benefit of Provisional Appl. 61/866,922 filed Aug. 16, 2013, the contents of which are all incorporated herein in their entirety by reference thereto.

BACKGROUND OF THE INVENTION

Medical services are services provided to a medical patient. Some medical services may help improve or maintain a patient's health, based on disease prevention, diagnosis, or treatment. The practice of medicine encompasses medical procedures performed for a patient, which may include both preventive care and treatment. Medical service providers include doctors, hospitals, and health insurers. A provider may offer medical services to patients by provisioning medical resources such as, for example, laboratory, imaging, treatment, or surgical facilities, to provide the services. Some medical services may require specially trained or licensed medical professionals. For example, a medical practice providing diagnosis and treatment for joint pain may provide medical services through the work of an orthopedic specialist. In some scenarios, patient access to a specialized professional or facility may be limited by cost, or availability. Some specialized medical professionals and related facilities may be scarce.

A medical practice may also limit the medical procedures offered to patients based on the availability of specialized professionals and facilities at a given time or location as increasingly seen with the onset of the COVID-19 pandemic. For example, the services offered to a patient may be determined based on allocating surgeons to various surgical facility locations at specific times. Services supplied to patients may be limited to the allocated medical professionals and facilities, even when medical service demand exceeds supply at a given location or time. A medical practice providing many types of medical services may expend significant resources adapting the offered services to demand as cost and demand change. Some medical practices may fail to capture potential revenue lost when resources to provide medical services are underutilized relative to medical service demand.

The price of healthcare services varies depending on specialty, procedure, and physician practice. In the United States, many patients do not have access to a simple way to shop and compare the price of common medical procedures. Due to the current managed care-based payor system in the US, the cost of treatment is often determined by managed care organizations.

These managed care organizations have specific formularies for drugs and procedures designed specifically to patients' individual health plans, which restrict the drugs and procedures available to patients in their plans. Patients have historically had no access to these price lists or formularies and have had very few tools to assist them in finding and comparing health care services or predetermining the cost of a procedure. Currently prospective patients who chose to compare medical costs are forced to conduct extensive, often inefficient, and time-consuming research to compare medical procedures prior to treatment.

The rising cost of healthcare is having a dramatic effect on the U.S. healthcare system. Healthcare costs continue to outpace pace inflationary growth, provider reimbursement rates continue to fall, and the cost of patient insurance premiums are increasing. To lower monthly premium costs, many patients are choosing to purchase (and employers are choosing to offer) high deductible health plans as an alternative to traditional higher premium PPO health plans.

These high deductible plans require patients to pay cash payments for medical services until the high deductible is satisfied, and once this deductible has been met, the insurance carrier begins to cover medical costs. As a result, many patients are seeing exponential increases in out-of-pocket expenses for medical procedures and services. In addition to more patients selecting high deductible plans, many patients cannot afford increased payments and are becoming uninsured or underinsured. As the number of patients who are uninsured, underinsured, or on high deductible plans grows, the need for a mechanism that allows patients to find discounted medical services increases and an efficient payment system.

SUMMARY OF THE INVENTION

Herein presented is an apparatus and associated methods for presenting users a selection of at least one bundled set of healthcare services provided discretely and/or individually by a plurality of respective providers, determining a bundle price for the bundled set of healthcare services, receiving payment for the user selected bundled set, generating a purchase data record hereafter interchangeably referred to as a "voucher" or "voucher data record" selectively redeemable by the user to receive each of the bundled healthcare services in the bundled set, transmitting a unique confirmation number generated for the purchase data record to track the redemption status of the purchase data record, disbursing payment allocated from the received payment to the plurality of respective providers and updating the redemption status of the purchase data record as each of the plurality of services of the bundled set are redeemed. The bundle price may be based on the user's health insurance deductible as well as the location and/or time at which the bundled set of services will be provided. The purchase data record may comprise an electronic health record.

The above-described and other features and advantages realized through the techniques of the present disclosure will be better appreciated and understood with reference to the following detailed description, drawings, and appended claims. Additional features and advantages are realized through the techniques of the present invention. Other embodiments and aspects of the invention are described in detail herein and are considered a part of the claimed invention.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description of exemplary embodiments of the present invention taken in conjunction with the accompanying drawings in which:

FIGS. 3A-3D are a number of screen shots illustrating examples of a graphical user interfaces that may be implemented by services provided within a customer portal in accordance with exemplary embodiments of the present invention.

FIG. 4B is an illustration of an example voucher that may be generated within a user interface by functions provided within a customer portal for a purchased service that is offered as a bundled set of services in accordance with exemplary embodiments of the present invention.

FIGS. 7A-7C are a number of screen shots illustrating examples of a graphical user interfaces that may be implemented by services provided within a provider portal in accordance with exemplary embodiments of the present invention.

Figure 1:
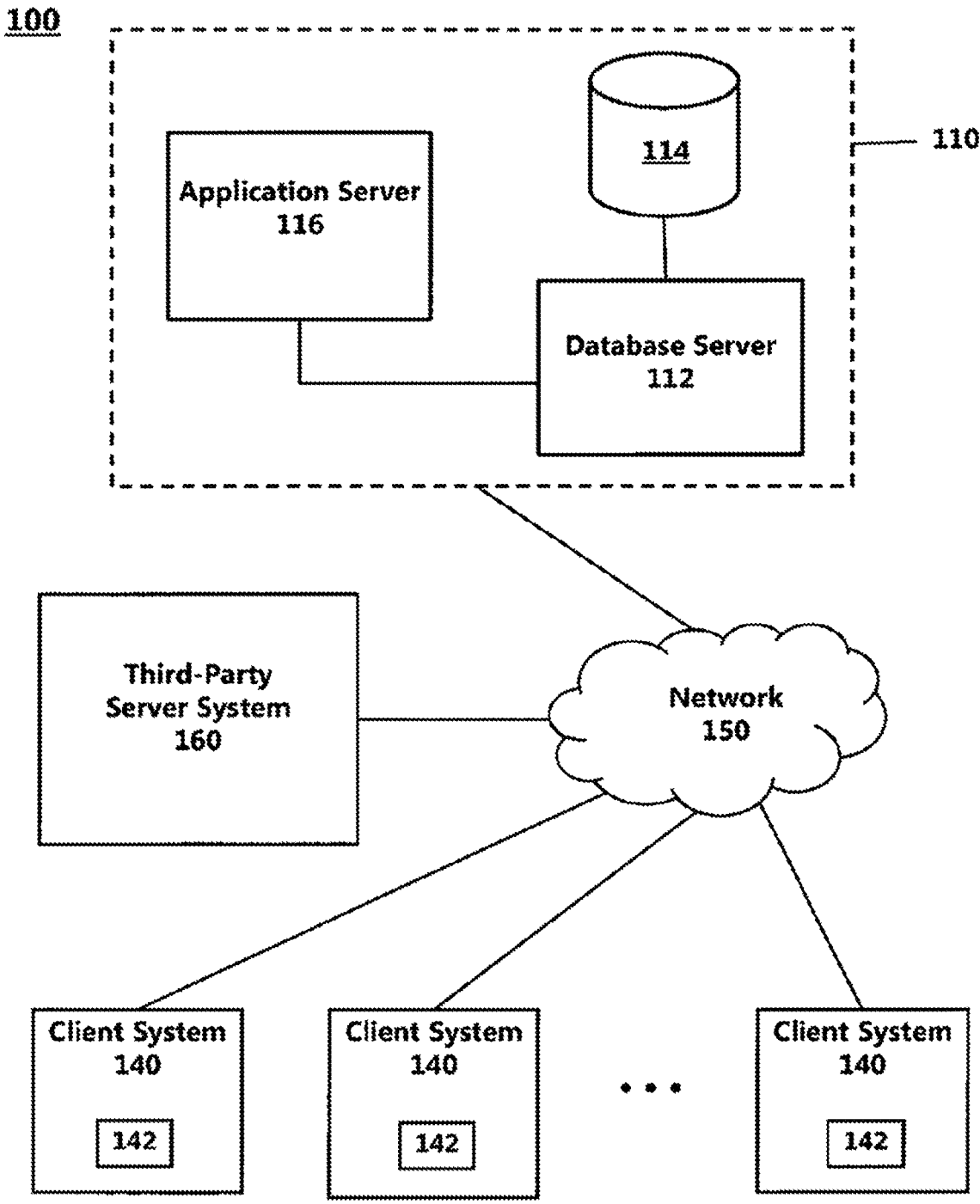
FIG. 1 is a schematic diagram illustrating an example network architecture for a healthcare marketplace system that can be configured to implement exemplary embodiments of the present invention.

The detailed description explains exemplary embodiments of the present invention, together with advantages and features, by way of example with reference to the drawings, in which similar numbers refer to similar parts throughout the drawings. The flow diagrams depicted herein are just examples. There may be many variations to these diagrams, or the steps (or operations) described therein without departing from the spirit of the invention. For instance, the steps may be performed in a differing order, or steps may be added, deleted, or modified. All these variations are considered to be within the scope of the claimed invention.

Like reference symbols in the various drawings indicate like elements.

DETAILED DESCRIPTION

While the specification concludes with claims defining the features of the invention that are regarded as novel, it is believed that the invention will be better understood from a consideration of the description of exemplary embodiments in conjunction with drawings. It is of course to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without these specific details. Further, the terms and phrases used herein are not intended to be limiting but rather to provide an understandable description of the invention.

As stated above, herein presented is an apparatus and associated methods for presenting users a selection of at least one bundled set of healthcare services provided discretely and/or individually by a plurality of respective providers, determining a bundle price for the bundled set of healthcare services, receiving payment for the user selected bundled set, generating a purchase data record selectively redeemable by the user to receive each of the bundled healthcare services in the bundled set, transmitting a unique confirmation number generated for the purchase data record to track the redemption status of the purchase data record, disbursing payment allocated from the received payment to the plurality of respective providers and updating the redemption status of the voucher as each of the plurality of services of the bundled set are redeemed. The purchase data record may be a voucher.

A bundled set may comprise a plurality of services or products. The services or products may comprise, for example, healthcare services, drugs, follow-up services, primary services, or a secondary service related to a primary service. The healthcare services may further comprise dental services. The dental services may comprise primary services. The dental services may further comprise one or more secondary service related to a primary service. The healthcare services may further comprise veterinary services. The veterinary services may comprise primary services. The veterinary services may further comprise one or more secondary service related to a primary service. A bundled set may comprise a set of healthcare services to be performed separately by respective providers. In the present disclosure the term "separately" may be interchangeably used with either of the terms "individually" or "discretely." The bundled set may be offered for purchase pre-paid at a bundle price. The bundle price may be a discounted price. The price may be discounted based on the location, time, or facility where at least one service of the bundled set will be performed. The price may be discounted based on a user's health insurance deductible. An amount of the received payment may be applied to the user's health insurance deductible. The bundle price may be determined based on the user's remaining health insurance deductible. Payment of the pre-paid bundle price may be received in virtual funds. Some implementations may disburse payment to providers of the services or products in the bundled set. The providers to which payment is disbursed may comprise a physician, a dentist, a dental hygienist, a dental lab, a veterinarian, a veterinary technician, a practice group, a hospital, or an insurer. A disbursed payment may comprise a plurality of payments allocated from a received payment, and the plurality of payments may be disbursed to a plurality of respective providers.

An implementation in accordance with the present disclosure may use a processor to generate a unique confirmation number for the purchased pre-paid bundled set of healthcare services, store the unique confirmation number to a purchase data record, and transmit the unique confirmation number to a user. The purchase data record may be a voucher. In the present disclosure the term "purchase data record" may be interchangeably used with either of the terms "voucher" or "voucher data record." The voucher data record may be stored or updated in a memory, or a data store operably coupled with the processor. The voucher data record may represent a voucher redeemable by the user to receive the at least one healthcare service of the bundled set of healthcare services. The voucher data record may comprise the unique confirmation number for the purchased bundled set of healthcare services. The voucher data record may further comprise a voucher redemption status for each healthcare service of the bundled set of healthcare services, permitting creation of a voucher that may be redeemed for a healthcare service purchased prepaid, and even more so, that said voucher can be used for each of the services of the bundled set of healthcare services separately. The voucher data record associated with the unique confirmation number is persistent and permits an individual bundled set of a group of bundled sets, or individual services comprising a bundled set of services, to be selectively redeemed.

The redemption status of each individual service or each individual bundled set may be updated in the data store or the memory to indicate the current voucher redemption status of each bundled set or each service in the bundled set of services, further enabling the same voucher uniquely identified by the confirmation number to persist for multiple service redemptions at different times and locations. The disclosed persistent voucher generation for selective redemption of bundled services provides a technical solution, necessarily rooted in computer and information technology disclosed herein, to the technical problem of persistently tracking and updating the redemption status for each service of a service bundle of services to be performed separately, as the individual services are selectively redeemed.

Exemplary embodiments of a transactional marketplace system in accordance with the present invention will now be described with reference to the drawings. Exemplary embodiments of the present invention may be implemented to provide healthcare service providers and pharmacies with a mechanism to remotely offer healthcare services and products to prospective patients at discounted rates in exchange for prepayment of the costs for the services and products via a network-based application (for example, a web-based application).

In this regard, exemplary embodiments may further be implemented to provide prospective patients with a mechanism to remotely search, compare, and make pre-paid purchases of such healthcare services and products offered by local medical service providers and pharmacies via a network-connected device configured to access the network-based application. Exemplary embodiments may be further implemented to provide healthcare service providers with the ability to remotely offer a bundled set of healthcare services that are performed separately by multiple providers to prospective patients through such a network-based mechanism in which the patient is provided the opportunity to make a prepaid purchase of such a bundled set of services in a single transaction via the network-connected device, whereby the network-based application facilitates a disbursed distribution of the payment among the multiple healthcare service providers that perform services included in the bundled set of services.

Exemplary embodiments may also be further implemented to provide a virtual payment system for facilitating and accounting for the exchange of payment for services and products purchased by (or otherwise on behalf of) patients and offered by healthcare providers via the transactional marketplace system in which a respective virtual money account is established and utilized for each participant in transactions conducted within the marketplace system to manage and track the process of exchanging actual currency and/or credits used to pay for the transactions through the use of corresponding virtual funds created within the virtual payment system.

In such exemplary embodiments, the virtual funds may be allocated and distributed to, exchanged among, and redeemed for corresponding amounts of actual currency by various participants to each transaction for which payment is facilitated through the virtual payment system, and the participants to transactions within the virtual payment system for which respective virtual money accounts are established and utilized may include, in addition to patients, healthcare providers, or other entities specified for receiving payments for services or products offered through the marketplace system, third party payers, and an entity that provides the transactional marketplace system.

Exemplary embodiments may be further implemented to provide various types of healthcare service providers, which may include individual physicians, practice groups, and hospital systems, with the ability to establish affiliations with one another through such a network-based mechanism and provide various options allowing the service providers to remotely offer healthcare services in association with these affiliations.

It should further be noted that various aspects of exemplary embodiments of the present invention described herein are not limited to healthcare services (also referred to herein as procedures) and products but, rather, may be implemented with respect to any suitable classes and types of services and products that may be offered by any suitable classes and types of service providers and retailers.

Referring now to FIG. 1, a schematic diagram illustrating an example network architecture for a healthcare marketplace system 100 that can be configured to implement exemplary embodiments of the present invention is provided. It should of course be understood that FIG. 1 is intended as an example, not as an architectural limitation for different embodiments of the present invention, and therefore, the elements depicted in FIG. 1 should not be considered limiting with regard to the environments within which exemplary embodiments of the present invention may be implemented.

In the example illustrated in FIG. 1, healthcare marketplace system 100 is implemented as a client/server system that includes a central server system 110 that is commonly accessed by each user of the system through operation of any of a plurality of client systems 140 that are operatively coupled to the central server system via a communication network 150. Central server system 110 further includes a database server 112 that is coupled to a data store 114 and an application server 116, and each client system 140 is a user terminal or other client device implementing software for and running a respective client application 142 for accessing services provided via a network-based application (also referred to herein as a network service) implemented by application server 116.

As further illustrated, exemplary marketplace system 100 may also include at least one third-party server system 160 to enable other functionality that may be accessed and utilized by server system 110 to provide and/or enhance the network service discussed herein. In exemplary embodiments, marketplace system 100 can include additional servers, clients, and other devices not shown in FIG. 1. The particular architecture depicted in FIG. 1 is provided as an example for illustrative purposes and, in exemplary embodiments, any number of client systems 140 may be connected to server system 110 at any given time via network 150, and server system 110 can comprise multiple server components and databases located within a single server system or within multiple server systems, where the multiple server systems are integrated with or accessible by users of client systems 140 as a distributed server system via network 150.

In exemplary embodiments, network 150 can be configured to facilitate communications between server system 110 and client systems 140, as well as communications with and between other devices and computers connected together within marketplace system 100, by any suitable wired (including optical fiber), wireless technology, or any suitable combination thereof, including, but not limited to, personal area networks (PANs), local area networks (LANs), wireless networks, wide-area networks (WAN), the Internet (a network of heterogeneous networks using the Internet Protocol, IP), and virtual private networks, and the network may also utilize any suitable hardware, software, and firmware technology to connect devices such as, for example, optical fiber, Ethernet, ISDN (Integrated Services Digital Network), T-1 or T-3 link, FDDI (Fiber Distributed Data Network), cable or wireless LMDS network, Wireless LAN, Wireless PAN (for example, IrDA, Bluetooth, Wireless USB, Z-Wave and ZigBee), HomePNA, Power line communication, or telephone line network. Such a network connection can include intranets, extranets, and the Internet, may contain any number of network infrastructure elements including routers, switches, gateways, etc., can comprise a circuit switched network, such as the Public Service Telephone Network (PSTN), a packet switched network, such as the global Internet, a private WAN or LAN, a telecommunications network, a broadcast network, or a point-to-point network, and may utilize a variety of networking protocols now available or later developed including, but not limited to the Transmission Control Protocol/Internet Protocol (TCP/IP) suite of protocols for communication.

In exemplary embodiments, application server 116, database server 112, and any other servers employed within server system 110 and third-party servers utilized within marketplace system 100 can be implemented within any suitable computing system or systems such as a workstation computer, a mainframe computer, a server system (for example, SUN ULTRA workstations running the SUN operating system, IBM RS/6000 workstations and servers running the AIX operating system, or an IBM zSeries eServer running z/OS, zNM, or LINUX OS), a server cluster, a distributed computing system, a cloud based computing system, or the like, as well as any of the various types of computing systems and devices described below with reference to the client systems 140. Server system 110 may be implemented using any of a variety of architectures. For example, application server 116 and database server 112 may also be implemented independently or as a single, integrated device. While the exemplary embodiment illustrated in FIG. 1 depicts application server 116 and database server 112 as individual components, the applications provided by these servers, or various combinations of these applications, may be server applications running on separate physical devices. In this regard, server system 110 may comprise a number of computers connected together via a network and, therefore, may exist as multiple separate logical and/or physical units, and/or as multiple servers acting in concert or independently, wherein each server may be comprised of multiple separate logical and/or physical units. In exemplary embodiments, server system 110 can be connected to network 150 through a collection of suitable security appliances, which may be implemented in hardware, software, or a combination of hardware and software.

As illustrated in FIG. 1, application server 116 is communicatively coupled to database server 112. Database server 112 is connected to data store 114, which comprises a plurality of databases that are maintained by database server 112, accessed by application server 116 via database services provided at a front end by database server 112, and store information on a variety of matters that is utilized in providing the services offered via the network service provided by the application server, as described below in greater detail.

The machine learning algorithm 15 instructs the service offer database 114h to store each healthcare service provider service corresponding to the user selection and displays the bundled set of service offers via the graphical user interface/provider portal 130 that matches the users' selection.

Any machine-learning algorithm 15 can be employed, such as neural networks, expert systems, Bayesian belief networks, fuzzy logic, data fusion engines and the like. The system may also employ combinations of various artificial intelligence techniques to the service offer database 114h.

The machine learning algorithm 15 takes into account of each and every parameter of user inputs such as type of disease, location, expertise, procedures, hospitals, pricing etc. Thus, the machine learning algorithm 15 displays the best results/hits based on the inputs and preferences of the user.

As used herein, the term "data store," "data storage unit," storage device, and the like can to any suitable memory device that may be used for storing data, including manual files, machine-readable files, and databases. In exemplary embodiments, application server 116, database server 112, and data store 114 may have implemented together a single computing device, implemented within a plurality of computing devices locally coupled to each other via a suitable communication medium, such as a serial port cable, telephone line or wireless frequency transceiver, implemented within a plurality of computing devices remotely coupled to each other via network 150, or any suitable combination thereof.

Client systems 140 are computer devices to which one or more users, which may be healthcare providers offering services or products or patients seeking to purchase healthcare services or products, or their human agents (for example, personal representatives or assistants), have access. It should be noted that the term "user" is used herein to refer to one who uses a computer system, such as one of client systems 140. As described in greater detail below, client systems 140 are each operable by such users to access server system 110 via network 150 and act as clients to access services offered by the network service provided by the server system within exemplary marketplace system 100. For this purpose, each client system includes a respective client application 142 that executes on the client system and allows a user to interact with server system 110 via application server 116.

In exemplary embodiments, the computer systems of client systems 140 can be any of a wide range of suitable computing devices such as one or more workstations, desktop computers, laptops, or other personal computers (PCs) (for example, IBM or compatible PC workstations running the MICROSOFT WINDOWS operating system or LINUX OS, MACINTOSH computers running the MAC OSX operating system, or equivalent), non-traditional-computer digital devices such as Personal Digital Assistants (PDAs) and other handheld or portable electronic devices, smart phones and other mobile handsets, tablet computers, netbook computers, game consoles, home theater PCs, desktop replacement computers, and the like, or any other suitable information processing devices. An exemplary computer system for client systems 140 is described in greater detail below with reference to FIG. 5.

In general, during operation of exemplary marketplace system 100, a client system 140 first establishes a connection to server system 110 via network 150. Once the connection has been established, the connected client system may directly or indirectly transmit data to and access content from the application server 116. A user accessing application server 116 through the connected client system can thereby to use a client application 142 to access services provided by the application server, which are described in greater detail below, via a user interface implemented by the client application within which the client application renders the information served by the application server.

In exemplary embodiments, application server 116 can implement network service as a non-web client application (such as a mobile application), a web client application, or both to provide the services accessed by client systems 140 within server system 110, and client applications 142 can correspondingly be implemented as non-web client applications, web client applications, or both for operation by users of the client systems to interact with application server 116 and access the services provided thereby. For example, application server 116 can comprise a web server configured to provide a web application for the respective client applications implemented on client systems 140 that are configured to provide web-based user interfaces for utilizing the services provided by the web server. For instance, the user interfaces of client applications implemented on client systems 140 can be configured to provide various options corresponding to the functionality offered in exemplary embodiments described herein through suitable user interface controls (for example, by way of menu selection, point-and-click, dialog box, or keyboard command). In one general example, the user interfaces may provide "send" or "submit" buttons that allow users of client applications to transmit requested information to application server 116. The user interfaces can be implemented, for example, as a graphical user interface (GUI) that renders a common display structure to represent the network service provided by application server 116 for a user of a client platform.

More specifically, in such an example, application server 116 can, for example, be configured to provide services via a web-based software application hosting a corresponding website that includes a number of web pages (e.g., screens), and client applications 142 can comprise a web browser executing on client systems 140, such that the services provided by application server 116 are accessible to client systems 114 using the Internet or an intranet. Users of client systems 140 may thereby access the website provided by application server 116 by, for example, inputting or following a link to the uniform resource locator (URL) for the website in the web browser, which then enable users to display and interact with information, media, and other content embedded within the web pages of the website provided by application server 116. The web-based software application can transmit information that can be processed by the web browsers to render a user interface using, for example, a browser-supported programming languages such as JavaScript, HTML, HTML5, and CSS, or the like, and can communicate with the web browsers using, for example, HTTPS, POST and/or GET requests. Client applications 142 and application server 116 may be configured so that information transmitted between client systems 140 and server system 110 can be encrypted and sent over a secure network connection to protect, for example, patient privacy.

Figure 2:
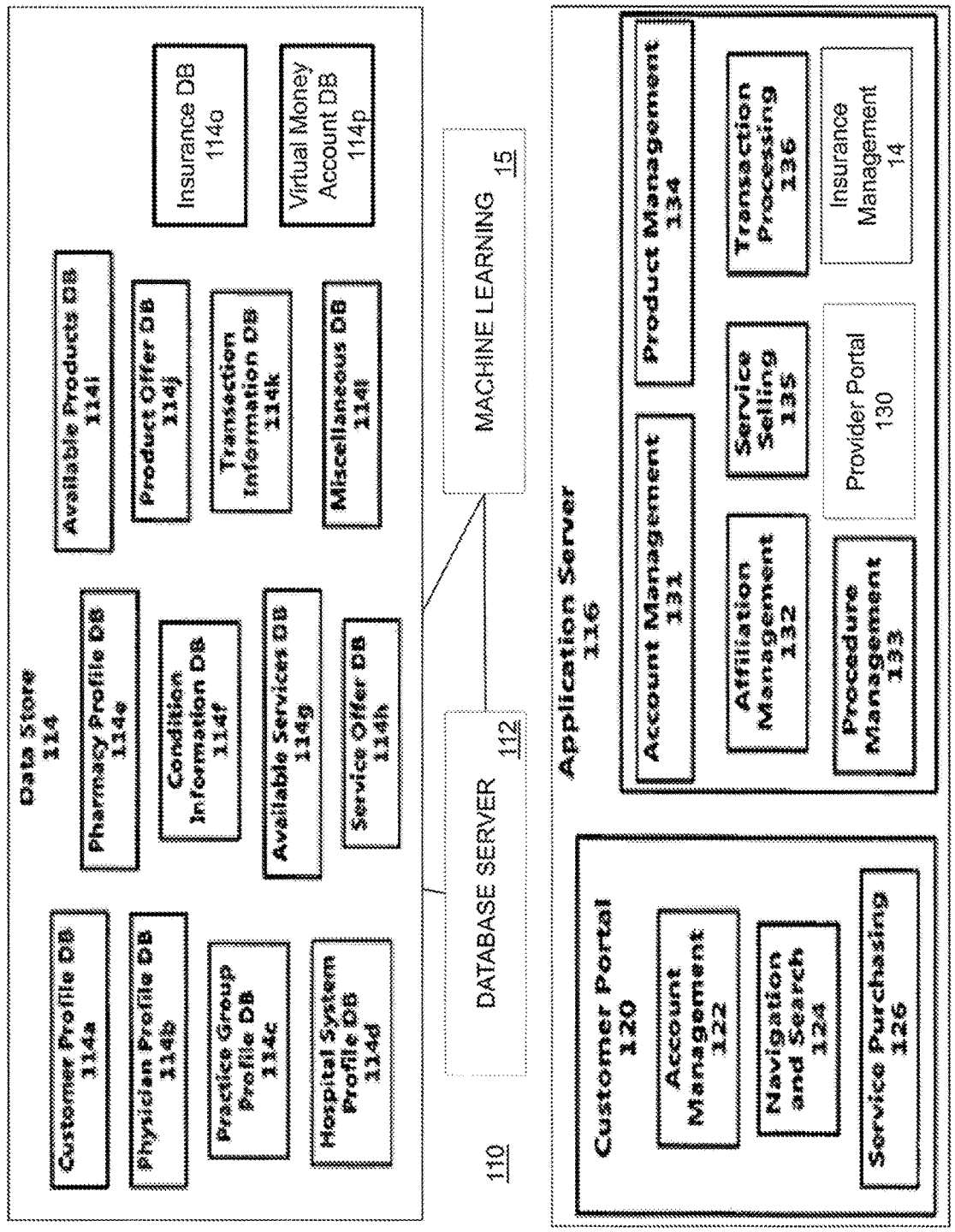
FIG. 2 is a block diagram illustrating a server system in accordance with an exemplary embodiment of the present invention.

Referring now to FIG. 2, a block diagram illustrating an exemplary embodiment of server system 110 is provided. As illustrated in FIG. 2, application server 116 is implemented to provide a plurality of services via a customer portal 120 and a plurality of services via a provider portal 130. As described herein, application server 116 can be implemented to provide a respective set services for each of various types of users (for example, unregistered guests, customers, individual physicians, nurses, office staff, practice group administrators, hospital system administrators, pharmacy administrators, and the like), and some of the services offered by application server 116 can be commonly applicable to and accessible by all types of users, while other services can be applicable to and accessible only by specific types of users.

For purposes of description, the terms "providers" and "provider users" are used herein to refer to the general class of users that register with the system offer healthcare services or products for purchase by customer users registered with the system, which can include individual physician users, practice group administrators, hospital system administrators, pharmacy administrators, and the like. In addition, a user account for a particular provider can have any number of authorized users. As an example, an account established for a physician can have the physician as one of its users. It can also have nurses or office staff working for the physician as other authorized users. The other authorized users can log into the account and perform various actions with the permission and under the supervision of the physician.

A single hospital system account may be established and shared by multiple staff member's hospital system. For purpose of illustration, there can be a designated user (for example, an account administrator) who is responsible for managing the account. The administrator can be provided with greater access rights within server system 110 with respect to the account. In exemplary embodiments, the particular client applications 142 or the particular client systems 140 that are utilized for accessing application server 116 can be respective to and customized for each type of user account. For example, the particular client application that is utilized for each type of account can be implemented to a provide virtual computing platform that is specific to the services offered for that type of account.

As further illustrated in exemplary embodiment of FIG. 2, and as will also be described in greater detail below, data store 114 comprises a plurality of databases that are maintained and accessible by application server 116 via database server 112, including a customer profile database 114a, a physician profile database 114b, a practice group profile database 114c, a hospital system profile database 114d, a pharmacy profile database 114e, a condition information database 114f, an available services database 114g, a service offer database 114h, an available products database 114i, a product offer database 114j, a transaction information database 114k, and one or more additional databases 114l that may be used for storing any other suitable information that may be utilized by server system 110 (for example, system usage data, audit trail data, data used internally within the system by application server 116, and the like).

The customer profile database 114a is configured to register users thereby providing user's personal information for purchasing healthcare services. The physician profile database 114b is configured to register and maintain records of individual physician offering healthcare services. The condition information database 114f is configured to register and maintain information records for various health conditions and diseases for which corresponding healthcare services are offered.

Physician profile database 114b is used to maintain account information records for individual physician users that register with server system 110 to offer healthcare services for purchase by customer users registered with the system, as well as account information records for individual physicians that are registered with the system in association with a practice group or hospital system (as described in greater detail below). For each physician for which an account is registered with server system 110, various items of information relevant to the physician, such as name, practice specialty, office location(s) and hours, a profile picture, contact information, biographical information (such as awards, honors, publications, patient testimonials, and other information that can be helpful for marketing the physician to customers accessing the system), URLs or references to websites and social media profiles, group practice and hospital affiliation(s), outside facilities that are used for particular procedures performed by the physician (for example, particular hospitals or clinics), compensation information (indicating a financial account for receiving payment for purchases of services offered by the physician via the system), and any other suitable identifying information, as well as a unique user name and password associated with the account that can be used to log into the account, may be included in the respective account information record for the physician that is maintained within physician profile database 114b. The account information record for each physician can also be associated with an account status and a unique physician account identifier within physician profile database 114b that is used by application server 116 for performing various operations.

Practice group profile database 114c is used to maintain account information records for practice group administrator users that register with server system 110 to offer healthcare services provided by physicians affiliated with a practice group for purchase by customer users registered with the system. For each practice group for which an account is registered with server system 110, various items of information relevant to the practice, such as practice group name, location and hours, contact information, URLs or references to websites and social media profiles for the practice group, physician and hospital affiliation(s), outside facilities that are used for particular procedures performed by physicians affiliated with the practice group, compensation information (indicating a financial account for receiving payment for purchases of services offered by affiliated physicians via the system), and any other suitable identifying information, as well as a unique user name and password associated with the account that can be used by the practice group administrator to log into the account, may be included in the respective account information record for the practice group that is maintained within practice group profile database 114c. The account information record for each practice group can also be associated with an account status and a unique practice group account identifier within practice group profile database 114c that may be used by physician users registered with the system for affiliating with the practice group and used by application server 116 for performing various operations.

The hospital system profile database 114d is configured to register and maintain account information records for hospital system administrators providing pre-paid healthcare services. Hospital system profile database 114d is used to maintain account information records for hospital system administrator users that register with server system 110 to make on-site, in-person sales of pre-paid healthcare services provided by physicians affiliated with a hospital system for purchase by patients operating client systems within marketplace system 100. For each hospital system for which an account is registered with server system 110, various items of information relevant to the hospital system, such as practice group and physician affiliation(s), facilities that are used for particular procedures performed by physicians affiliated with the hospital system, compensation information (indicating a financial account for receiving payment for purchases of services offered by affiliated physicians via the system), and any other suitable identifying information, as well as a unique user name and password associated with the account that can be used by the hospital system administrator to log into the account, may be included in the respective account information record for the hospital system that is maintained within hospital system profile database 114d. The respective account information record for the hospital system may further include a plurality of unique user names and passwords associated with the account that can be respectively used by hospital system staff members to log into the account The account information record for each hospital system can also be associated with an account status and a unique hospital system account identifier within hospital system profile database 114d that may be used by physician users registered with the system for affiliating with the hospital system and used by application server 116 for performing various operations.

Pharmacy profile database 114e is used to maintain account information records for pharmacy administrators that register with server system 110 to offer healthcare products, such as prescription drugs and medical supplies, for purchase by customer users registered with the system. For each pharmacy for which an account is registered with server system 110, various items of information relevant to the pharmacy, such as name, location(s) and hours, contact information, URLs or references to websites and social media profiles, compensation information (indicating a financial account for receiving payment for purchases of products offered by the pharmacy via the system), and any other suitable identifying information, as well as a unique user name and password associated with the account that can be used to log into the account, may be included in the respective account information record for the pharmacy that is maintained within pharmacy profile database 114e. The account information record for each pharmacy can also be associated with an account status and a unique pharmacy account identifier within pharmacy profile database 114e that is used by application server 116 for performing various operations.

Condition information database 114f is used to maintain information records for various health conditions and diseases for which corresponding healthcare services (for example, test and treatments) that can be offered by providers registered with server system 110 for purchase by customer users registered with the system. In exemplary embodiments, the various conditions, and diseases for which respective information records are maintained in condition information database 114f and the information that populates the respective information record for each condition or disease can be created and maintained by a back-end administrator of server system 110. For each condition or disease for which an information record is created, various items of information relevant to the condition or disease, such as name, description, causes, risk factors, symptoms, common treatments, corresponding healthcare services that can be offered by providers registered with server system 110 (for example, each associated healthcare service may be identified within the information record using a unique procedure identifier that is used to identify an information record for the service within available services database 114g as discussed below), and any other suitable information may be included in the respective information record for the condition or disease that is maintained within condition information database 114f.

The available service database 114g is configured to register and maintain records of various healthcare services offered by at least one of: a physician; and a hospital. Available services database 114g is used to maintain information records for various healthcare services (for example, test and treatments) that can be offered by providers registered with server system 110 for purchase by customer users registered with the server system. In exemplary embodiments, the respective information records for healthcare services that are maintained in available services database 114g and the information that populates the respective information record for each service can be created and maintained by a back-end administrator of server system 110. For each service for which an information record is created, various items of information relevant to the service, such as name, procedure detail, one or more medical specialties with which the procedure is commonly associated, cost information (for example, average prices for the service for patients that are uninsured and/or have a high deductible insurance plan and an average price for purchasing the service that is offered by providers registered with server system 110), a medical code number identifying the service according to the nomenclature used by a formal medical classification system (for example, a code that is used to identify the service according to the Current Procedural Terminology (CPT) code set), a procedure identifier that is used by application server 116 to uniquely identify the particular service, and any other suitable information may be included in the respective information record for the service that is maintained within available services database 114g.

Additionally, in exemplary embodiments, the information record for each service that is maintained within available services database 114g may further include an indication of the whether the service can be offered by providers within marketplace system 100 as an individual primary service or as a primary service of a bundled set of a plurality of services (for which a single payment for the bundled set of services will be disbursed to different provider for each of the services in the bundled set). In such embodiments, for each service for which the information record includes an indication that the service is offered as a primary service of a bundled set of services, various items of additional information relevant to the bundled set of services associated with the service that is indicated to be a primary service may be included in the respective information record for the primary service that is maintained within available services database 114g. Such items of information relevant to the bundled set of services included in the respective information record for a primary service may include, for example, items of information describing one or more secondary services associated with the primary service (such as name, a medical code number such as a CPT code identifying the service according to the nomenclature used by a formal medical classification system, and a secondary procedure identifier that is used by application server 116 to uniquely identify the particular secondary service in association with the unique procedure identifier for the primary service), one or more procedure identifiers for other services for which an information record is maintained within available services database 114g that are considered to be secondary services associated with the primary service, an indication of whether performance of each of the one or more secondary services (for which a single customer payment for the bundled set of services will be disbursed among different respective providers for the services in the bundled set) is optional or required in association with performance of the primary service, and an indication of whether the primary service is required to be performed at an outside facility. In addition, in such embodiments, for each service for which the information record includes an indication that the service is offered as a primary service of a bundled set of services, the cost information that is included in the respective information record for the primary service that is maintained within available services database 114g can include respective cost information for each of the primary service, the one or secondary services, and, if required, the use of an outside facility for the primary service individually (for example, average prices for each service and facility of the bundled set of services for patients that are uninsured and/or have a high deductible insurance plan) in addition to an average price for purchasing the bundled set of services that is offered by providers registered with server system 110.

Service offer database 114h is used to maintain information records for healthcare services that are being offered by providers registered with the system for purchase by customer users registered with the system. In this regard, it should be noted that the same service may be separately offered by multiple different providers registered with the system and, thus, service offer database 114*h* can include multiple information records for the same service that are each associated with a different provider. For each offered service for which a respective information record is maintained within service offer database 114*h*, various items of information relevant to the service being offered, such as the unique procedure identifier for the information record within available services database 114*g* for the service, the unique account identifier for the account information record (within physician profile database 114*b*, practice group profile database 114*c*, or hospital system profile database 114*d*) of the provider that is offering the service through the system, the unique physician account identifier for the account information record within physician profile database 114*b* of the physician user that will perform the service, a location at which the service will be performed, a discounted price for purchasing the service within marketplace system 100, a regular price for the service when the service is purchased outside of the system, the unique account identifier for the account information record (within physician profile database 114*b*, practice group profile database 114*c*, or hospital system profile database 114*d*) of the provider for which payment for the service when purchased through the system is to be directed, a payment amount to be transferred to the provider for which payment for performing the service is to be directed, additional descriptive information that may be provided by the provider offering the service, a procedure offer identifier that is used by application server 116 to uniquely identify the offering of the particular service by the provider within the system, and any other suitable information may be included in the respective information record for the offered service that is maintained within service offer database 114*h*.

Additionally, in exemplary embodiments, the information records for offered services that are maintained within service offer database 114*h* can include information records that include additional information for services that are offered by providers registered with the system as a bundled set of services. In this regard, the information record for each offered service that is maintained within service offer database 114*h* may further include an indication of the whether the offered service is being offered as an individual primary service or as a primary service of a bundled set of a plurality of services (for which a single customer payment for the bundled set of services will be disbursed among different respective providers for the services in the bundled set). In such embodiments, for each offered service for which the information record includes an indication that the service is being offered by a provider as a primary service of a bundled set of services, various items of additional information relevant to the bundled set of services associated with the offered service that is indicated to be a primary service may be included in the respective information record for the offered service that is maintained within service offer database 114*h*. Such items of information relevant to the bundled set of services included in the respective information record for an offered service within service offer database 114*h* that is indicated to be a primary service of a bundled set of services may include, for example, items of information for each secondary service such as the unique procedure identifier for the information record within available services database 114*g* for the secondary service (or the secondary procedure identifier that is included in the available services database 114*g* to uniquely identify the particular secondary service in association with the unique procedure identifier for the offered primary service where the information record for the primary service being offered in the available services database 114*g* includes an indication that the service is offered as a primary service of a bundled set of services), the unique physician account identifier for the account information record within physician profile database 114*b* of the physician user that will perform the secondary service, a location at which the service will be performed, a discounted price for purchasing the secondary service within marketplace system 100, a regular price for the secondary service when the service is purchased outside of the system, the unique account identifier for the account information record (within physician profile database 114*b*, practice group profile database 114*c*, or hospital system profile database 114*d*) of the provider for which payment for the secondary service when purchased through the system is to be directed, a payment amount to be transferred to the provider for which payment for performing the secondary service is to be directed, and an indication of whether performance of the secondary service is optional or required in association with performance of the primary service. The items of information relevant to the bundled set of services included in the respective information record for an offered service within service offer database 114*h* that is indicated to be a primary service of a bundled set of services may further include, for example, an indication of whether the primary service is to be performed at an outside facility and, if the primary service is to be performed at an outside facility, items of information pertaining to each of one or more facilities that may be used to perform the primary service such as, for example, name, address, contact information, facility fee, and compensation information indicating a financial account that is used by the facility for receiving a facility fee.

Available products database 114*i* is used to maintain information records for various healthcare products (for example, prescription drugs and medical supplies) that can be offered by pharmacies registered with server system 110 (that is, pharmacies for which an account information record is maintained within pharmacy profile database 114*e*) for purchase by customer users registered with the system. In exemplary embodiments, the respective information records for the healthcare products that are maintained in available products database 114*i* and the information that populates the respective information record for each product can be created and maintained by a back-end administrator of server system 110. For each product for which an information record is created, various items of information relevant to the product, such as name(s), a list of dosage level options (for prescription drugs), size options (for certain medical supplies), and the like, a description of the product, an indication of whether a prescription is required to purchase the product, information for rendering a respective predefined fillable form for submitting prescription information for the product within a user interface, cost information (for example, average prices for the product for patients that are uninsured and/or have a high deductible insurance plan and a lowest price for purchasing the product that is offered for the service by pharmacies registered with server system 110), a product identifier that is used by application server 116 to uniquely identify the particular product, and any other suitable information may be included in the respective information record for the product that is maintained within available products database 114*i*.

Product offer database 114*j* is used to maintain information records for healthcare products that are being offered by pharmacies registered with the system for purchase by customer users registered with the system. In this regard, it should be noted that the same product may be separately offered by multiple different pharmacies registered with the system and, thus, product offer database 114*j* can include multiple information records for the same product that are each associated with a different provider. For each product offered by a pharmacy for which a respective information record is maintained within product offer database 114*j*, various items of information relevant to the product being offered, such as the unique product identifier for the information record within available products database 114*i* for the product, the unique pharmacy account identifier for the account information record within pharmacy profile database 114*e* of the pharmacy that is offering the product, a discounted price for purchasing the product from the identified pharmacy within marketplace system 100, a regular price for the product when the service is purchased outside of the system from the identified pharmacy, a payment amount to be transferred to the pharmacy that is offering the product, additional descriptive information that may be provided by the pharmacy offering the product, a product offer identifier that is used by application server 116 to uniquely identify the information record for the offering of the particular product by the pharmacy within the system, and any other suitable information may be included in the respective information record for the offered product that is maintained within product offer database 114*j*.

The transaction information database 114*k* is configured to maintain records of purchases made by registered users. Transaction information database 114*k* is used to maintain information records for purchases that have been made via the system by registered customer users of healthcare services and products being offered by registered providers. For each purchase of a service or product that has been made using the system, various items of information relevant to the purchase may be included in the respective information record for the purchase that is maintained within transaction information database 114*k*. In general, the items of information relevant to each purchase that is included in the respective information record for the purchase that is maintained within transaction information database 114*k* can include, for example, the unique customer account identifier of the account information record for the purchasing customer within customer profile database 114*a*, the unique procedure offer identifier of the information record for a purchased service within service offer database 114*h* or the unique product offer identifier of the information record for a purchased product within product offer database 114*j*, a purchase date, and a unique transaction identifier that is used by application server 116 to uniquely identify the information record for the purchase of the service or product within the system. For each purchase of a service that has been made using the system, the items of information relevant to the purchase included in the respective information record for the purchase that is maintained within transaction information database 114*k* may further include the unique physician account identifier for the account information record within physician profile database 114*b* of the physician user that is designated as performing the purchased service in the information record for the purchased service within service offer database 114*h*, an indication of whether the purchase has been redeemed and, if the purchase has been redeemed, a redemption date.

Additionally, in exemplary embodiments, the information records for purchased services that are maintained within transaction information database 114*k* can include information records that include additional information for purchases and services that are offered by providers registered with the system as a bundled set of services. In this regard, the information record for each purchased bundled set of services that is maintained within transaction information database 114*k* may include an indication of a particular outside facility that has been selected for performing the primary service of the bundled set of services and, for each service of the bundled set of services that is included within the purchase (for example, each required secondary service or each optional secondary service selected by the customer user to be included within the purchase, as well as the primary service), the unique physician account identifier for the account information record within physician profile database 114*b* of the physician user that is designated as performing the service in the information record for the purchased service within service offer database 114*h*, an indication of whether the purchase has been redeemed with respect to that particular service, and, if the purchase has been redeemed with respect to that particular service, a redemption date for that particular service.

Figure 3A:
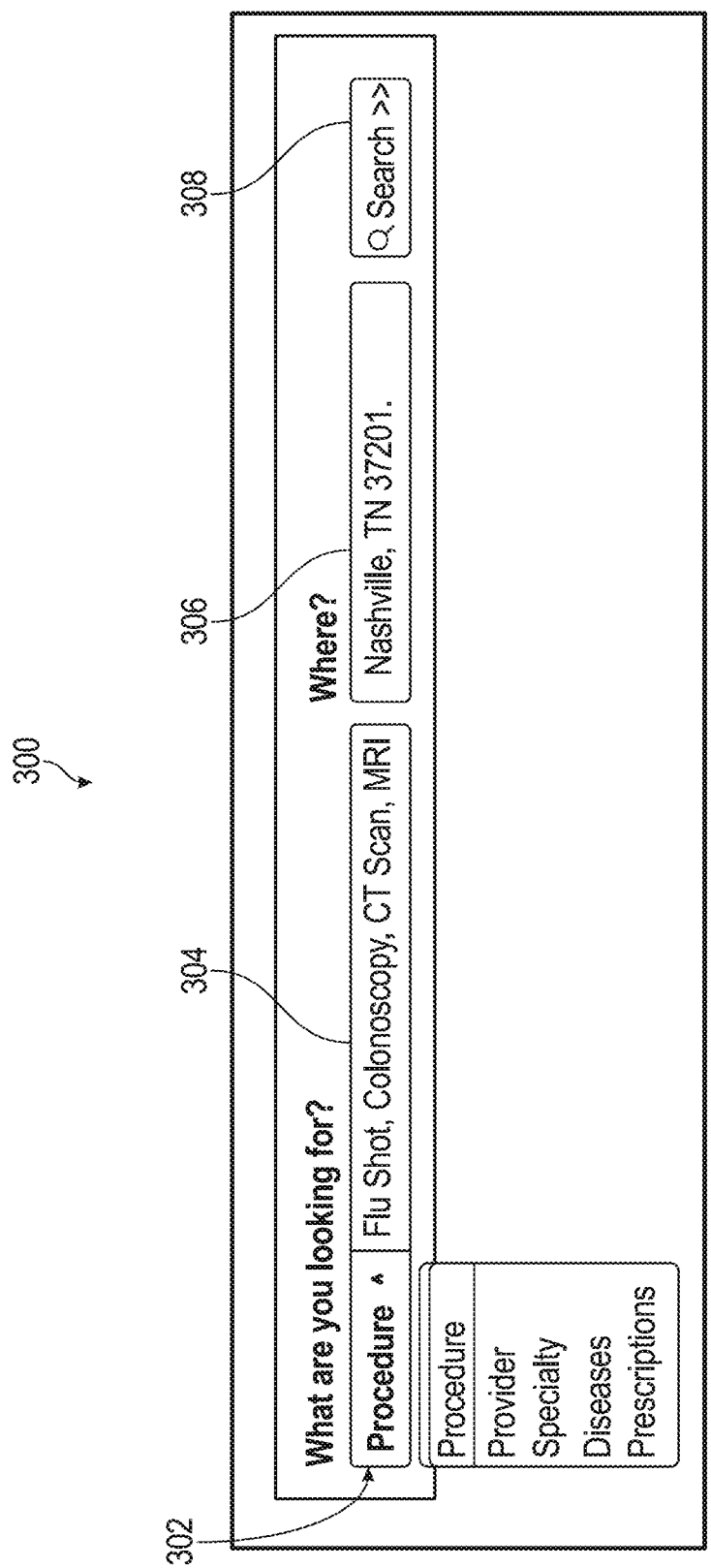

FIG. 3A is a screen shot illustrating an example of a graphical user interface provided by such a home page 300 for customer portal 120. In the illustrated example, the search interface provided at home page 300 can include a drop-down menu 302, a search entry field 304, a location entry field 306, and a search button 308. Drop-down menu 302 provides a set of selectable options that allow the user to search for procedures offered by provider users registered with the system, particular products offered by pharmacy users registered with the system, information on providers registered with the system, and information on health conditions that is maintained within system. In exemplary embodiments, navigation, and search service 124 can be configured to use location information that may be gathered by any suitable location determining functionality implemented on the client system to provide a default location entry (for instance, city name and/or zip code) within location entry field 306. In such embodiments, navigation, and search service 124 may be further configured to request permission from the user via the user interface to be able to access and utilize such location information for this purpose.

In one example, when the user selects the option within drop-down menu 302 to search for a particular service offered by provider users registered with the system, the user can then proceed to enter the name of the service within search entry field 304 In conjunction with selecting the particular service, the user can also enter a city name and/or zip code or opt to utilize a default location entry within location entry field 306 to localize a search radius for providers offering the selected service for purchase via marketplace system 100.

Once the appropriate search information is entered, the user can then select the search button to direct navigation and search service 124 to conduct a search of local providers registered with server system 110 and offering the inputted healthcare service for purchase via marketplace system 100. Navigation and search service 124 can conduct such a location-based search by accessing, for example, service offer database 114*h* in conjunction with physician profile database 114*b*, practice group profile database 114*c*, hospital system profile database 114*d*, and/or any other suitable information and databases to which the application server has access to filter the information records included within available services database 114*g* for healthcare services that match the specified search criteria, and then present the results of the search to user within a search result listing page.

In exemplary embodiments, whenever navigation and search service 124 is directed to conduct a location-based search by a user (for example, for local providers offering the inputted healthcare service or, as discussed below, for local providers generally or for local pharmacy providers offering healthcare products), the navigation and search service can be configured to maintain the location specified within location entry field 306 for search within a data object for a session with application server 116 that is maintained for the user.

Figure 3B:
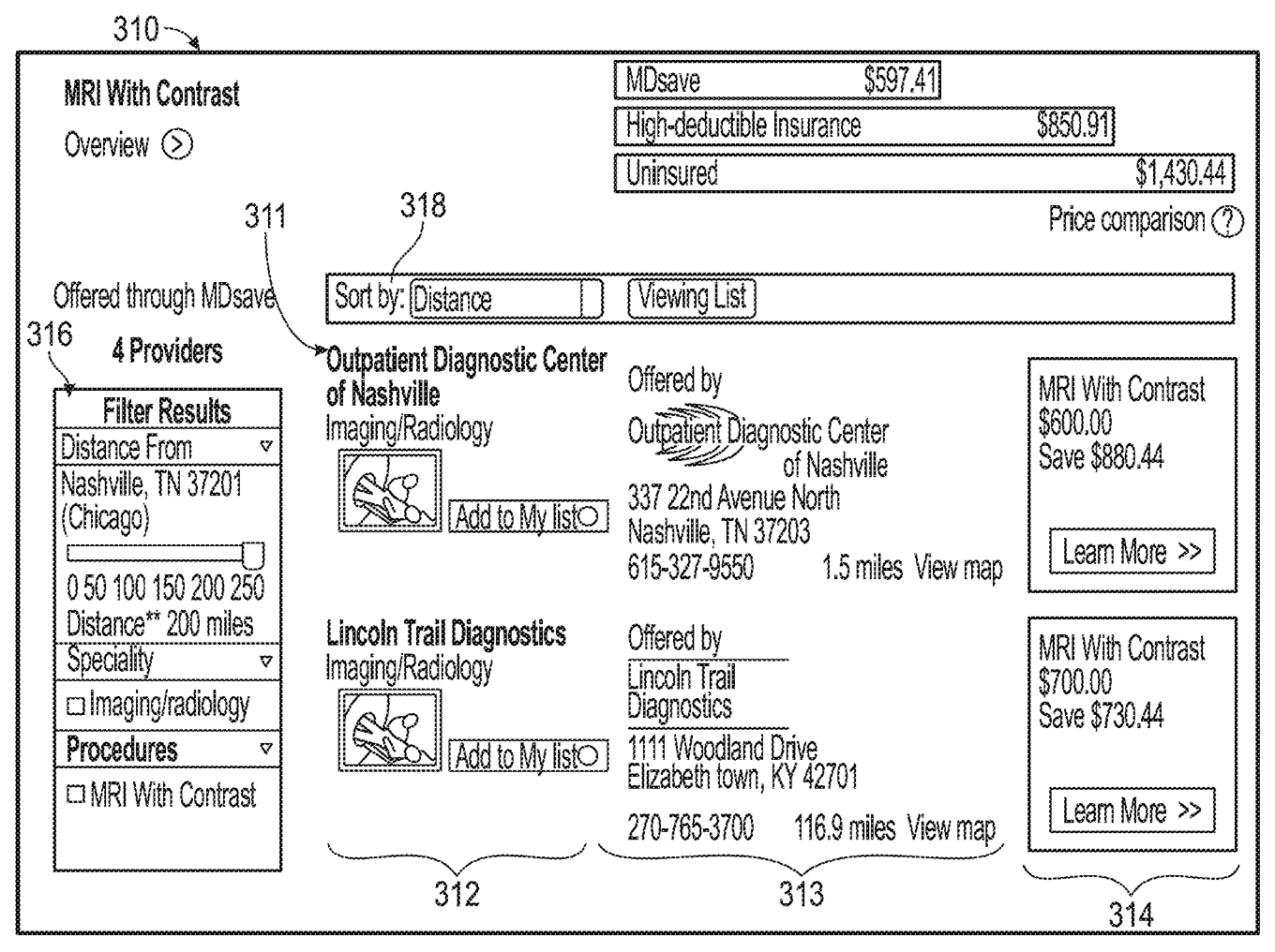

FIG. 3B is a screen shot illustrating an example of a GUI provided by a search result listing page 310 for customer portal 120 that presents a list of providers offering the service specified within search entry field 304 within a default search radius (for example, 50 miles) of the location specified within location entry field 306 returned in the search conducted by navigation and search service 124. In the illustrated example, search result listing page 310 includes a result listing section 311, a result filtering section 316, and a result sorting section 318. Result filtering section 316 provides various user interface controls for refining the results of the search presented within result listing section 311 by modifying the search criteria or inputting additional search criteria. In the illustrated example, result filtering section.

In exemplary embodiments, such a search result listing page 310 can be implemented to present any other appropriate information relevant to the search criteria specified by the user, such as, for example, a graphic depicting the average cost information included in the information record for the particular product specified in the search criteria that is maintained in available products database 114j (for prescription drug products, the average cost information can be provided for a default quantity of the prescription drug or, alternatively, based on a calculation performed by navigation and search service 124 for the quantity specified by the user using the average cost information for a default quantity as a reference). Each entry for an offered product listed in the product search result listing page can include portions presenting information from the account information record of the pharmacy that is offering the product through the system (for example, pharmacy name, address, and contact information), cost information for purchasing the offered product through marketplace system 100 (for example, the discounted price for the product that is specified in the information record for the offered product within product offer database 114j or, for prescription drugs, a price that is calculated based on the specified discounted price in relation to the quantity specified by the user) and a cost savings difference between the discounted price and the regular price for the product when the product is purchased outside of the system as specified in the information record for the offered product), and an option to select to purchase the offered product listed in the entry (for example, via an "Add to Cart" button). When a user selects the option to purchase an offered product listed in the product search result listing page, navigation and search service 124 can be configured to update the session data object for the session with application server 116 that is presently being maintained for the user to include an indication that the user has selected the offered product for purchasing (for example, by including the product offer identifier that is maintained within product offer database 114j to uniquely identify the offering of the particular product by the pharmacy) in association with any other required information (for example, in the case of a prescription drug, the quantity that is specified by the user and the price that is calculated based on the discounted price for the product that is specified in the information record for the offered product within product offer database 114j in relation to the quantity specified by the user). Upon selecting one or more services and/or products for purchase in association with a session with application server 116, the user may then have an option to navigate to a customer purchase page (for example, a "Check-Out" page) to proceed with purchasing the selected item(s) with respect to an account information record maintained within customer profile database 114a for a registered customer user.

For each offered service for which a respective entry is included in the purchase information section, the entry may include, for example, information retrieved from physician profile database 114b, available services database 114g, service offer database 114h, and the session data object such as the name of the physician that will perform the service, a service name, and an indication of whether the service is being offered as a primary service of a bundled set of services. Each entry for an offered service that is included in the purchase information section may further include user interface controls accessible by the user to remove the offered service from the purchase information section (and correspondingly direct purchasing service 126 to remove the indication the offered service as having been selected in the session data object) and/or to adjust a service quantity to be purchased by the user, and a price for purchasing the offered service that is calculated based on the service quantity specified by the user and the discounted price for the service that is specified in the information record for the offered service within service offer database 114h in relation to the quantity specified by the user.

In addition, for each entry for an offered service included in the purchase information section that is being offered as a primary service of a bundled set of services, the entry may further include user interface controls accessible by the user to present additional information about the bundled set of services and make additional selections regarding the offered service. The additional information may include, for example, information retrieved from physician profile database 114b, available services database 114g, and service offer database 114h, such as the name of physician that will perform each secondary service, a service name for each secondary service, an indication of whether each secondary service is required or optional, and an indication of whether the primary service is required to be performed at an outside facility. In association with each secondary service for which an indication that the secondary service is optional is presented, the additional information may further include the discounted price for the secondary service that is specified in the information record for the offered service within service offer database 114h, and an associated user interface control may be provided that allows the user to select whether to purchase the optional secondary service in association with the offered service. In association with an indication that the primary service is required to be performed at an outside facility, the additional information may further include name and location information for each facility for which information is specified in the information record for the offered service within service offer database 114h, and, if information is specified for more than one facility in the information record for the offered service, the facility fee for each specified facility may be presented in association with a user interface control that is provided to allow the user to select one of the facilities at which to have the primary service performed. Purchasing service 126 can be configured to, based on any optional secondary service and facility selections that are made by the user with respect to an entry for an offered service included in the purchase information section that is being offered as a primary service of a bundled set of services, recalculate and update the price for purchasing the offered service that is presented in the entry for the offered service. In exemplary embodiments, the default initial settings for any optional secondary service and multiple facility selections for a service being offered as a primary service of a bundled set of services and, thereby, the default initial price for purchasing the offered service that is presented in the entry for the offered service, may be based on a selection to purchase each optional secondary service and a selection of the facility having the lowest facility fee.

In the example screen shot depicted in FIG. 3B, each entry for an offered service listed in result listing section 311 includes a first portion 312 presenting information from the account information record within physician profile database 114b of the physician that will perform the service as specified in the information record for the offered service within service offer database 114h (for example, the physician's name, specialty, and profile picture), a second portion 313 presenting information from the account information record of the provider that is offering the service through the system (for example, provider name) and the location at which the offered service will be performed (for example, address and telephone number), and a third portion 314 presenting cost information for purchasing the offered service through application server 116 (for example, the discounted price for the service that is specified in the information record for the offered service within service offer database 114h and a cost savings difference between the discounted price and the regular price for the service when the service is purchased outside of the system from the provider as specified in the information record for the offered service within service offer database 114h), and an option to select to purchase the offered service listed in the entry (for example, via an "Add to Cart" button included within third portion 314). When a user selects the option to purchase an offered service listed in result listing section 311, navigation and search service 124 can be configured to update the session data object for the session with application server 116 that is presently being maintained for the user to include an indication that the user has selected the offered service for purchasing (for example, by including the procedure offer identifier that is maintained within service offer database 114h to uniquely identify the offering of the particular service by the provider).

Figure 3C:
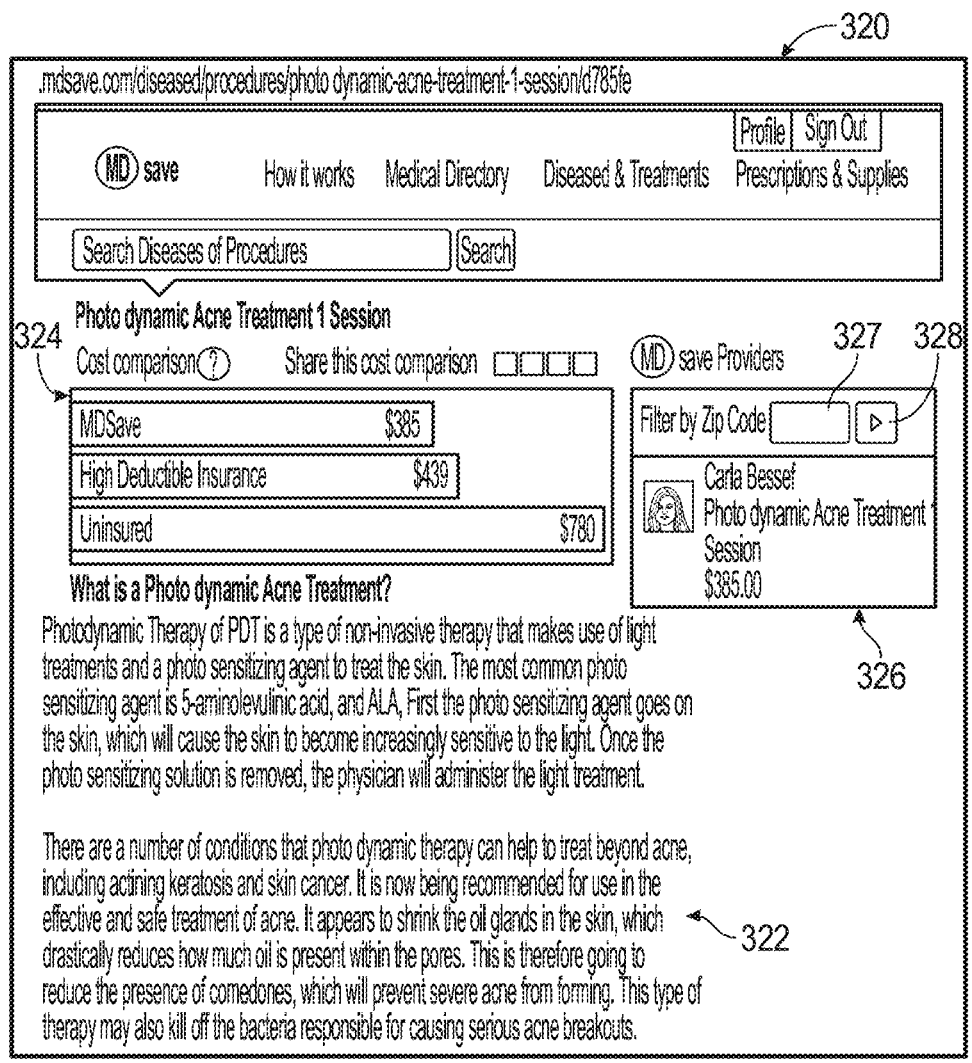

Referring now to FIG. 3C, a screen shot illustrating an example of a GUI provided by a healthcare service information page 320 implemented by navigation and search service 124 for a particular healthcare service is provided. In the illustrated example, healthcare service information page 320 includes a procedure overview section 322, a cost comparison graphic 324, and a provider listing section 326.

The information presented in provider listing section 326 can be generated in a manner similar to the information included in result listing section 311 of example search result listing page 310 depicted in FIG. 3B to present a list of providers offering the particular service within a default search radius (for example, 50 miles) of a location determined by navigation and search service 124. The particular location that is utilized for this purpose may be determined using, for example, a location that is stored within the session data object for the session with application server 116 that is presently being maintained for the user or location information that is gathered by any suitable location determining functionality implemented on the client system to provide a default location entry. In the present example, provider listing section 326 presents an entry for each offered service for which a respective information record is maintained within service offer database 114h that matches the particular service for which healthcare service information page 320 is generated and along with the determined location. Each entry for an offered service listed in provider listing section 326 presents information from the account information record within physician profile database 114b of the physician that will perform the service as specified in the information record for the offered service within service offer database 114h (for example, the physician's name and profile picture) and cost information for purchasing the offered service through application server 116 (for example, the discounted price for the service that is specified in the information record for the offered service within service offer database 114h). In the present example, provider listing section further includes a location entry field 327 that, in conjunction with a "submit" button 328, allows a user to specify a particular location (for example, a city name and/or zip code) and submit a request for navigation and search service 124 to conduct a search and update the information presented in provider listing section 326 to present a list of providers offering the particular service within the default search radius of the newly specified location. Navigation and search service 124 can also be configured to, in response to such a request, update the location that is maintained within the session data object for the session with application server 116 that is presently being maintained for the user.

Figure 3D:

In exemplary embodiments, as further illustrated in FIG. 3D, physician information section 332 can further include additional user interface elements such as a "Leave a review" button 333, a "Request an appointment" button 334, and a map element 335 depicting a mapped location of an office location included within respective account information record that is maintained for the particular physician user in physician profile database 114b (which navigation and search service 124 may be configured to generate by remotely accessing a third-party mapping service). In response to a user selecting "Leave a review" button 333, navigation and search service 124 can be configured to implement suitable user interface controls for allowing the user to post or submit a review of the particular physician to server system 110. In response to receiving such a review, navigation and search service 124 can be configured to, for example, include information pertaining to the review within the respective account information record that is maintained for the particular physician user in physician profile database 114b or send an electronic message to the physician user pertaining to the review, for example, by way of email utilizing the contact information specified in the respective account information record for the physician.

In response to a user selecting "Request an appointment" button 334, navigation and search service 124 can be configured to implement suitable user interface controls for allowing the user to submit a request for scheduling an appointment to the particular physician user (for example, by sending a notification to the physician user by utilizing the contact information specified in the respective account information record for the physician that includes contact information for the user). Navigation and search service 124 may also be configured to implement suitable user interface controls for allowing the user to schedule an appointment with the particular physician user. Navigation and search service 124 may provide this functionality by, for example, accessing a service with which the particular physician user is associated, which may be a service offered by application server 116 or offered by a third-party service provider.

In the present example, as illustrated in FIG. 3D, the information presented in offered procedures section 336 of physician profile page 330 can include a listing of healthcare services offered by the particular physician for purchase through marketplace system 100.

In the illustrated example, physician profile page 330 includes a physician information section 332 and an offered procedures section 336. The information presented in physician information section 332 can be generated based on the information that is included in the respective account information record that is maintained for the particular physician user in physician profile database 114b and may include various items of information relevant to the physician, such as name, practice specialty, office location(s) and hours, a profile picture, contact information, biographical information (such as awards, honors, publications, patient testimonials, and other information that may be of interest to prospective customers accessing the system), URLs or references to websites and social media profiles, and group practice and hospital affiliation(s).

In exemplary embodiments, the user interface implemented by account management service 122 may be further configured to provide user interface controls for requesting authorization for payment of a predetermined fee to gain access to the ability to make prepaid purchases of healthcare services and products offered within marketplace system 100. The payment information input by the user may be an instruction to use the billing information included within the respective account information record established for the user within customer profile database 114a or submission of alternative payment information such as, for example, bank account information, credit or debit card information, or other electronic payment information (such as information for utilizing an account the user has with PayPal or any another entity facilitating payments and money transfers to be made through the Internet), which may be for an account maintained for the user or an account maintained for another person or entity that the user is authorized to utilize for this purpose.

Account management service 122 can be configured to, upon the authorization and appropriate payment information being provided by the user, access a corresponding third-party payment servicing system and utilize the payment information to direct the payment servicing system to transfer the amount for the payment authorized by the user from the account servicer of the user to a financial account maintained by the providers of marketplace system 100. In this regard, the respective account information record established for the user within customer profile database 114a can further include an account status that is managed by account management service 122 for the user indicating whether the user is presently provided with the ability to make prepaid purchases of healthcare services and products offered within marketplace system 100.

Upon a user registering a customer account with server system 110 to establish an account information record within customer profile database 114a and logging into his or her customer account (for example, by accessing a login user interface element or a login screen within the user interface implemented by customer portal 120 to provide the user name and password associated with the account), the user then proceeds with purchasing any offered service or product for which the session data object for the session with application server 116 that is being maintained for the user includes an indication that the user has selected for purchasing. For example, upon the user selecting an option within the user interface implemented by navigation and search services 124 to navigate to a customer purchase page and initiate a purchasing session with purchasing service 126 to purchase one or more of the offered items indicated as having been selected by the user in the session data object in association with the registered customer account for the user.

The purchase information section included within the user interface implemented for the payment page may further include a total price for the purchase that is equal to a sum of the respective price for purchasing the corresponding offered item included for each entry included in the purchasing information section. In exemplary embodiments, purchasing service 126 may be configured to adjust the total price based on any applicable state taxes or any discount codes submitted by the user. In this regard, purchasing service 126 may be further implemented to provide a user interface element allowing a user to submit any application discount codes to application server 116.

For this purpose, the user interface controls implemented within a payment section may include a button that is accessible by the user to provide authorization for the request to be issued to the specified funding source (for example, a "Submit" or "Purchase" button) along suitable user interface elements accessible by the user to input the purchase information specifying the funding source to use for the purchase. The purchase information input by the user may be an instruction to use the billing information included within the respective account information record for the customer account of the user within customer profile database 114a or submission of alternative purchase information such as, for example, bank account information, credit or debit card information, or other electronic payment information (such as information for utilizing an account the user has with PayPal or any another entity facilitating payments and money transfers to be made through the Internet). The purchase information may, for example, specify an account maintained for the user, an account maintained for another person or entity that the user is authorized to utilize for this purpose, or an entity that has arranged to be invoiced and provide reimbursement for purchases of healthcare services and products made by the user within marketplace system 100.

Figure 4A:
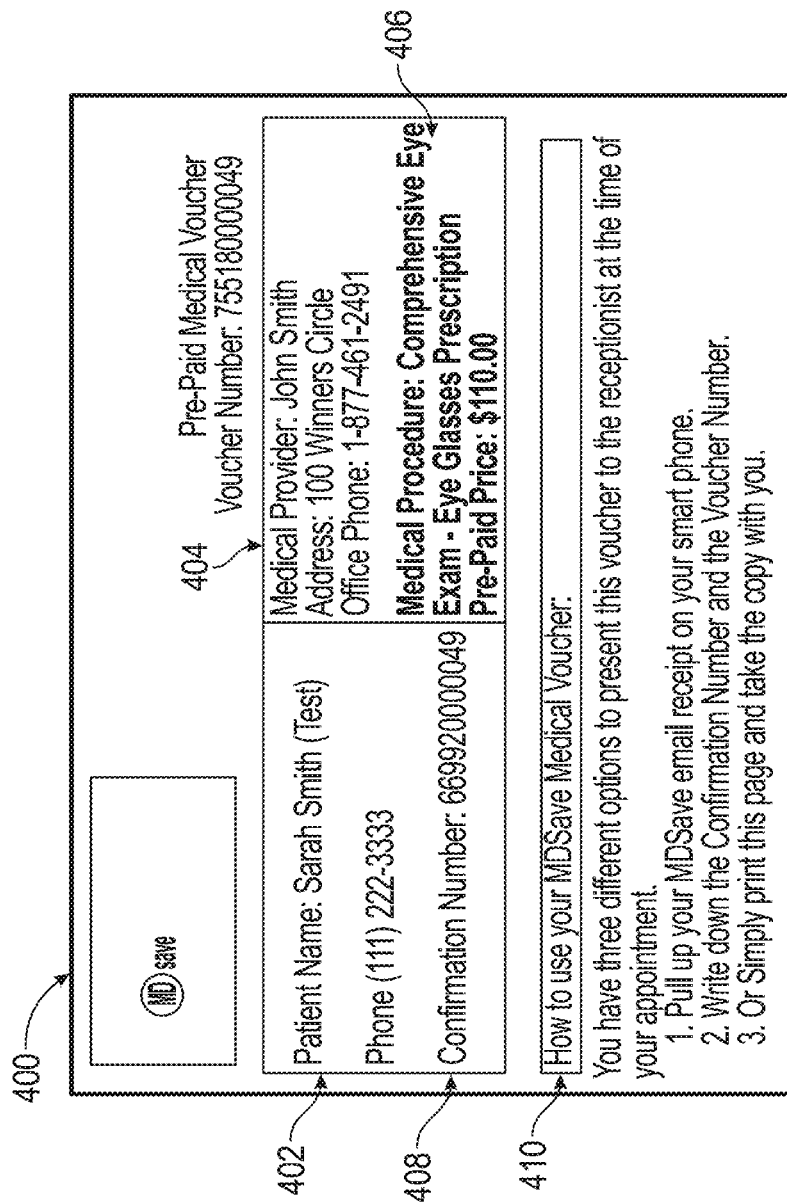
FIG. 4A is an illustration of an example voucher that may be generated within a user interface by functions provided within a customer portal for a purchased service in accordance with exemplary embodiments of the present invention.

Purchasing server 126 can also be configured to, upon processing the payment for the purchase of the offered service, generate a voucher for the customer user within the user interface for the purchased service that can be utilized by the customer user to redeem the purchase and receive the service from the physician specified for the offered service (the providers of marketplace system 100 can have pre-arranged agreements with providers registered with the system that the providers will agree to honor such vouchers generated by purchasing server 126 for purchased services). An example of such a voucher is illustrated in FIG. 4A. As depicted in the example, example voucher 400 can be generated to include identifying information for the customer user 402, identifying and contact information for the physician specified for the offered service 404, a description of the purchased service 406, a confirmation number 408 for the purchase, which may be generated by purchasing server 126 based on the unique transaction identifier that is included in the respective information record for the purchase that is maintained within transaction information database 114k, and instructions for redeeming the voucher 410. The confirmation number may also be provided in the electronic confirmation message to the customer user and electronic notifications to the physician user that will be performing the service and the provider user for the offered service sent by purchasing system 126 to the customer user. The voucher can be presented to the user within the user interface, for example, as printable and/or machine readable form.

Purchasing server 126 can be configured to, upon processing the payment for the purchase of the offered service that is being offered as a primary service in conjunction with a bundled set of services, navigate the user interface to a purchase confirmation page and send an electronic confirmation message to the customer user and electronic notifications to each physician that will perform a service of the bundled set of services and the provider user for the offered service (as specified according to the information record for the offered service within service offer database 114h), for example, by way of email utilizing the contact information specified in the respective account information records for the customer, the physicians, and the provider for the offered service. Purchasing server 126 can also be configured to generate a respective information record for the completed purchase with corresponding information within transaction information database 114k, which initially indicates that the purchase has not yet been redeemed with respect to the primary service, each secondary service, and any facility specified for the purchased offered service.

Purchasing server 126 can also be configured to, upon processing the payment for the purchase of the offered service that is being offered as a primary service in conjunction with a bundled set of services, generate a voucher for the customer user within the user interface for the purchased service that can be utilized by the customer user to redeem the purchase and receive the service from the corresponding physician specified for each of the services of the bundled set of services (the providers of marketplace system 100 can have pre-arranged agreements with providers registered with the system that the providers will agree to honor such vouchers generated by purchasing server 126 for purchased services). An example of such a voucher for a bundled set of services is illustrated in FIG. 4B. As depicted in the example, example voucher 400 can be generated to include identifying information for the customer user 402, identifying and contact information for each physician specified for a service and any facility included in the offered service 404, a description of each service of the purchased service 406, a confirmation number 408 for the purchase, which may be generated by purchasing server 126 based on the unique transaction identifier that is included in the respective information record for the purchase that is maintained within transaction information database 114k, and instructions for redeeming the voucher 410. The confirmation number (or any other suitable redemption information such as a one- or two-dimensional bar code, a QR code, or any other form of machine-readable information) may also be provided in the electronic confirmation message to the customer user and electronic notifications to the physician user that will be performing the service and the provider user for the offered service sent by purchasing system 126 to the customer user. The voucher can be presented to the user within the user interface, for example, as printable and/or machine-readable form.

Upon the user indicating an intention to register as a physician user, the user will be able to initiate a registration session with account management service 131 to register a physician account with server system 110. Account management service 131 may be configured, for example, to implement a user interface that includes a series of pages with user interface controls accessible by the user to guide the user through the account registration process and prompt the user to input various types of information or media to be maintained by database server 112 within a respective account information record that is established for the user within physician profile database 114b such as, for example, name, practice specialty, office location(s) and hours, a profile picture, contact information (such as an email address and/or a telephone number), biographical information (such as awards, honors, publications, patient testimonials, and other information that can be helpful for marketing the physician to customers accessing the system), URLs or references to web sites and social media profiles, compensation information (indicating a financial account for receiving payment for purchases of services offered by the physician via the system), information pertaining to outside facilities that are used for particular services performed by the physician (for example, information pertaining to particular hospitals or clinics such as name, address, contact information, facility fee, and compensation information indicating a financial account that is used by the facility for receiving a facility fee), and any other suitable identifying or descriptive information. The user interface may also be implemented by account management service 131 to prompt the user for any group affiliation codes or hospital affiliation codes.

Procedure management service 133 may be configured, for example, to implement a user interface that includes a series of pages with user interface controls accessible by the user to guide the user through the service offering process and prompt the user to input various types of information to be maintained by database server 112 within a respective information record that is established in association with the unique physician account identifier for the physician within service offer database 114h. Upon the user indicating an intention to offer a healthcare service for purchase (for example, by selecting a "Offer Service" tab within the practice group account page implemented by provider portal 130), the user will be able to initiate a service offering with procedure management service 133 to offer a healthcare service performed by affiliated physicians for purchase via server system 110. For example, the user may be provided with a drop-down menu providing a list of selectable medical specialties and, upon selecting a particular medical specialty, the user can be presented with a list of selectable healthcare services for which an information record for the service is maintained within available services database 114g in association with the specialty.

Upon the user selecting a particular service from this list, procedure management service 133 can assist the user with offering the service for purchase and establish the respective information record for the offered service within service offer database 114h. In particular, procedure management service 133 can present the user with a selectable list of the physician users affiliated with the practice group from which the user can submit an indication one or more of the affiliated physicians with which to offer the service in conjunction with the practice group account. For each selected affiliated physician user, procedure management service 133 can establish a respective information record for the offered service within service offer database 114h by populating the information record with the unique procedure identifier for the information record within available services database 114g for the selected service, the unique account identifier for the account information record for the practice group within physician profile database 114b as the provider that is offering the service through the system, the unique account identifier for the account information record for the physician user within physician profile database 114b as the physician user will perform the service, a location at which the service will be performed, the unique account identifier for the account information record (within physician profile database 114*b*, practice group profile database 114*c*, or hospital system profile database 114*d*) of the provider for which payment for the service when purchased through the system is to be directed (or, alternatively, other financial account information) as indicated by user input received from the practice group administrator, a payment amount to be transferred to the provider or other financial account for which payment for the service is to be directed as specified by user input received from the practice group administrator, a discounted price for purchasing the service within marketplace system 100 (which may be calculated, for example, by adding a negotiated commission fee to the payment amount specified by the practice group administrator), a regular price for the service when the service is purchased outside of the system, additional descriptive information that may be provided via input received from the practice group administrator, a procedure offer identifier, and any other suitable information (such as an indication that the service is required to be performed at an outside facility and relevant facility information as specified by user input received from the practice group administrator).

In exemplary embodiments, procedure management service 133 can also assist the practice group administrator with offering services for purchase as a bundled set of services within marketplace system 100 and establishing the respective information record for the service offered as a bundled set of services within service offer database 114*h*. In particular, procedure management service 133 can present the user with an option to indicate that a particular service selected by the user should be offered as a primary service of a bundled set of services or, alternatively, the information record for a particular service selected by the user that is maintained within available services database 114*g* can include an indication that the service can be offered by providers within marketplace system 100 as a primary service of a bundled set of a plurality of services.

For a selected service for which such an indication is provided, procedure management service 133 may be configured, for example, to implement user interface controls accessible by the user to guide the user through the process for offering the selected service as a primary service of a bundled set of services and prompt the user to input various types of information to populate a respective information record that is established in association with the unique practice group account identifier for the practice group within service offer database 114*h*. Procedure management service 133 can first present the user with a selectable list of the physician users affiliated with the practice group from which the user can submit an indication of affiliated physicians with which to offer the primary service in conjunction with the practice group account and then populate the information pertaining to the primary service in the information record with the unique procedure identifier for the information record within available services database 114*g* for the selected service, the unique account identifier for the account information record for the practice group within physician profile database 114*b* as the provider that is offering the primary service through the system, the unique account identifier for the account information record for the physician user within physician profile database 114*b* as the physician user will perform the primary service, a location at which the primary service will be performed, the unique account identifier for the account information record (within physician profile database 114*b*, practice group profile database 114*c*, or hospital system profile database 114*d*) of the provider for which payment for the primary service when purchased through the system is to be directed (or, alternatively, other financial account information) as indicated by user input received from the practice group administrator, a payment amount to be transferred to the provider or other financial account for which payment for the primary service is to be directed as specified by user input received from the practice group administrator, a discounted price for purchasing the primary service within marketplace system 100 (which may be calculated, for example, by adding a negotiated commission fee to the payment amount for the primary service specified by the practice group administrator), a regular price for the primary service when the primary service is purchased outside of the system, additional descriptive information that may be provided via input received from the practice group administrator, a procedure offer identifier, and any other suitable information.

Procedure management service 133 can then receive an indication, either from the information record for a particular service selected by the user that is maintained within available services database 114*g* or through selections made by the user of services offered by affiliated physicians for which an information record for the service is maintained within available services database 114*g*, of one or more secondary services to be included in the bundled set of services. Procedure management service can then populate the information pertaining to each secondary service in the information record with the unique procedure identifier for the information record within available services database 114*g* for the secondary service (or the secondary procedure identifier that is included in the available services database 114*g* to uniquely identify the particular secondary service in association with the unique procedure identifier for the offered primary service where the information record for the primary service being offered in the available services database 114*g* includes an indication that the service is offered as a primary service of a bundled set of services), the unique physician account identifier for the account information record within physician profile database 114*b* of the physician user that will perform the secondary service, a location at which the service will be performed, the unique account identifier for the account information record (within physician profile database 114*b*, practice group profile database 114*c*, or hospital system profile database 114*d*) of the provider for which payment for the primary service when purchased through the system is to be directed (or, alternatively, other financial account information) as indicated by user input received from the practice group administrator, a payment amount to be transferred to the provider or other financial account for which payment for the secondary service is to be directed as specified by user input received from the practice group administrator, a discounted price for purchasing the secondary service within marketplace system 100 (which may be calculated, for example, by adding a negotiated commission fee to the payment amount for the secondary service specified by the practice group administrator), a regular price for the secondary service when the secondary service is purchased outside of the system, and an indication of whether performance of the secondary service is optional or required in association with performance of the primary service. Procedure management service can further populate the information in the information record with an indication of whether the primary service is to be performed at an outside facility and, if the primary service is to be performed at an outside facility, items of information pertaining to each of one or more facilities that may be used to perform the primary service such as, for example, name, address, contact information, facility fee, and compensation information indicating a financial account that is used by the facility for receiving a facility fee (as specified by user input received from the practice group administrator).

Upon the user indicating an intention to request payment for a purchased service that have been performed (for example, by selecting a "Voucher Processing" tab within the physician account page implemented by provider portal 130), the user will be able to initiate a voucher processing session with transaction processing service 136. In particular, transaction processing service 136 may be configured, for example, to implement a voucher history page within the user interface that presents information relevant to the physician user for a list of purchases for which the respective information record for the purchase that is maintained within transaction information database 114k includes the unique physician account identifier for the physician user within physician profile database 114b as the physician user that is designated as performing a service included the purchase (for example, a primary or secondary service for a bundled set of services). The relevant information for each listed purchase may include, for example, the voucher confirmation number or redemption code, name and contact information for the customer user, a description of the service the physician user is designated as performing for the purchase, a purchase date, and a voucher redemption status. Such a voucher history page may also be accessed in association with the user account for the physician user to verify vouchers presented by customers requesting to have a service performed in association with a voucher.

Transaction processing service 136 can be configured to, upon such a verification being submitted, initiate a transfer of the payment amount specified for the service performed by the physician user in service offer database 114h and held in the financial account maintained by the providers of marketplace system 100 to the financial account listed for receiving the payment amount for service that is specified in service offer database 114h. Additionally, if the service performed by the physician is a primary service of a bundled set of services for which a particular outside facility that has been selected for performing the primary service, transaction processing service 136 can be configured to initiate a transfer or otherwise direct a disbursement of the facility fee specified for the service performed by the physician user in service offer database 114h and held in the financial account maintained by the providers of marketplace system 100 to the financial account for the facility that is indicated by the compensation information for the facility. Transaction processing service 136 can be configured to update the indication of whether the purchase has been redeemed with respect to that particular service (and facility if one is associated with the service in the purchase) and include the redemption date for that particular service in the information record for the purchased service that is maintained within transaction information database 114k. In addition, transaction processing service can further be configured to send electronic notifications to the customer user, the physician user, and the provider user for the offered service (as specified according to the corresponding information records within service offer database 114h and transaction information database 114k), for example, by way of email utilizing the contact information specified in the respective account information records for the customer, the physician, and the provider for the offered service. Upon the user indicating an intention within the physician account page implemented by provider portal 130 to access various account management functions, the user can access various user interface elements provided by account management service 131 to, for example, manage personal and payment or purchase information, manage information pertaining to services offered for purchase by the physician user, manage group practice and hospital affiliations, and view a history of transactions performed for services offered for purchase by the physician user within server system 110 (and relevant information for each purchase including voucher redemption status).

The voucher history page can also provide a user interface element in association with each of the listed purchases for which the voucher redemption status for the service the physician user is designated as performing indicates the service has not been performed that is accessible by the physician user to submit a verification to application server 116 that the physician user has performed the service for the customer user in accordance with the purchase.

Referring again to FIG. 2, in exemplary embodiments, when a user operating a client system to access application server 116 via a corresponding client application executing on the client system initiates a registration with server system 110 and specifies an intention to register as a practice group administrator (for example, via a user interface element on any page implemented by navigation and search service 124), the user will be able to initiate a registration session with account management service 131 to register a practice group account with server system 110. Account management service 131 may be configured, for example, to implement a user interface that includes a series of pages with user interface controls accessible by the user to guide the user through the account registration process and prompt the user to input various types of information or media to be maintained by database server 112 within a respective account information record that is established for the user within practice group profile database 114c such as, for example, practice group name, location and hours, contact information (such as an email address and/or a telephone number), URLs or references to websites and social media profiles for the practice group, information pertaining to outside facilities that are used for particular procedures by physicians affiliated with the practice group, (for example, information pertaining to particular hospitals or clinics such as name, address, contact information, facility fee, and compensation information indicating a financial account that is used by the facility for receiving a facility fee), compensation information (indicating a financial account for receiving payment for purchases of services that are performed by affiliated physicians via the system), and any other suitable identifying or descriptive information.

The voucher history page can also provide a user interface element in association with each of the listed purchases for which the voucher redemption status for the service indicates the service has not been performed that is accessible by the practice group user to submit a verification to application server 116 that the affiliated physician user specified as performing the service has performed the service for the customer user in accordance with the purchase.

In exemplary embodiments, when a user operating a client system to access application server 116 via a corresponding client application executing on the client system initiates a registration with server system 110 and specifies an intention to register as a hospital system administrator (for example, via a user interface element on any page implemented by navigation and search service 124), the user will be able to initiate a registration session with account management service 131 to register a hospital system account with server system 110. Account management service 131 may be configured, for example, to implement a user interface that includes a series of pages with user interface controls accessible by the user to guide the user through the account registration process and prompt the user to input various types of information or media to be maintained by database server 112 within a respective account information record that is established for the user within hospital system profile database 114d such as, for example, contact information (such as an email address and/or a telephone number), information pertaining to outside facilities that can be used for particular procedures by physicians affiliated with the hospital system (for example, information pertaining to particular hospitals or clinics such as name, address, contact information, facility fee, and compensation information indicating a financial account for that is used by the facility for receiving a facility fee), compensation information (indicating a financial account for receiving payment for purchases of services performed by affiliated physicians via the system), and any other suitable identifying or descriptive information.

In exemplary embodiments, the functionality that is provided within provider portal 130 for users of hospital system accounts can vary in certain respects from the functionality that may be provided within provider portal 130 for users of practice group accounts. For example, with respect to physicians that are affiliated with the hospital system account, users of hospital system accounts may only be provided with access rights (for example, to view, modify, and specify in a service being offered by the hospital system for purchase) to services offered for purchase by affiliated physician users that have been specified by the physician users as being hospital procedures with respect to the physician accounts. Hospital system users may also be provided with functionality to, as an alternative to selecting a service by accessing a list of selectable medical specialties when initiating a service offering with procedure management service 133 to offer a service performed by affiliated physicians for purchase via server system 110, submit a search query for a service by inputting descriptive terms or a medical code number that is used to identify the service (for example, according to the CPT code set) or access a list of affiliated physicians and, upon selecting a particular affiliated physician from the list, be presented with a list of selectable healthcare services for which an information record for the service is maintained within service offer database 114h that indicates the selected physician as the physician that will perform the service.

In addition, because a hospital system may be more likely to offer a higher quantity of services for purchase as a bundled set of services within marketplace system 100 than other types of provider users, the functionality implemented by provider portal 130 within the user interface for allowing a user of a hospital system account to manage information pertaining to services offered by the hospital system for purchase and to view a history of transactions performed for services offered for purchase by the hospital system within server system 110 may include an additional user interface element that is accessible by a user for the hospital system account manage and view information pertaining to only services that are offered by the hospital system as a bundled set of services.

Figure 5:
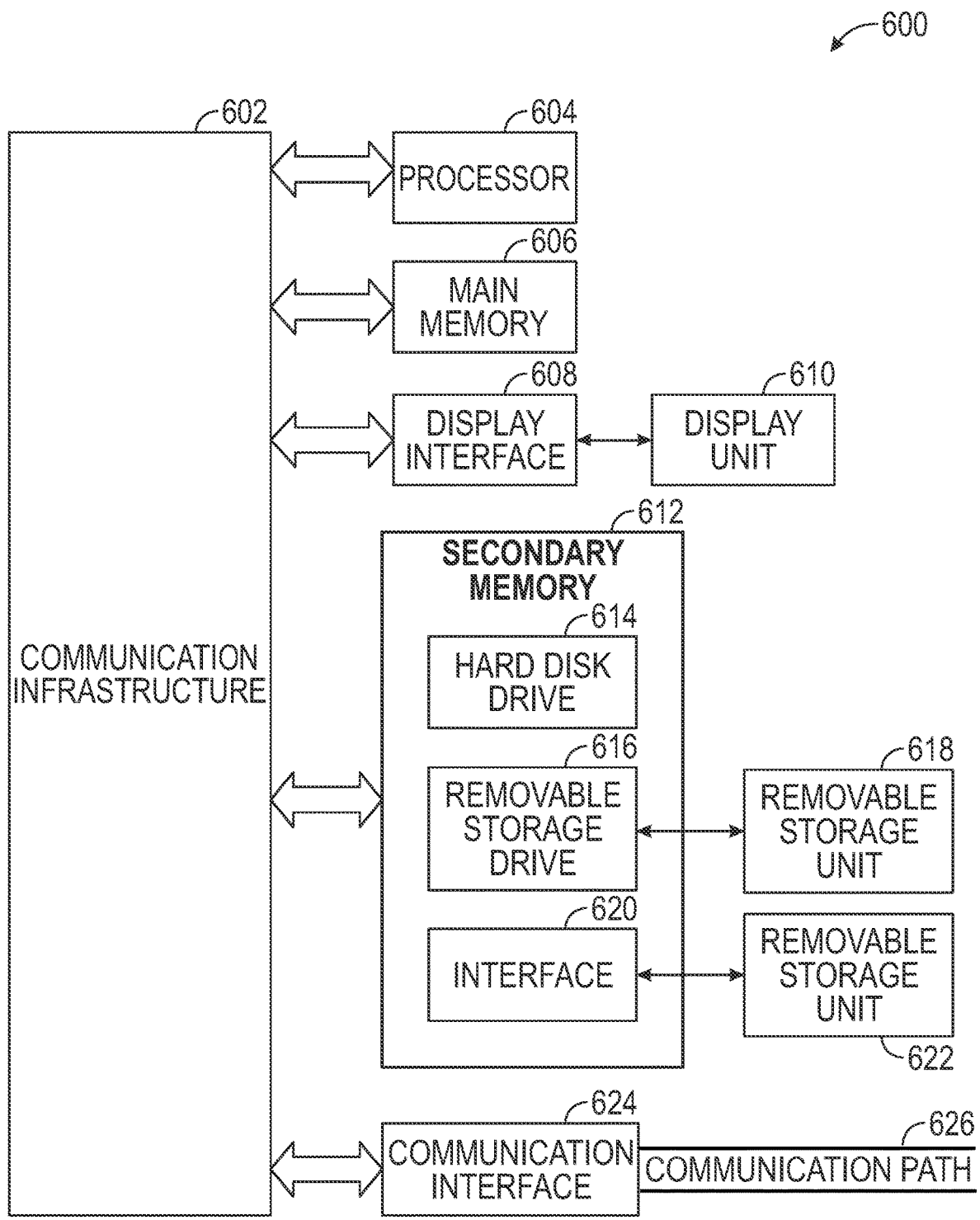
FIG. 5 is a block diagram of an exemplary computer system that can be used for implementing exemplary embodiments of the present invention.

FIG. 5 is a block diagram of an exemplary computer system 600 that can be used for implementing exemplary embodiments of the present invention. Computer system 600 includes one or more processors, such as processor 604. Processor 604 is connected to a communication infrastructure 602 (for example, a communications bus, cross-over bar, or network). Various software embodiments are described in terms of this exemplary computer system. After reading this description, it will become apparent to a person of ordinary skill in the relevant art(s) how to implement the invention using other computer systems and/or computer architectures.

Exemplary computer system 600 can include a display interface 608 that forwards graphics, text, and other data from the communication infrastructure 602 (or from a frame buffer not shown) for display on a display unit 610. Computer system 600 also includes a main memory 606, which can be random access memory (RAM), and may also include a secondary memory 612. Secondary memory 612 may include, for example, a hard disk drive 614 and/or a removable storage drive 616, representing a floppy disk drive, a magnetic tape drive, an optical disk drive, etc. Removable storage drive 616 reads from and/or writes to a removable storage unit 618 in a manner well known to those having ordinary skill in the art. Removable storage unit 618, represents, for example, a floppy disk, magnetic tape, optical disk, etc. which is read by and written to by removable storage drive 616. As will be appreciated, removable storage unit 618 includes a computer usable storage medium having stored therein computer software and/or data.

In exemplary embodiments, secondary memory 612 may include other similar means for allowing computer programs or other instructions to be loaded into the computer system. Such means may include, for example, a removable storage unit 622 and an interface 620. Examples of such may include a program cartridge and cartridge interface (such as that found in video game devices), a removable memory chip (such as an EPROM, or PROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between the computer system and external devices. Examples of communications interface 624 may include a modem, a network interface (such as an Ethernet card), a communications port, a PCM-CIA slot and card etc. Software and data transferred via communications interface 624 are in the form of signals which may be, for example, electronic, electromagnetic, optical, or other signals capable of being received by communications interface 624. These signals are provided to communications interface 624 via a communications path (that is, channel) 626. Channel 626 carries signals and may be implemented using wire or cable, fiber optics, a phone line, a cellular phone link, an RF link, and/or other communications channels.

In this document, the terms "computer program medium," "computer usable medium," and "computer readable medium" are used to generally refer to media such as main memory 606 and secondary memory 612, removable storage drive 616, a hard disk installed in hard disk drive 614, and signals. These computer program products are means for providing software to the computer system. The computer readable medium allows the computer system to read data, instructions, messages or message packets, and other computer readable information from the computer readable medium. The computer readable medium, for example, may include non-volatile memory, such as Floppy, ROM, Flash memory, Disk drive memory, CD-ROM, and other permanent storage. It can be used, for example, to transport information, such as data and computer instructions, between computer systems. Furthermore, the computer readable medium may comprise computer readable information in a transitory state medium such as a network link and/or a network interface including a wired network or a wireless network that allow a computer to read such computer readable information.

Computer programs (also called computer control logic) are stored in main memory 606 and/or secondary memory 612. Computer programs may also be received via communications interface 624. Such computer programs, when executed, can enable the computer system to perform the features of exemplary embodiments of the present invention as discussed herein. In particular, the computer programs, when executed, enable processor 604 to perform the features of computer system 600. Accordingly, such computer programs represent controllers of the computer system.

Figure 6:
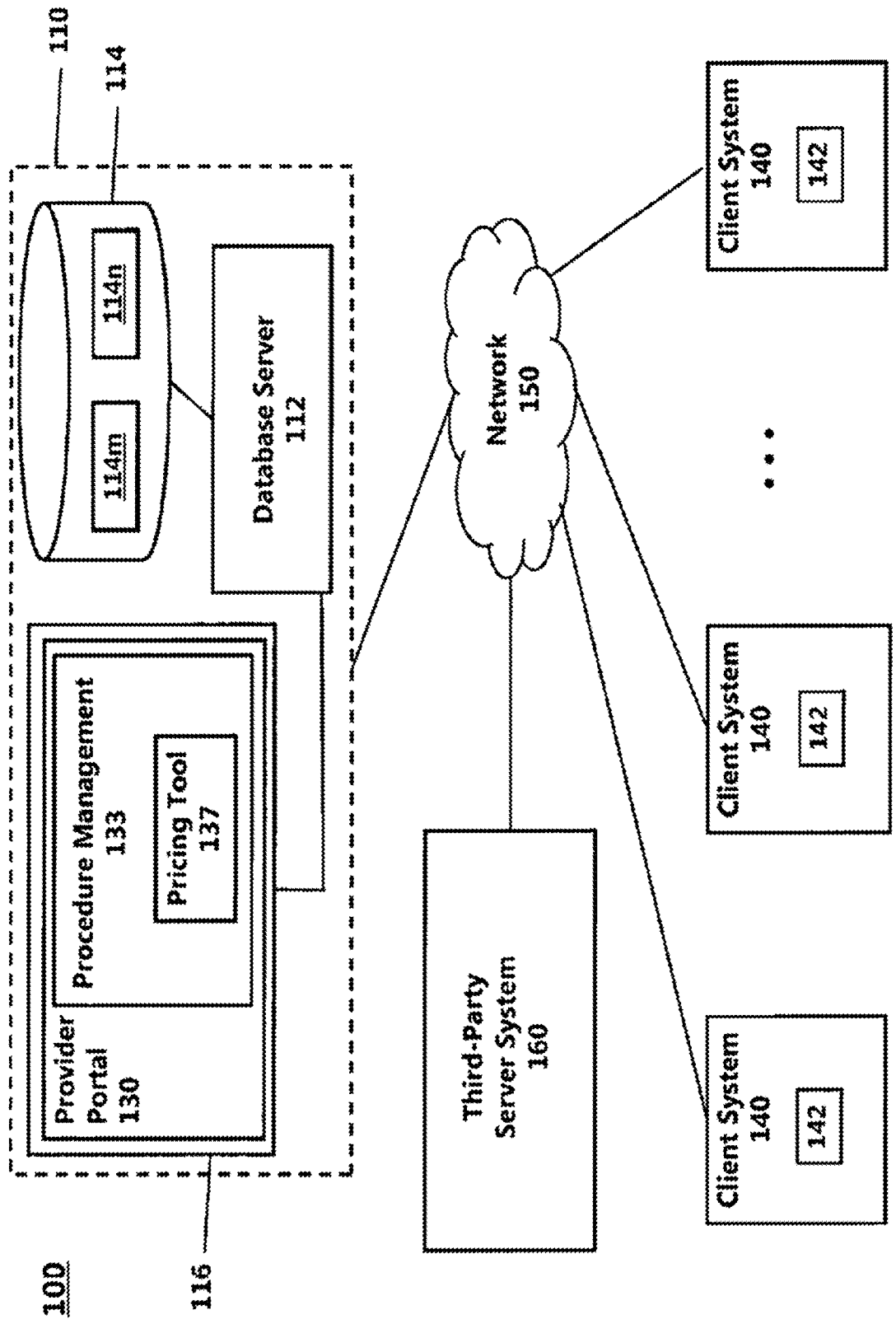
FIG. 6 is a schematic diagram illustrating a second example network architecture for a healthcare marketplace system that can be configured to implement exemplary embodiments of the present invention.

Referring now to FIG. 6, a schematic diagram illustrating an example network architecture for healthcare marketplace system 100 within which an exemplary embodiment of a provider pricing tool in accordance with the present invention is implemented. It should of course be understood that FIG. 6 is intended as an example, not as an architectural limitation for different embodiments of the present invention, and therefore, the particular elements depicted in FIG. 6 should not be considered limiting with regard to the environments within which exemplary embodiments of the present invention may be implemented.

In the example illustrated in FIG. 6, the particular components that are utilized for providing the provider pricing tool are integrated within system 100 in conjunction with the components of the system as described above with reference to the exemplary embodiments illustrated FIGS. 1 and 2. More specifically, the pricing tool 137 is shown in FIG. 6 as being implemented within procedure management service 133 included within provider portal 130, and data store 114 further comprises a service pricing information database 114m and a cost adjustment information database 114n that are maintained by database server 112, are accessed by application server 116 via database services provided at a front end by database server 112, and retain information collected from a variety of data sources that is utilized in providing the services offered via the provider pricing tool within the network service provided by the application server, as described below in greater detail.

In the present exemplary embodiments, for use in conjunction with the physician service pricing information within service pricing information database 114m, a corresponding set of cost adjustment data can be compiled and maintained within cost adjustment information database 114n that can be applied to account for geographical variances in physician costs. The cost adjustment data can, for instance, be compiled from and/or determined based upon the Geographic Practice Cost Indices (GPCIs), which is used along with RVUs in Medicare Physician Fee Schedule (PFS) provided by CMS to determine allowable payment amounts for medical procedures in a manner that reflects geographical variations in practice cost. GPCIs are used to help standardize the differences in resource costs incurred in operating a private medical practice across geographic areas when those costs are compared with the national average costs for the physician work, practice expense, and malpractice insurance components of the fee schedule.

More specifically, the CMS has established a GPCI for every Medicare payment locality for each of the three relative value unit components for a procedure (that is, the RVUs for work, practice expense, and malpractice), and the GPCIs are applied in the calculation of a fee schedule payment amount by multiplying the RVU for each component times the GPCI for that component. A listing of the current GPCI locality structure, including state, locality area (and when applicable, counties assigned to each locality area), and the corresponding GPCIs for each locality, can be obtained from the CMS website, and this information can be compiled and maintained within cost adjustment information database 114n by a back-end administrator of server system 110. In exemplary embodiments, a specific cost adjustment factor can be determined based on the GPCI information for each designated locality area and maintained within cost adjustment information database 114n. For example, a standard rate adjustment factor for each designated locality area can be determined by calculating an average (or any other suitable aggregate or composite-based) factor by which the corresponding GPCIs for the locality impact the standard national rate derived for each service. As another example, such a standard rate adjustment factor for each designated locality area can be derived directly from the Geographic Adjustment Factor (GAF) that is determined for the locality by CMS. The GAF for each designated locality area is calculated as the weighted average of the three GPCIs, where the weights are the percentage of RVUs nationally made up by the PW, PE, and MP RVUs.

In another example, for each service for which the information record within service pricing information database 114m includes an indication that the service is offered as a primary service of a bundled set of services along with an indication that the primary service is required to be performed at an outside facility, the respective pricing information that is included in the information record for the use of the outside facility can be determined by whether the use of the outside facility is classified as a facility outpatient service or a facility inpatient service. For instance, for each facility outpatient service, the respective pricing information that is included in the information record for the use of the outside facility can be obtained from the APC price data that is maintained in association with CPT or HCPCS procedure codes by CMS. CMS assigns individual services classified according to HCPCS codes to APCs based on similar clinical characteristics and similar costs. Thus, APCs are essentially line-level fee schedules in which each HCPCS code for a service is assigned to one of hundreds of individual APCs, and for almost every APC, the fee is determined by multiplying a prospectively established scaled relative weight for the service's clinical APC by a conversion factor (CF) to arrive at a national unadjusted payment rate for the APC.

Accordingly, in exemplary embodiments, for each service for which a respective information record is maintained within service pricing information database 114m and a corresponding APC is provided by CMS, the corresponding national unadjusted payment rate for the facility outpatient service can be included in the set of pricing information of the respective information record for the service within service pricing information database 114m.

In the present exemplary embodiment, for use in conjunction with the facility outpatient service pricing information within service pricing information database 114m discussed above, a corresponding set of cost adjustment data can be compiled and maintained within cost adjustment information database 114n that can be applied to account for geographic differences. The cost adjustment data for the facility outpatient service pricing information can, for instance, be compiled from and/or determined based upon the facility wage index that is maintained by the CMS.

In the present exemplary embodiment, for use in conjunction with the facility inpatient service pricing information within service pricing information database 114*m* discussed above, a corresponding set of cost adjustment data can be compiled and maintained within cost adjustment information database 114*n* that can be applied to account for geographic differences.

Similar to the example discussed above with regard to the cost adjustment data for the facility outpatient service pricing information, the cost adjustment data for the facility inpatient service pricing information can, for instance, be compiled from and/or determined based upon the facility wage index that is maintained by the CMS. As noted above, in exemplary embodiments, the facility wage index information can be obtained from CMS and maintained within cost adjustment information database 114*n*.

In this regard, it should be noted that certain services for which the respective information record within service pricing information database 114*m* includes an indication that the service is offered as a primary service of a bundled set of services along with an indication that the primary service is required to be performed at an outside facility may facilitate a mapping of the use of the outside facility to both facility outpatient service price data and facility inpatient service price data. In exemplary embodiments, for such services, a back-end administrator of server system 110 can make a determination of which set of facility price data is more suitable to include in the set of pricing information of the information record. For example, such a determination may be based upon whether the particular service is more typically performed as a facility outpatient service or a facility inpatient service. In alternative exemplary embodiments, for each service for which the respective information record within service pricing information database 114*m* includes an indication that the service is offered as a primary service of a bundled set of services along with an indication that the primary service is required to be performed at an outside facility for which the use of the outside facility can be mapped to both facility outpatient service price data and facility inpatient service price data, respective information records can be maintained for the service as an outpatient facility service and for the service as an inpatient facility service within service pricing information database 114*m*.

In this regard, anesthesia time is a continuous time from the start of anesthesia to the end of an anesthesia service, and one-time unit corresponds to a 15-minute interval, or fraction thereof, starting from the time the physician begins to prepare the patient for induction and ending when the patient may safely be placed under post-operative supervision and the physician is no longer in personal attendance. The conversion factors are listed by the CMS according to locality. Thus, the conversion factor in the formula listed above will correspond to the locality of the performing provider.

In exemplary embodiments, to access the functionality provided by pricing tool 137, a provider user, upon registering a provider account with server system 110 (for example, a physician, practice group, or hospital system account) to establish an account information record within the corresponding profile database maintained within data store 114 and logging into his or her physician account, the user may be directed to a provider account page implemented by provider portal 130 that provides a set of user interface controls that can be accessed by the user to access functionality provided by procedure management service 133 to offer healthcare services for purchase by customer users registered with the system. As noted above, in the present exemplary embodiment, the accessible functionality provided by procedure management service 133 in this regard includes the functionality provided by pricing tool 137.

In particular, upon the provider user indicating an intention to utilize pricing tool in conjunction with offering healthcare services for purchase via server system 110 (for example, by selecting a "Service Pricing Tool" tab within the provider account page implemented by provider portal 130), the user will be directed to an interactive service pricing page with information that is generated based on the information maintained in the respective information record for the provider within the corresponding profile database maintained within data store 114 and the respective information records for healthcare services that are maintained in service pricing information database 114*m*. Price setting tool 137 may be configured, for example, to implement the interactive service pricing page to provide the provider user with detailed pricing information and recommended rates for services that may be offered by the provider for purchase via server system 110, as well as various user interface controls accessible by the user to perform adjustments to the recommended rates as desired.

FIG. 7A is a screen shot illustrating a first example of a graphical user interface provided by such a service pricing page 700 for a user accessing provider portal 130 in association with a registered hospital system account. In the example illustrated in FIG. 7A, the user interface provided at service pricing page 700 includes a medical specialty drop-down menu 702, a locality adjustment section 704, a recommended rate adjustment section 706, a detailed pricing information section 708, and a set of selectable buttons 710*a* ("Email Prices"), 710*b* ("Save Changes"), and 710*c* ("Take Live"), the use of which will be described in greater detail below. Drop-down menu 702 provides a list of selectable medical specialties (for example, orthopedics, general surgery, cardiac imaging, etc.), and pricing tool is implemented to, in response to the user selecting a particular medical specialty using drop-down menu 702, configure the user interface options and populate the information displayed within locality adjustment section 704, recommended rate adjustment section 706, and detailed pricing information section 708 in accordance with the selected medical specialty and further based on information maintained in the respective information record for the provider that is maintained within hospital system profile database 114*d*, information that is maintained in the respective information records for each service indicated as being commonly associated with the selected medical specialty within service pricing information database 114*m*, and information maintained within cost adjustment information database 114*n*, which, as discussed above, can be accessed by pricing tool 137 via database services provided at a front end by database server 112.

For instance, in the example screen shot illustrated in FIG. 7A, the user has selected "Radiology" from medical specialty drop-down menu 702, and pricing tool 137 has, in response to this selection, configured the user interface options and populated the information displayed within locality adjustment section 704, recommended rate adjustment section 706, and detailed pricing information section 708 in accordance with the selection of "Radiology" from drop-down menu 702. More specifically, as shown in FIG. 7A, locality adjustment section 704 has been configured to include a physician locality section and a facility section in response to the selection of "Radiology" from drop-down menu 702. The physician locality section is provided for making pricing adjustments based on the locality of a physician that is affiliated with the hospital system and would be performing the radiology services being priced. The facility section is included within locality adjustment section 704 in response to pricing tool 137 recognizing that the respective information records for services indicated as being commonly associated with the selected medical specialty of radiology within service pricing information database 114*m* include information records having an indication that the service is a primary service of a bundled set of services that is required to be performed at an outside facility and is provided for making pricing adjustments based on the facility that is affiliated with the hospital system at which the radiology services being priced would be performed.

In the present example, the physician locality section includes a physician location field 704*a* and a physician location rate field 704*b*, and the facility section includes a facility field 704*c* and a facility rate field 704*d*. The physician location field 704*a* is for receiving and displaying an entry specifying the location of a physician that would be performing the services indicated as being commonly associated with the selected medical specialty of radiology within service pricing information database 114*m*, and the physician location rate field 704*b* is configured to provide a rate adjustment factor for the pricing information included in detailed pricing information section 708 for the services indicated as being commonly associated with radiology. In exemplary embodiments, pricing tool 137 can be configured to derive an initial physician location entry based on the location associated with physician affiliation(s) included in hospital system profile database 114*d* and include this derived physician location entry as a default value within physician location field 704*a*. Physician location rate field 704*b* is provided for receiving and displaying a geographic adjustment rate for physician services that, by default, is derived based on information maintained in cost adjustment information database 114*n* and provided by pricing tool 137 in correspondence with the physician location entry that is currently specified within physician location field 704*a*. More particularly, in exemplary embodiments, pricing tool 137 can be configured to access the physician rate cost adjustment data in cost adjustment information database 114*n* that corresponds to the physician location entry that is currently specified within physician location field 704*a* (for example, a standard rate adjustment factor determined for a designated locality area that encompasses the specified physician location entry) and derive a corresponding geographic adjustment rate that is displayed as a default value within physician location rate field 704*b*.

In the present example, pricing tool 137 is further configured to allow the provider user accessing service pricing page 700 to proceed to enter text corresponding to a desired location of the physician that would perform the services associated with the selected medical specialty within physician location field 704*a*. In this regard, pricing tool 137 may be configured to require that the text entered by the user in physician location field 704*a* correspond to a particular locality area for which corresponding physician rate adjustments are maintained in cost adjustment information database 114*n*.

The list of suggested physician locations provided by pricing tool 137 can further include an option for the user to select a standard, national physician rate rather than a particular geographic location. In response to a specification of a new physician location within physician location field 704*a*, pricing tool 137 can be configured to dynamically access the physician rate cost adjustment data in cost adjustment information database 114*n* that corresponds to the newly-specified physician location entry that is currently specified within physician location field 704*a* and derive a corresponding geographic adjustment rate that is displayed as the current value within physician location rate field 704*b*.

In exemplary embodiments, pricing tool 137 can be configured to derive an initial outside facility entry based on the facility affiliation(s) included the respective information record for the hospital system account in hospital system profile database 114*d* being used to access the pricing tool 137 functionality via provider portal 130 and include this derived facility entry as a default value within facility field 704*c*. Facility rate field 704*d* is provided for receiving and displaying an adjustment rate for facility services that, by default, is derived and provided by pricing tool 137 in correspondence with the characteristics of the facility that is currently specified as the entry within facility field 704*c*.

In the present example, pricing tool 137 is further configured to allow the provider user accessing service pricing page 700 to proceed to enter text corresponding to a name of a desired outside facility at which the services associated with the selected medical specialty would be performed within facility field 704*c*. In this regard, pricing tool 137 may be configured to require that the text entered by the user in facility field 704*c* correspond to the name of a particular facility specified in the facility affiliations included the respective information record for the hospital system account in hospital system profile database 114*d* being used to access the pricing tool 137 functionality via provider portal 130.

With continued reference to the example screen shot illustrated in FIG. 7A, pricing tool 137 has, in response to the user selection "Radiology" from medical specialty drop-down menu 702, configured the user interface options and populated the information displayed within rate adjustment section 706. More specifically, as shown in FIG. 7A, rate adjustment section 706 has been configured to include a physician rate adjustment field 706*a* and a facility rate adjustment field 706*b* in response to the selection of "Radiology" from drop-down menu 702. Physician rate adjustment field 706*a* is provided for making a general pricing adjustment to the pricing information included in detailed pricing information section 708 for physician fees for the services indicated as being commonly associated with radiology as desired by the provider user that may be based on any budgetary considerations specific to the provider and/or physician.

With continued reference to the example screen shot illustrated in FIG. 7A, as noted above, pricing tool 137 has, in response to the user selection "Radiology" from medical specialty drop-down menu 702, configured the user interface options and populated the information displayed within detailed pricing information section 708. In general, as shown in FIG. 7A, detailed pricing information section 708 is generated by pricing tool 137 as a table with various interactive user interface controls that includes a procedure column 711, a facility price column 712, a physician price column 713, an additional fee column 714, and a total amount column 715.

The information in procedure column 711 is generated by pricing tool 137 to include a row entry for each procedure category listed in the respective information records for services that are maintained in service pricing information database 114*m* and include an indication that the service is commonly associated with the medical specialty selected via drop-down menu 702, which is "Radiology" for the example screen shot depicted in FIG. 7A. For instance, the procedure categories listed in procedure column 711 in the present example include "Bone Density DXA Extremity" radiology procedures, "Bone Density DXA Scan" radiology procedures, and "Videofluoroscopic Swallowing Study" radiology procedures. As further illustrated in FIG. 7A for the example of the "Bone Density DXA Extremity" radiology procedures listing in in procedure column 711, detailed pricing information section 708 is implemented to include user interface elements that are accessible by the user.

In the present example, the expanded information for the "Bone Density DXA Extremity" radiology procedures listing includes row entries for a "Dxa bone density/peripheral" service and a "Fracture assessment via dxa" service. As further illustrated in FIG. 7A, the expanded information for a particular procedure category further includes, for each service categorized as a sub-procedure of the procedure category, a medical code number used to identify the service (for example, a CPT code), a base facility rate, a base physician rate, an adjusted facility rate, and an adjusted physician rate. The base physician rate for each service listed in the expanded display is obtained by pricing tool 137 from standard national physician rate derived for the service and the adjusted physician rate for each service listed in the expanded display is calculated by pricing tool 137 for display within detailed pricing information section 708 by multiplying the corresponding base physician rate by both the current value that is specified in physician location rate field 704b of locality adjustment section 704 and the current percentage value that is specified in physician rate adjustment field 706a of recommended rate adjustment section 706.

In the present example, as further illustrated in FIG. 7A, the expanded information for a particular procedure category further includes a physician price field 711a that specifies a price that will be set by the provider user for each of the services that have been categorized under the expanded procedure category and a facility price field 711b that specifies a price that will be applied by the provider user for the use of an outside facility for each of the services that have been categorized under the expanded procedure category.

In exemplary embodiments, pricing tool 137 can be configured to derive and include initial, default price values within physician price field 711a and physician price field 711a. As further indicated in the example screen shot illustrated in FIG. 7A, the row entry for a particular procedure category will include a pricing value under physician price column 713 that corresponds to the pricing value that is specified within physician price field 711a in the expanded display for the procedure category, and, likewise, the row entry for a particular procedure category will include a pricing value under facility price column 712 that corresponds to the pricing value that is specified within facility price field 711b in the expanded display for the procedure category. In this regard, pricing tool 137 can be configured to dynamically update the pricing values provided under physician price column 713 and facility price column 712 in response to changes to the price values within physician price field 711a and facility price field 711b respectively. As further illustrated in FIG. 7A, the row entry for a particular procedure category can include a pricing value under total amount column 715 that is provided as a sum of the price values listed under facility price column 712, physician price column 713, and, if included, additional fee column 714 in the row entry for a particular procedure category. This represents the actual price at which each service listed in the expanded display for a procedure category would be offered for purchase via marketplace system 100 as a bundled set of services from the provider user accessing service pricing page 700 via provider portal 130.

As noted above and further illustrated in FIG. 7A, the user interface provided at service pricing page 700 in the present example also includes a set of accessible user interface controls 710a ("Email Prices"), 710b ("Save Changes"), and 710c ("Take Live"). For purposes of the present example, these user interface controls are provided within service pricing page 700 as selectable buttons. In the present exemplary embodiment, pricing tool 137 can be configured to, in response to a provider user selecting "Save Changes" button 710b, generate an information record that includes indications of all of the information.

In the present exemplary embodiment, pricing tool 137 can be configured to, in response to a provider user selecting "Email Prices" button 710a, provide user interface controls for allowing the user to specify an email address and send an electronic document that includes indications of the pricing information.

Finally, with reference to the present example, pricing tool 137 can be configured to, in response to a provider user selecting "Take Live" button 710c, automatically initiate, on behalf of the provider user, a service offering with procedure management service 133 to offer each of the services currently included within detailed pricing information section 708 of service pricing page 700 for the particular medical specialty presented selected by the user from drop-down menu 702 for purchase via server system 110. In this manner, pricing tool 137 can provide a mechanism for a provider to offer a large number of services for purchase via marketplace system 100 by customer users registered with the system without having to perform full set of operations described above for accessing functionality provided by procedure management service 133 to offer each of the services individually.

FIG. 7B is a screen shot illustrating a second example of a graphical user interface provided by service pricing page 700 for a user accessing provider portal 130 in association with a registered hospital system account. In the example illustrated in FIG. 7B, the user has selected "General Surgery" from medical specialty drop-down menu 702, and pricing tool 137 has, in response to this selection, configured the user interface options and populated the information displayed within locality adjustment section 704, rate adjustment section 706, and detailed pricing information section 708 in accordance with the selection of "General Surgery" from drop-down menu 702. More specifically, as shown in FIG. 7B, locality adjustment section 704 has been configured to include, in addition to the physician locality section and the facility section described above with reference to the example illustrated in FIG. 7C, an anesthesia locality section in response to the selection of "General Surgery" from drop-down menu 702. The anesthesia locality section is included within locality adjustment section 704 in response to pricing tool 137 recognizing that the respective information records for services.

In the present example, the anesthesia locality section includes an anesthesia location field 704e and an anesthesia location rate field 704f. The anesthesia location field 704e is for receiving and displaying an entry specifying the location at which the services indicated as being commonly associated with the selected medical specialty of general surgery within service pricing information database 114m would be performed, and the anesthesia location rate field 704f is configured to provide a rate adjustment factor for the pricing information included in detailed pricing information section 708 for the services indicated as being commonly associated with radiology.

Anesthesia location rate field 704*f* is provided for receiving and displaying a geographic adjustment rate for physician services that, by default, is derived and provided by pricing tool 137 in correspondence with the anesthesia location entry that is currently specified within anesthesia location field 704*e*. More particularly, in exemplary embodiments, pricing tool 137 can be configured to access the information pertaining to anesthesia rate adjustments in service pricing information database 114*n* corresponding to the anesthesia location entry that is currently specified within anesthesia location field 704*e* and derive a corresponding geographic adjustment rate that is displayed as a default value within anesthesia location rate field 704*e*. The corresponding geographic adjustment rate can be derived, for example, based on a ratio of the CMS anesthesia conversion factor to a standard, national anesthesia conversion factor.

Specification of a new location within anesthesia location field 704*e*, pricing tool 137 can be configured to dynamically access the information pertaining to physician rate adjustments in geographic factors database 114*n* corresponding to the newly specified physician location entry within anesthesia location field 704*e* and derive a corresponding geographic adjustment rate that is displayed as the current value within anesthesia location rate field 704*f*. In the present example, pricing tool 137 is also configured to allow the provider user to directly access anesthesia location rate field 704*f* and specify a desired value for the geographic adjustment rate that will override the particular geographic adjustment rate that is derived by pricing tool 137 based on the location entry within anesthesia location field 704*e* and displayed as the current value within anesthesia location rate field 704*f* The effect of such an entry being submitted within anesthesia rate field 704*f* will be described below with reference to detailed pricing information section 708.

With continued reference to the example screen shot illustrated in FIG. 7B, as noted above, pricing tool 137 has, in response to the user selection "General Surgery" from medical specialty drop-down menu 702, configured the user interface options and populated the information displayed within rate adjustment section 706.

With continued reference to the example screen shot illustrated in FIG. 7B, as noted above, pricing tool 137 has, in response to the user selection "General Surgery" from medical specialty drop-down menu 702, configured the user interface options and populated the information displayed within detailed pricing information section 708. In general, as shown in FIG. 7B, detailed pricing information section 708 is generated by pricing tool 137 as a table with various interactive user interface controls that includes, in addition to procedure column 711, facility price column 712, physician price column 713, additional fee column 714, and total amount column 715, an anesthesia price column 716. As illustrated in FIG. 7B, the expanded information for a particular procedure category further includes, for each service categorized as a sub-procedure of the procedure category, in addition to a medical code number used to identify the service, a base facility rate, a base physician rate, an adjusted facility rate, and an adjusted physician rate as described above with reference to FIG. 7A, a base anesthesia rate and an adjusted anesthesia rate.

In the present example, as further illustrated in FIG. 7B, the expanded information for a particular procedure category further includes, in addition to physician price field 711*a* and facility price field 711*b*, an anesthesia price field 711*c* that specifies a price that will be applied by the provider user for each anesthesia service performed in association with the services that have been categorized under the expanded procedure category.

For example, pricing tool 137 can be configured to enable the user select between using the average of the corresponding adjusted anesthesia rates for all services listed in the expanded display for a procedure category for the price values within anesthesia price field 711*c* or the highest of the corresponding adjusted anesthesia rates for all services listed in the expanded display for a procedure category for the price values within anesthesia price field 711*c*. In exemplary embodiments, pricing tool 137 can be further configured to allow the provider user accessing service pricing page 700 to access anesthesia price field 711*c* to input a particular price value within this field.

As further indicated in the example screen shot illustrated in FIG. 7B, the row entry for a particular procedure category will include a pricing value under anesthesia price column 716 that corresponds to the pricing value that is specified within anesthesia price field 711*c* in the expanded display for the procedure category. In this regard, pricing tool 137 can be configured to dynamically update the pricing value provided under anesthesia price column 716 in response to changes to the price value within anesthesia price field 711*c*. As discussed above, in exemplary configurations of pricing tool 137, such changes to the price value within anesthesia price field 711*c* in the expanded display for a particular procedure category may occur in response to changes to any of the current value that is specified in anesthesia location rate field 704*f* of locality adjustment section 704, the current percentage value that is specified in anesthesia rate adjustment field 706*c* of recommended rate adjustment section 706, changes in the particular method employed by pricing tool 137 to derive and set the price value within anesthesia price field 711*c*, and direct entries of a particular price value by a provider user within anesthesia price field 711*c*.

As further illustrated in FIG. 7B, the row entry for a particular procedure category can include a pricing value under total amount column 715 that is provided as a sum of the price values listed under facility price column 712, physician price column 713, anesthesia price column 716, and, if included, additional fee column 714 in the row entry for a particular procedure category. This represents the actual price at which each service listed in the expanded display for a procedure category would be offered for purchase via marketplace system 100 as a bundled set of services from the provider user accessing service pricing page 700 via provider portal 130. In exemplary embodiments, pricing tool 137 can be further configured to provide an option via user interface controls implemented within service pricing page 700 for a provider user that is accessing the service pricing page 700 and has selected a medical specialty from drop-down menu 702 for which pricing tool 137 recognizes that the respective information records for services indicated as being commonly associated with the selected medical specialty within service pricing information database 114*m* include information records having an indication that the service is a primary service of a bundled set of services that a secondary service associated with the primary service in the bundled set is an anesthesia procedure to not include information and options pertaining to the associated anesthesia procedures and anesthesia pricing information within the service pricing page for the selected medical specialty.

FIG. 7C is a screen shot illustrating a third example of a graphical user interface provided by service pricing page 700 for a user accessing provider portal 130 in association with a registered hospital system account. In the example illustrated in FIG. 7C, the user has selected "GI" (gastroenterology) from medical specialty drop-down menu 702, and pricing tool 137 has, in response to this selection, configured the user interface options and populated the information displayed within locality adjustment section 704, rate adjustment section 706, and detailed pricing information section 708 in accordance with the selection of "GI" from drop-down menu 702.

In general, as shown in FIG. 7C, detailed pricing information section 708 is generated by pricing tool 137 as a table with various interactive user interface controls that includes, in addition to procedure column 711, facility price column 712, physician price column 713, additional fee column 714, and total amount column 715, a pathology price column 717.

As illustrated in FIG. 7C, the expanded information for a particular procedure category further includes, for each service categorized as a sub-procedure of the procedure category, in addition to a medical code number used to identify the service, a base facility rate, a base physician rate, an adjusted facility rate, and an adjusted physician rate as described above with reference to FIG. 7A, a base pathology rate. The base pathology rate for each service listed in the expanded display is obtained by pricing tool 137 from the pathology rate for the service that is stored within the respective information record maintained for the service within service pricing information database 114m for display within detailed pricing information section 708.

In the present example, as further illustrated in FIG. 7C, the expanded information for a particular procedure category further includes, in addition to physician price field 711a and facility price field 711b, a pathology price field 711d that specifies a price that will be applied by the provider user for each pathology service performed in association with the services that have been categorized under the expanded procedure category. In exemplary embodiments, pricing tool 137 can be configured to derive and include an initial, default price value within pathology price field 711d. For example, pricing tool 137 can derive and set the default price value within pathology price field 711d as the average of the base pathology rates for all services listed in the expanded display for a procedure category. In exemplary embodiments, pricing tool 137 can be further configured to allow the provider user accessing service pricing page 700 to access pathology price field 711d to input a particular price value within this field.

As further indicated in the example screen shot illustrated in FIG. 7C, the row entry for a particular procedure category will include a pricing value under pathology price column 717 that corresponds to the pricing value that is specified within pathology price field 711d in the expanded display for the procedure category. In this regard, pricing tool 137 can be configured to dynamically update the pricing value provided under pathology price column 717 in response to changes to the price value within pathology price field 711d. As further illustrated in FIG. 7B, the row entry for a particular procedure category can include a pricing value under total amount column 715 that is provided as a sum of the price values listed under facility price column 712, physician price column 713, pathology price column 717, and, if included, additional fee column 714 and anesthesia price column 716 in the row entry for a particular procedure category. This represents the actual price at which each service listed in the expanded display for a procedure category would be offered for purchase as a bundled set of services via marketplace system 100 from the provider user accessing service pricing page 700 via provider portal 130.

In exemplary embodiments, the functionality that is provided within provider portal 130 for users of hospital system accounts can further include a set of user interface controls implemented by service selling service 135 that can be accessed by a user of a hospital system account to sell prepaid purchases of services to a customer in-person by operating a client system located at, for example, a medical clinic being visited by the customer to access application server 116. In this regard, service selling service 135 may provide functionality allowing a user of a hospital system account to sell, in addition to services that are offered for purchase by the hospital within server system 100, services that are constructed by a user of a hospital system account, including bundled sets of services.

In exemplary embodiments, the user interface implemented by account management service 131 may be further configured to provide user interface controls for requesting authorization for payment of a predetermined fee to gain access to the ability to offer healthcare products for purchase within marketplace system 100. Such a fee may be, for example, a one-time charge or a periodic charge (such as a monthly, biannual, or annual fee).

Upon the user indicating an intention to offer a healthcare product for purchase (for example, by selecting a "Offer Service" tab within the pharmacy account page implemented by provider portal 130), the user will be able to initiate a product offering with product management service 134 to offer a healthcare product for purchase via server system 110.

Upon the user indicating an intention within the pharmacy account page implemented by provider portal 130 to access various account management functions, the pharmacy administrator can access various user interface elements provided by account management service 131 to, for example, manage pharmacy and payment or compensation information, manage information pertaining to products offered for purchase by the pharmacy, and view a history of transactions performed for products offered for purchase by the pharmacy within server system 110.

In exemplary embodiments disclosed herein, because certain healthcare information may be considered highly confidential, marketplace system 100 can be implemented to provide for a high-level of security for information transferred between client applications executing on client systems 142 and application server 116. For illustration, whenever applicable, marketplace system 100 (for example, for operations and functionalities) may be implemented to comply with requirements under the Health Insurance Portability and Accountability Act (HIPAA). For example, if certain type of information should not be accessible to a specific party (for example, a prescription product manufacturer or service provider) according to HIPAA requirements or other confidentiality concerns, system 100 can implement information-control or information-protection measures that ensure the specific party cannot access that type of information. As another example, to protect patient privacy, information transmitted over a computer or communication network, such as information transmitted between application server 116 and any client system 140 and electronic messages transmitted by server system 110, can be encrypted. In exemplary embodiments, system 100 can be HIPAA-validated to ensure privacy and comply with all requirements.

Figure 8:
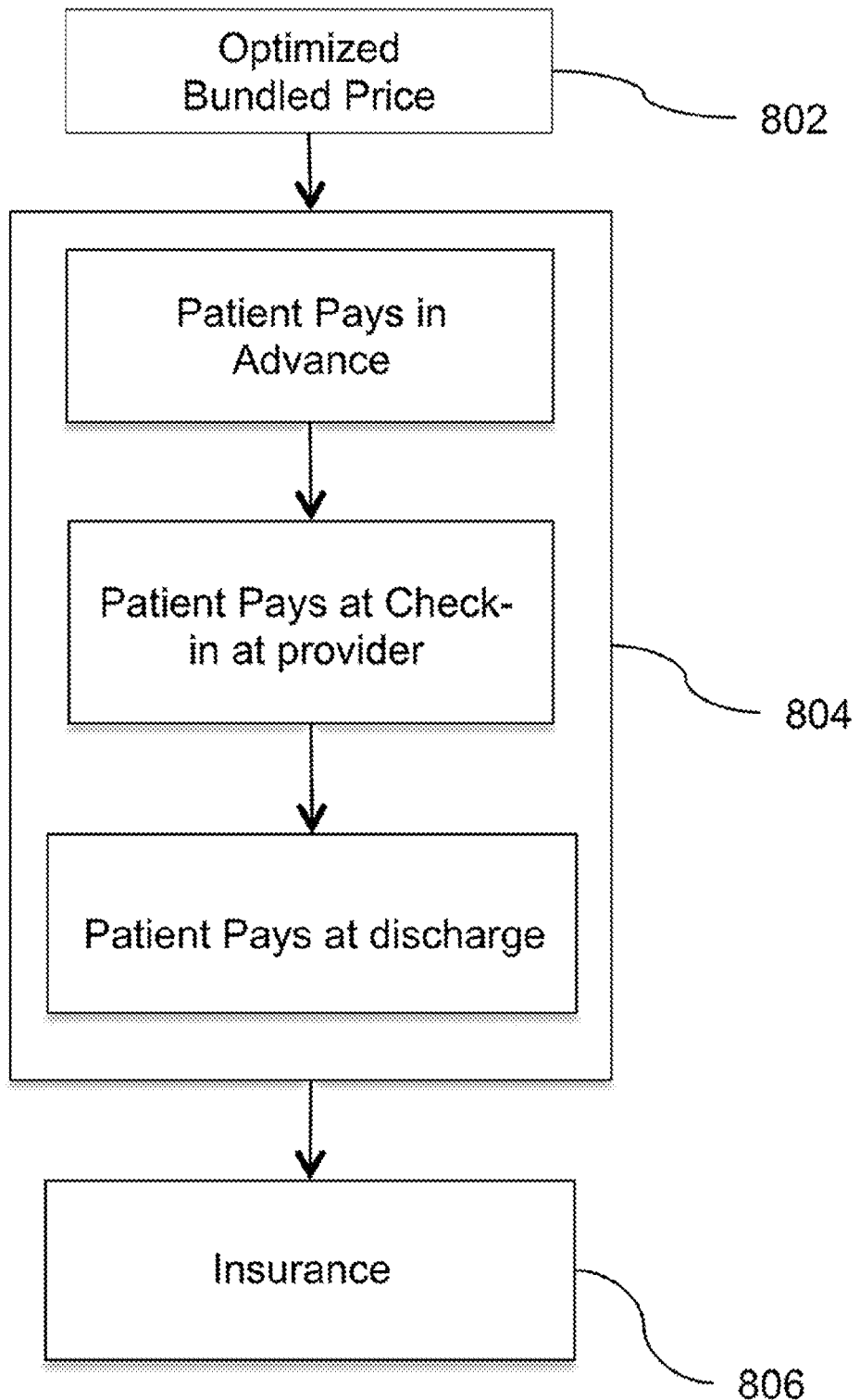
FIG. 8 illustrates a flow chart of an insurance policy stored in the insurance database executed by the application server in accordance with exemplary embodiments of the present invention.

FIG. 8 illustrates a flow chart of an insurance policy stored in the insurance database (114o, shown in FIG. 2) executed by the application server (116, shown in FIG. 2). The insurance database is programmed to provide an optimized bundled price 802 for healthcare services. For exemplary purposes, the system maximizes collections at each phase in the user's care cycle. For various phases there is an option for paying the payment 804. The patient is referred or scheduled for a procedure, where the patient may receive a push notification to pay prospectively. Alternatively, the patient checks-in at a provider's location and the patient pays at the point of service such as by cash, card, digital wallet, etc. Alternatively, the patient is made to pay after services are provided and/or at discharge wherein, the patient receives a push notification to pay retrospectively.

Further, each of the patient's information is monitored such as but not limited to a doctor's order/schedule (for example, CHC Redox), propensity to pay data (CHC-Vendor), benefit status (CHC-ribbon health) and CareCredit pre-approval. Based on the patient information, a doctor's order is matched. Further, the price is set based on the patient's capacity and/or willingness to pay for the service and/or product. Further, each payment is monitored to check if a patient is paying out-of-pocket. The system compares the bundled price to the remaining patient deductible to determine the patient's capacity to pay for the services and/or product. Furthermore, patients are allowed to pay either in full or through CareCredit.

The system is configured to pay the optimal price in full every time to the hospital/physician/pharmacy and any associated service provider. The procedure is transparent and acceptable to both patients and the provider. The service providers collect the maximum data on the patients who are willing to pay. Further, the hospital may leave revenue on the table by charging less than what patients are willing to pay.

The application server (116, shown in FIG. 2) processes the data stored in the insurance database 114o and allows the user to access the insurance information via an insurance management service (14, shown in FIG. 2). The hospital sends an electronic claim to the system after care is delivered to the patient. The system then distributes payment and sends an electronic remittance file based on the information stored in the insurance database 114o. The system passes the electronic claim to the insurance company 806 to update the patient's accumulator (not for reimbursement). The insurance 806 then notifies the system of accumulator status. The system then sends an update to the patients.

Figure 9:
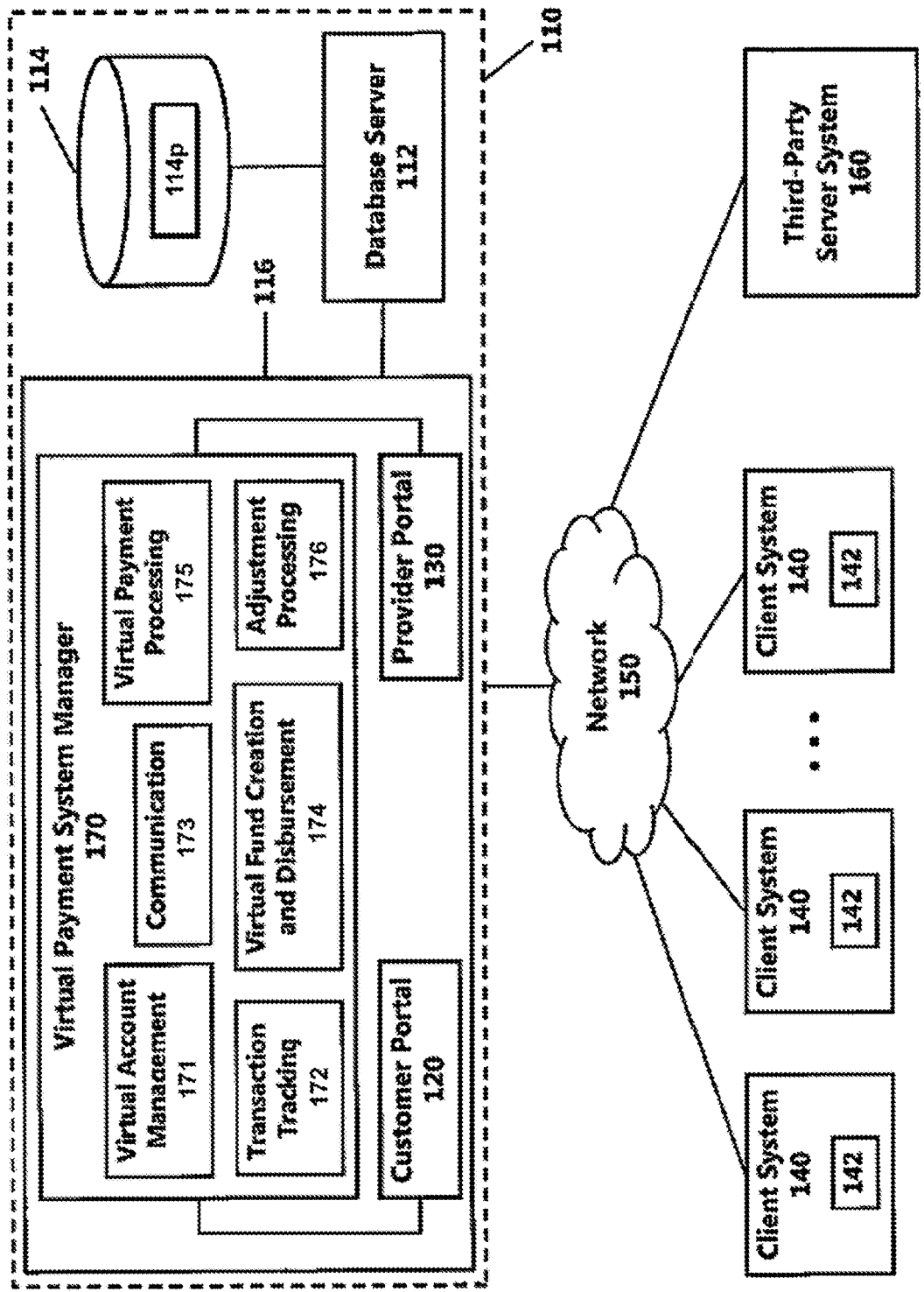
FIG. 9 illustrates a block diagram of a virtual payment system manager communicating with client system in a healthcare marketplace system.

FIG. 9 illustrates a block diagram of a virtual payment system manager 170 communicating with a client system in a healthcare marketplace system in accordance with another exemplary embodiment of the present invention. As noted above, exemplary embodiments of the present invention may be implemented to provide a virtual payment system for facilitating and accounting for the exchange of payment for services and products purchased by (or otherwise purchased on behalf of) patients and offered by healthcare providers via the creation, transfer, and redemption of virtual funds within a central server system 110.

In some exemplary embodiments, the virtual payment system manager 170 is configured to facilitate the tracking and management of promotional credits that may be offered by the providers of a healthcare marketplace system 100 to registered users of the server system 110 for taking certain actions within the system in association with their registered accounts.

For example, the providers of a marketplace system 100 may offer a promotion to potential customer users in which each user, upon completing registration of a respective customer account with server system 110, will receive a credit of a specified amount of funds (for instance, a credit of $25) that the customer user may use to purchase services and/or products offered within marketplace system 100 by provider users that are registered with server system 110.

In one embodiment, the virtual payment system manager 170 is configured to, access the database server 112 to create the respective account information record for the virtual money account for the customer within the virtual money account database 114o, and access database server 112 to create a new virtual fund corresponding to a specified amount for a promotional credit within the database of virtual fund objects included in the respective account information record.

In this regard, the virtual payment system manager 170 generates a unique identifier for the new virtual fund object being created and defines the attributes of the object to include an indication of the value of the corresponding virtual funds, the unique identifier generated for the object, an indication that the original funding source is a credit that was conveyed by the providers of marketplace system 100, a creation timestamp for the object, an indication that the corresponding virtual funds for the object are not presently allocated to use as payment for an offered service or product purchased within the marketplace system, and, optionally, an indication of an expiration date for the promotional credit by which the customer user must use the credited funds to purchase the services and/or products offered within marketplace system 100.

In such an example, the virtual payment system manager 170 is configured to further access database server 112 to also create a corresponding new virtual fund object for the promotional credit within the container of virtual fund objects included in the respective account information record for a respective virtual money account that is being maintained within virtual money account database 114o for an entity that provides the marketplace system (which may have already been established, for example, by a backend administrator of server system 110). More specifically, virtual payment system manager 170 generates a unique identifier for the new virtual fund object being created and define the attributes of the object to include an indication of the value of the corresponding virtual funds as a negative value, the unique identifier generated for the object, an indication that the original funding source is a corresponding amount of real currency held within an external financial account maintained by the providers of marketplace system 100 (and thereby owed to the virtual payment system by the marketplace system providers), and a creation timestamp for the object.

In one embodiment the virtual payment system manager 170 is also configured to, upon creating the corresponding virtual fund objects for the promotional credit within the respective account information records for the virtual money accounts for the customer user and the entity that provides the marketplace system within virtual money account database 114o, updates the total balance values and available balance values included in the sets of general information within the respective account information records for the respective virtual money accounts appropriately to reflect the newly-created virtual fund objects.

In the example illustrated in FIG. 9, the particular components that are utilized for providing the virtual payment system are integrated within system 100 in conjunction with the components of the system as described above and herein below with reference to the exemplary embodiments illustrated FIGS. 1 and 2. In particular, as depicted in FIG. 9, application server 116 is further implemented to include virtual payment system manager 170. As also depicted in FIG. 9, data store 114 further comprises virtual money account database 114p, which is maintained by database server 112, is accessed by application server 116.

In the present exemplary embodiment, virtual payment system manager 170 is shown in FIG. 9 as including a virtual account management module 171, a transaction tracking module 172, a communication module 173, a virtual fund creation and disbursement module 174, a virtual payment processing module 175, and an adjustment processing module 176. In general, the various modules implemented within virtual payment system manager 170 in the present exemplary embodiments are configured to interact with one another, customer portal 120, provider portal 130, and data store 114 via database server 112 to perform the various operations described in the examples provided above pertaining to exemplary embodiments in which a virtual payment system is implemented within server system 110.

The virtual account management module 171 is configured to access virtual money account database 114p to create respective account information records for respective virtual money accounts of participants to transactions conducted within marketplace system 100. The virtual account management module 171 retrieves, maintains, performs modifications to respective information account records as necessary in response to participants that are logged-in to server system 110 accessing the account management functions provided by account management service 122 or account management service 131 to manage and view information pertaining to the respective virtual money accounts for the participants within the virtual payment system.

Transaction tracking module 172 can, for example, be configured to dynamically perform updates to the accounting details pertaining to transactions conducted within the virtual payment system. The module 172 dynamically calculates and performs updates to the balance values that are included within the general information in the respective account information records for the respective virtual money accounts in response to transactions conducted within the virtual payment system.

Further, module 172 dynamically performs processing for handling virtual fund objects that have been created within the virtual money account based on promotional credits that have expired in response to such expirations occurring, and dynamically perform processing for reversing payment processing operations performed within the virtual payment system for purchases of offered services and products that have not been redeemed within expiration periods specified for such purchases in response to the end of such expiration periods being reached Communication module 173 can, for example, be configured to generate notifications and reports with respect to virtual money accounts managed and transactions conducted within the virtual payment system, transmit generated notifications and reports to corresponding components of customer portal 120 and provider portal 130, receive notifications and information from corresponding components of customer portal 120 and provider portal 130, and process such received notifications and information.

Virtual fund creation and disbursement module 174 can, for example, be configured to implement functionality for creating or instantiating new virtual fund objects within respective account information records for virtual money accounts as needed for transactions conducted within the virtual payment system, processing disbursal requests within the virtual payment system (including functionality for deleting virtual fund objects), and performing automatic periodic disbursals for virtual money accounts within the virtual payment system.

Virtual payment processing module 175 can, for example, be configured to implement functionality for performing operations for facilitating payment processing within the virtual payment system for purchases of offered services and products by customers users registered with server system 110, as well as to perform corresponding updates to the attributes defining the virtual fund objects within the respective account information records in response to performing such operations for facilitating payment processing within the virtual payment system. Adjustment processing module 176 can, for example, be configured to implement functionality for performing operations for processing cancellation requests, refund requests, and other modifications to purchases of offered services and products for which payment processing is handled within the virtual payment system, as well as to perform corresponding updates to the attributes defining the virtual fund objects within the respective account information records in response to performing such operations for processing cancellation requests, refund requests, and other modifications to purchases within the virtual payment system.

In exemplary embodiments disclosed herein, because certain healthcare information may be considered highly confidential, marketplace system 100 can be implemented to provide for a high-level of security for information transferred between client applications executing on client systems 142 and application server 116. For illustration, whenever applicable, marketplace system 100 (for example, for operations and functionalities) may be implemented to comply with requirements under the Health Insurance Portability and Accountability Act (HIPAA). As another example, to protect patient privacy, information transmitted over a computer or communication network, such as information transmitted between application server 116 and any client system 140 and electronic messages transmitted by server system 110, can be encrypted. In exemplary embodiments, system 100 can be HIPAA-validated to ensure privacy and comply with all requirements.

Figure 10:
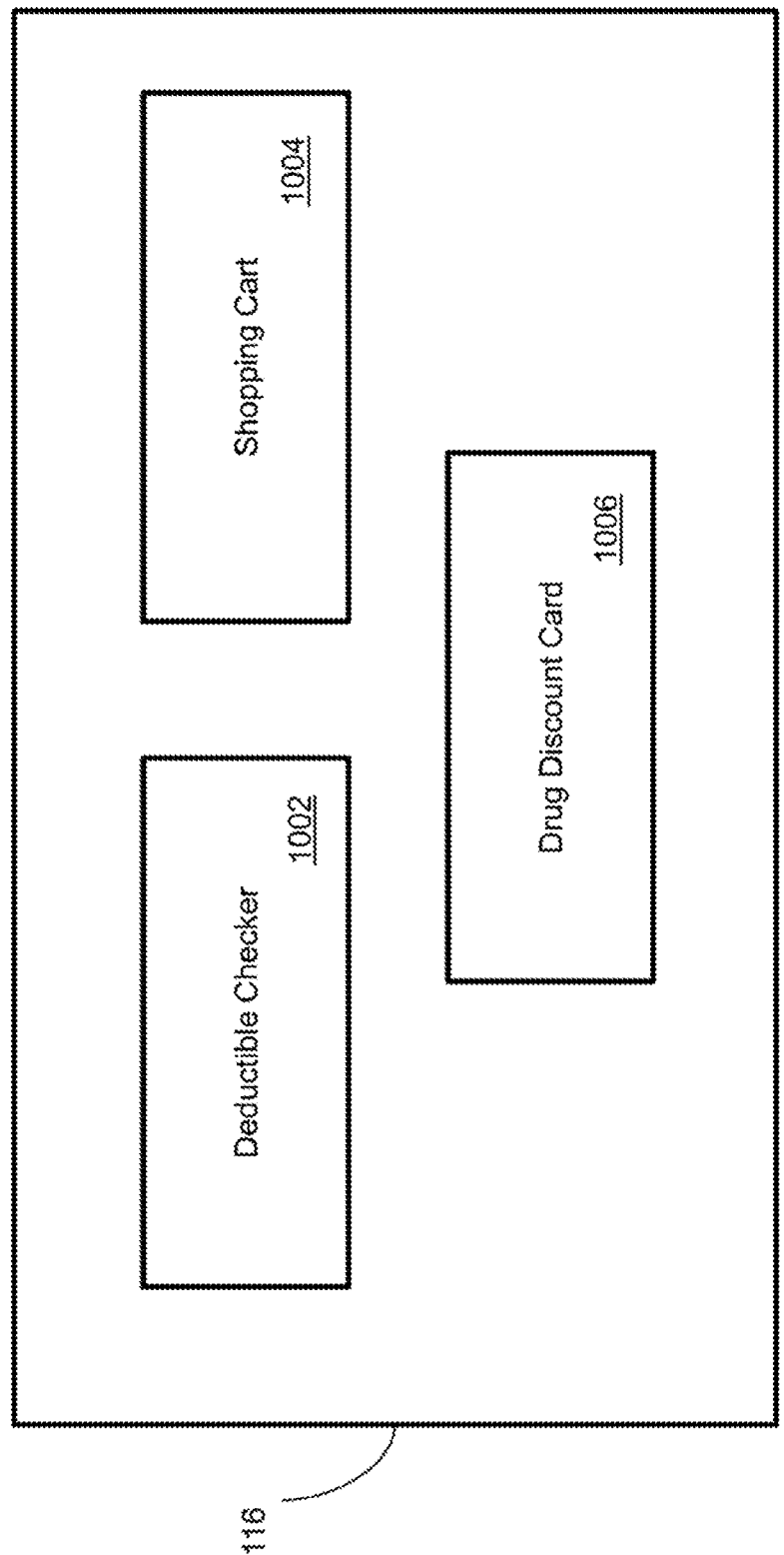
FIG. 10 illustrates a block diagram of the application server showing deductible checker, shopping cart, and drug discounted card in accordance with another embodiment of the present invention.

FIG. 10 illustrates a block diagram of the application server showing a deductible checker, shopping cart and drug discount card in accordance with another embodiment of the present invention. The application server 116 may further include a deductible checker 1002 to look up the patient's deductible, a shopping cart 1004 for providing details of pricing to the user, and a drug discount card 1006 for the user for subscription of healthcare services.

The deductible checker 1002 allows patient's/user's to look up their deductible and to let the user know whether the healthcare service offered is at better and/or competitive prices. The shopping cart 1004 is automatically communicated to the registered users with the pricing details of the healthcare services with which they intend to proceed. The shopping cart 1004 is automatically communicated such as but not limited to email, SMS, flashing on the graphical user interface, and any other similar communication networks etc. The shopping cart 1004 automatically checks for any deductibles, insurance and accordingly generates the pricing for the user.

In another embodiment, the shopping cart 1004 is verified by an analyst to confirm the pricing. Thus, the shopping cart is sent to the analyst system and then to the user. This allows the user to pre-pay for the healthcare services. Further, the shopping cart 1004 is generated with the right bundled prices (e.g. accounting for discounts when certain procedures are purchased together etc.). The drug discount card 1006 is provided to the users who subscribe to the healthcare services.

Figure 11:
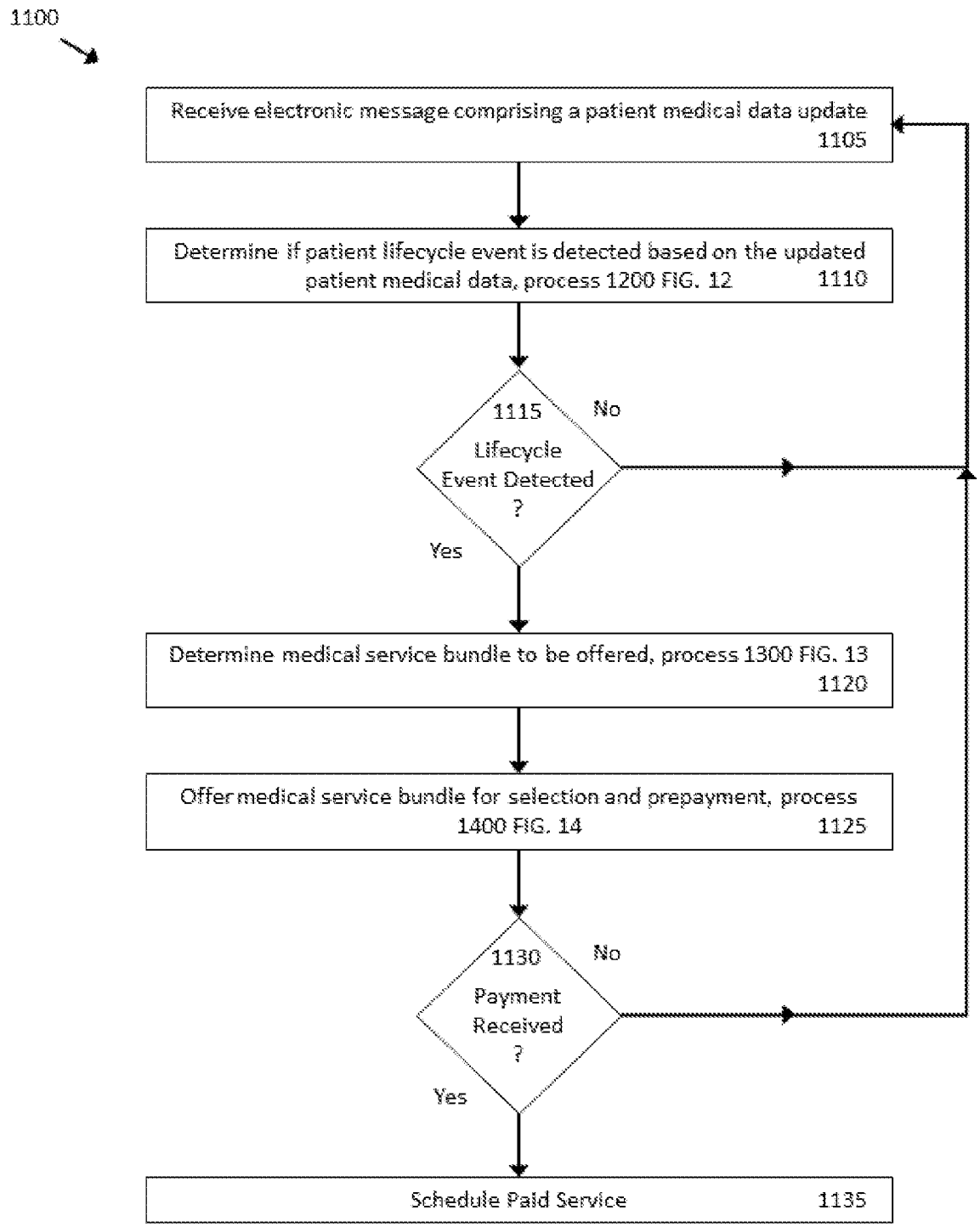
FIG. 11 is a process flow illustrative of an example aspect of patient lifecycle event triggered shopping cart provisioning design.

FIG. 11 is a process flow illustrative of an example aspect of patient lifecycle event triggered shopping cart provisioning design. The method depicted in FIG. 11 is given from the perspective of an exemplary patient lifecycle event triggered shopping cart provisioning engine (SCPE) implemented via processor-executable program instructions executing on the SCPE processor 604, depicted in FIG. 5. In various embodiments, the processor 604 implementing the process 1100 may be configured in an exemplary system 100 as described herein with reference to any of FIGS. 1, 6, and 9. For example, the depicted process may execute as processor executable program instructions on processor 604 configured in the application server 116, depicted in FIGS. 1, 6, and 9. In various embodiments, the method depicted in FIG. 11 may also be understood as from the perspective of processor-executable program instructions executing on a mobile device operably coupled with the network 150, depicted at least in FIGS. 1, 6, and 9. In the illustrated embodiment, the SCPE executes as program instructions on the processor 604, depicted in FIG. 5. In some embodiments, the SCPE may execute as a cloud service communicatively and operatively coupled with system services, hardware resources, or software elements local to and/or external to the SCPE processor 604.

The depicted method 1100 begins at step 1105 with the processor 604 receiving an electronic message comprising a patient medical data update. The electronic message may include an EHR (Electronic Health Record). The EHR may include updated patient medical data. The patient medical data may be updated relative to historical patient medical data. The processor 604 may access and store the patient medical data using the customer profile database 114*a*, depicted in FIG. 2.

Then, the method continues at step 1110 with the processor 604 determining if a patient lifecycle event is detected based on the updated patient medical data. The processor 604 executes the process 1200, depicted by FIG. 12 and described herein, to determine if a patient lifecycle event is detected. The processor 604 may determine if a patient lifecycle event is detected based on accessing and storing patient, practice, or condition data using, for example, any of customer profile database 114*a*, practice group profile database 114*c*, or condition information database 114*f*, depicted in FIG. 2.

Then, the method continues at step 1115 with the processor 604 performing a test to determine if a patient lifecycle event is detected, based on the execution of process 1200 by the processor 604 at step 1110. Upon a determination by the processor 604 at step 1115 that a patient lifecycle event has not been detected, the method continues at step 1105 with the processor 604 receiving an electronic message comprising a patient medical data update.

Figure 13:
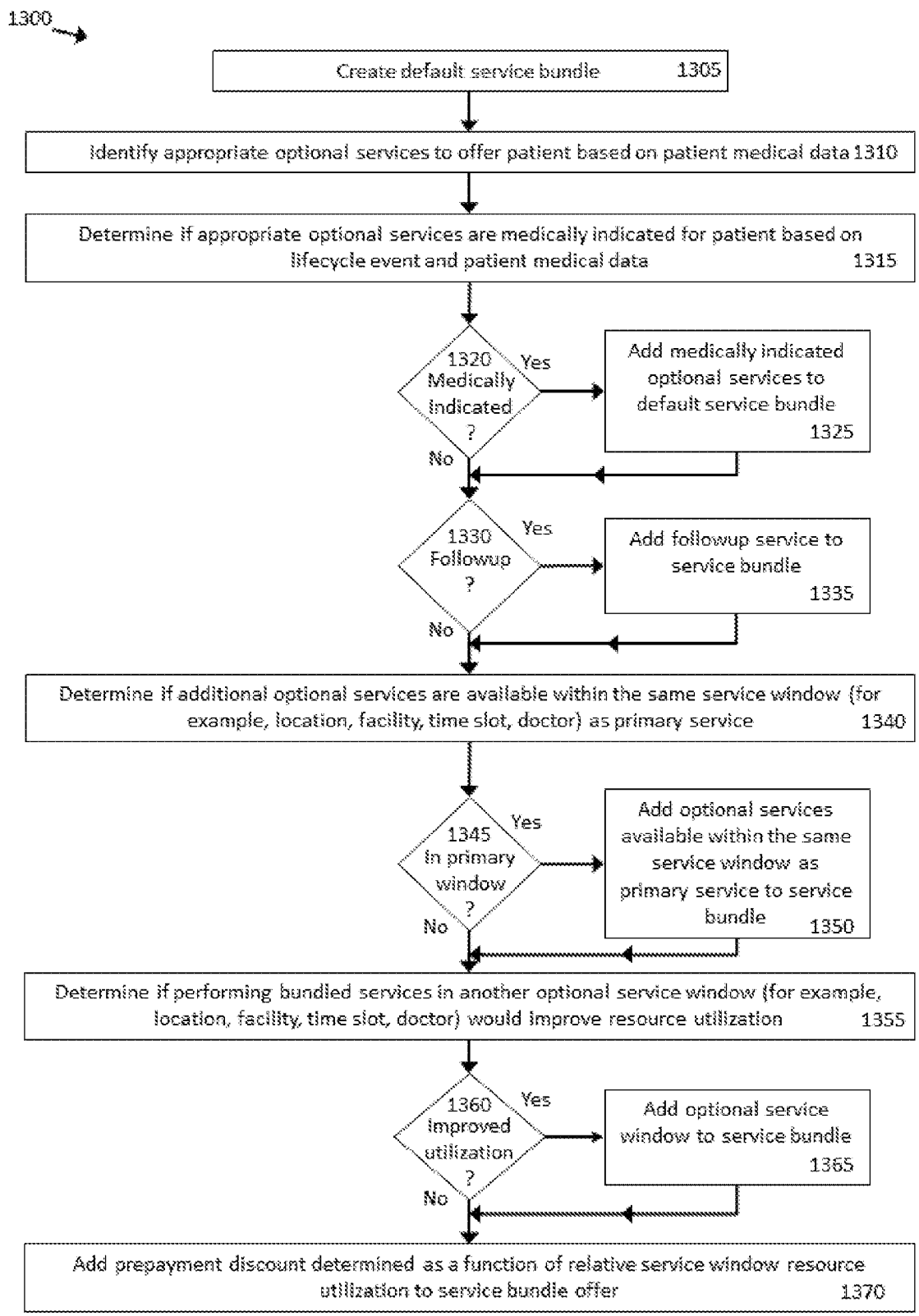
FIG. 13 is a process flow illustrative of an example aspect of patient lifecycle event triggered shopping cart provisioning design.

Upon a determination by the processor 604 at step 1115 that a patient lifecycle event has been detected, the method continues at step 1120 with the processor 604 executing the process 1300, depicted by FIG. 13 and described herein, to determine a medical service bundle to be offered. The processor 604 may determine the medical service bundle based on accessing and storing medical service data using any of customer profile database 114*a*, physician profile database 114*b*, practice group profile database 114*c*, condition information database 114*f*, or available service database 114*g*, depicted in FIG. 2.

Figure 14:
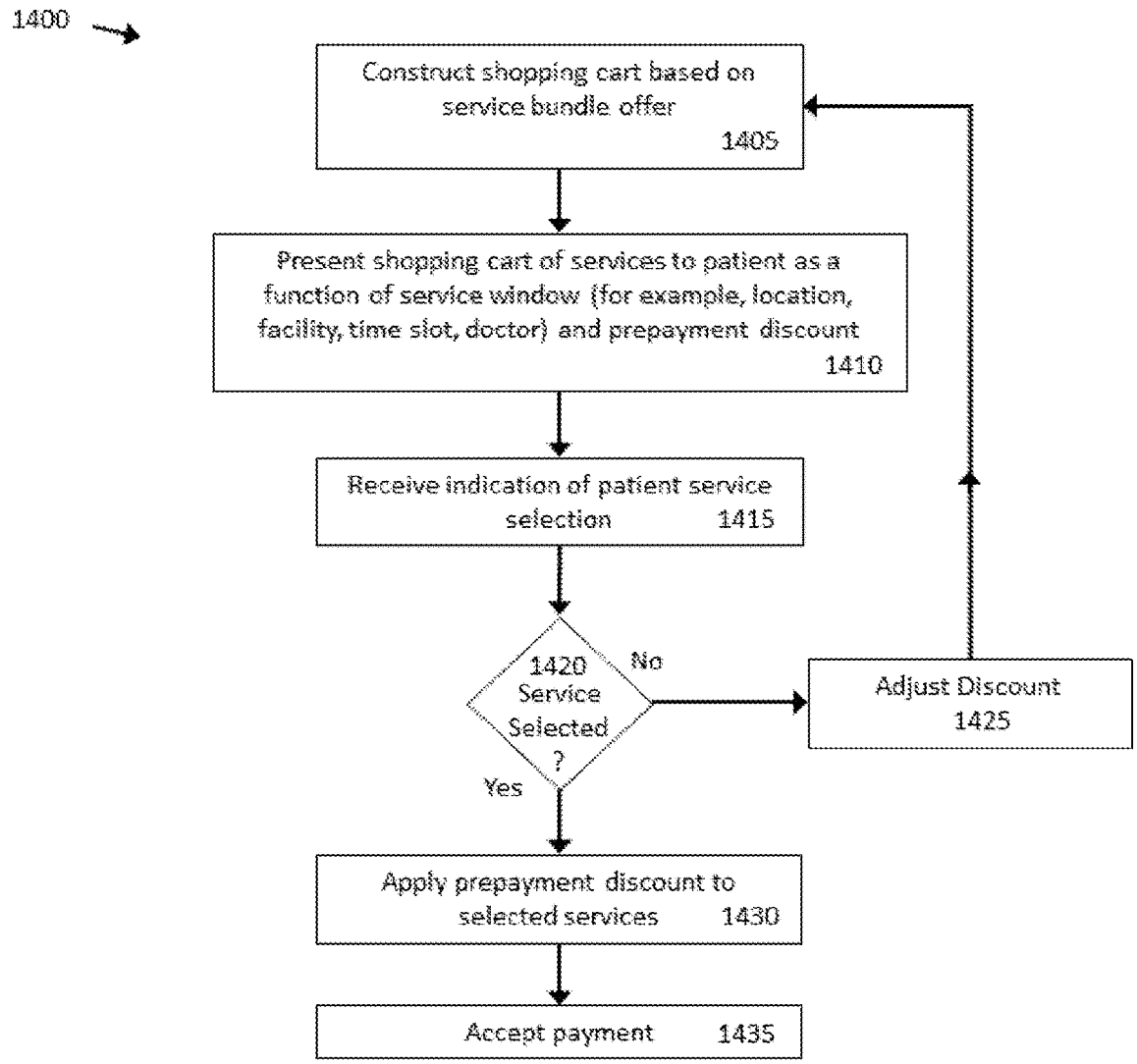
FIG. 14 is a process flow illustrative of an example aspect of patient lifecycle event triggered shopping cart provisioning design.

Then, the method continues at step 1125 with the processor 604 executing the process 1400, depicted by FIG. 14 and described herein, to offer the medical service bundle for selection and prepayment. For example, the processor 604 may offer the medical service bundle for selection and payment through the customer portal 120 (depicted by FIG. 2), using techniques similar to those described herein with reference to the account management service 122 and purchasing service 126 (both depicted by FIG. 2).

Then, the method continues at step 1130 with the processor 604 performing a test to determine if payment for the medical service bundle has been received. Upon a determination by the processor 604 at step 1130 payment has not been received, the method continues at step 1105 with the processor 604 receiving an electronic message comprising a patient medical data update.

Upon a determination by the processor 604 at step 1130 payment was received, the method continues at step 1135 with the processor 604 scheduling the paid services. In various embodiments, the method may repeat. In some designs, the method may end.

Figure 12:
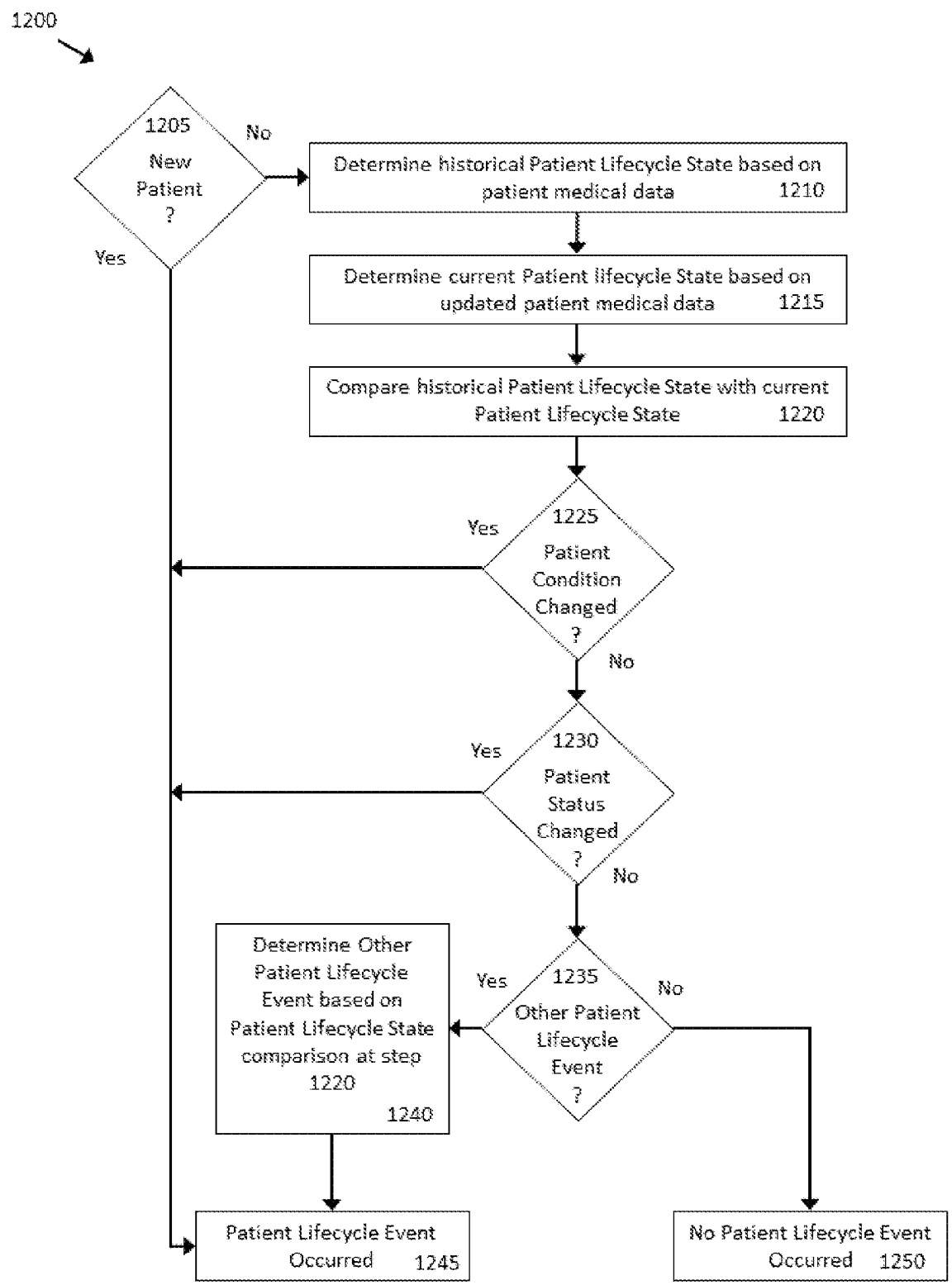
FIG. 12 is a process flow illustrative of an example aspect of patient lifecycle event triggered shopping cart provisioning design.

FIG. 12 is a process flow illustrative of an example aspect of patient lifecycle event triggered shopping cart provisioning design. The method depicted in FIG. 12 is given from the perspective of an exemplary patient lifecycle event triggered shopping cart provisioning engine (SCPE) implemented via processor-executable program instructions executing on the SCPE processor 604, depicted in FIG. 5. In various embodiments, the processor 604 implementing the process 1200 may be configured in an exemplary system 100 as described herein with reference to any of FIGS. 1, 6, and 9. In various embodiments, the method depicted in FIG. 12 may also be understood as from the perspective of processor-executable program instructions executing on a mobile device operably coupled with the network 150, depicted at least in FIGS. 1, 6, and 9. For example, the depicted process may execute as processor executable program instructions on processor 604 configured in the application server 116, depicted in FIGS. 1, 6, and 9. In the illustrated embodiment, the SCPE executes as program instructions on the processor 604, depicted in FIG. 5. In some embodiments, the SCPE may execute as a cloud service communicatively and operatively coupled with system services, hardware resources, or software elements local to and/or external to the SCPE processor 604. The depicted method 1200 begins at step 1205 with the processor 604 performing a test to determine if the patient is a new patient. The processor 604 may implement the test to determine if the patient is a new patient based on patient medical data encoded by an EHR.

Upon a determination by the processor 604 at step 1205 the patient is a new patient, the method continues at step 1245 with the processor 604 indicating to the invoking process that a patient lifecycle event occurred.

Upon a determination by the processor 604 at step 1205 the patient is not a new patient, the method continues at step 1210 with the processor 604 determining the patient's historical patient lifecycle state based on patient medical data. The historical patient lifecycle state may be the patient's lifecycle state previous to the current invocation of process 1200. The historical patient lifecycle state may be administratively assigned. The historical patient lifecycle state may be programmatically determined by the processor 604 as a function of patient medical data encoded by an EHR. The processor 604 may determine the historical patient lifecycle state based on, for example, patient medical data encoded by a previously processed EHR, administratively configured patient medical data, or an administratively configured lifecycle state. In illustrative examples, the EHR may encode patient physiological data such as, for example, a laboratory test report indicating the concentration of a substance in the patient's body, or a test result indicating a measured patient physiological parameter such as blood pressure, heart rate, weight, or height. The processor 604 may programmatically determine the historical patient lifecycle state based on, for example, operations such as comparing, or correlating, patient medical data encoded by an EHR with one or more range of similar data to determine the patient lifecycle state. In an illustrative example, the processor 604 may determine the patient lifecycle state to be new patient, well patient, acute care patient, chronic care patient, or recovering patient. Other patient lifecycle states may be determined by the processor 604 based on programmatically analyzing patient medical data such as laboratory results and measurements to determine correspondence with standardized or administratively determined medical data ranges. For example, at step 1210 the processor 604 may determine a patient with a blood pressure in a predetermined range is an acute care patient based on patient medical data encoded by an EHR.

Then, the method continues at step 1215 with the processor 604 determining the current patient lifecycle state based on updated patient medical data. The processor 604 may programmatically determine the current patient lifecycle state based on updated patient medical data encoded by an EHR. The EHR encoding updated patient medical data may be provided as input to the system as a result of a patient's examination by a medical professional. The EHR encoding updated patient medical data may be provided as input to the system as a result of a measurement by a doctor during a patient visit. The EHR encoding updated patient medical data may be provided as input to the system as a result of a measurement remotely performed by a patient in a care context such as telemedicine, or self-care by the patient in the patient's home. The operations performed by the processor 604 to determine the current patient lifecycle state at step 1215 are in line with the operations performed by the processor 604 at step 1210 to determine the historical patient lifecycle state. In any case, the processor 604 at step 1215 determines the current patient lifecycle state based on evaluating patient medical data that has been updated. In this example, the patient medical data has been updated relative to the patient medical data analyzed by the processor 604 at step 1210 to determine the historical patient lifecycle state.

Then, the method continues at step 1220 with the processor 604 comparing the historical patient lifecycle state determined by the processor 604 at step 1210 with the current patient lifecycle state determined by the processor 604 at step 1215, to determine if a patient lifecycle event occurred based on the comparison. In an illustrative example, the processor 604 may compare the historical and current lifecycle states based on comparing archived patient medical data with updated patient medical data.

Then, the method continues at step 1225 with the processor 604 performing a test to determine if the patient condition changed. The processor 604 may determine if the patient condition changed based on comparing archived patient medical data, such as, for example, a previous blood pressure measurement or laboratory test result, with patient medical data updated by a more recent measurement or result. For example, the processor 604 may determine patient condition changed if a more recent test result or measurement is in a different range than a previous test result or measurement. Upon a determination at step 1225 by the processor 604 patient condition changed, the method continues at step 1245 with the processor 604 indicating to the invoking process that a patient lifecycle event occurred.

Upon a determination by the processor 604 at step 1225 the patient condition did not change, the method continues at step 1230 with the processor 604 performing a test to determine if the patient status changed. The processor 604 may determine if patient status changed based on administratively configured or programmatically determined patient status. The processor 604 may determine if patient status changed based on comparing archived patient data with updated patient data. The patient data used by the processor 604 to determine patient status may be medical, billing, payment, insurance, or other data. In an illustrative example, patient status may be new patient, active patient, inactive patient, former patient, referral patient, or referred patient. For example, the processor 604 may determine patient status changed from active to inactive if the patient has not kept an appointment for at least a predetermined time period. The processor 604 may determine the patient is a new patient if patient records were not previously accessible to the system. A referral patient may have been referred from another medical practice, and in view of this, patient care of such a patient may benefit from customized consideration, in line with what may be known by one of skill in the art. A referred patient may have specific goals resulting in the patient's referral to another medical practice, or to a specialist, for example. In an illustrative example, the referred patient may benefit from optional services offered through the specialist's practice. In any case, upon a determination by the processor 604 at step 1230 the patient status changed, the method continues at step 1245 with the processor 604 indicating to the invoking process that a patient lifecycle event occurred.

Upon a determination by the processor 604 at step 1230 the patient status did not change, the method continues at step 1235 with the processor 604 performing a test to determine if another patient lifecycle event occurred. The operations performed by the processor 604 at step 1235 to determine if another patient lifecycle event has occurred may include comparing archived patient data with updated patient data encoded by an EHR received with a notification or administratively configured in the system. In any case the processor 604 may determine a patient lifecycle event other than a change in patient condition or status has occurred, based on comparing the archived and updated patient data, to determine if a change has occurred based on the comparison. The change detected by the processor 604 may be any change in patient data that has not been identified previously.

Upon a determination by the processor 604 at step 1235 another patient lifecycle event has not occurred, the method continues at step 1250 with the processor 604 indicating to the invoking process that no patient lifecycle event occurred.

Upon a determination by the processor 604 at step 1235 another patient lifecycle event has occurred, the method continues at step 1240 with the processor 604 determining the patient lifecycle event that did occur, based on the patient lifecycle state comparison performed by the processor 604 at step 1220. The operations performed by the processor 604 to determine the patient lifecycle event at step 1240 are in line with the operations performed by the processor 604 at step 1225 and step 1230 with deeper analysis of the patient data at step 1240. The patient data analysis performed by the processor 604 at step 1240 may include lifecycle event determination based on patient data input to a predictive analytic, machine learning, or artificial intelligence model trained with patient data.

Then, the method continues at step 1245 with the processor 604 indicating to the invoking process that a patient lifecycle event occurred. In various embodiments, the method may repeat. In some designs, the method may end.

FIG. 13 is a process flow illustrative of an example aspect of patient lifecycle event triggered shopping cart provisioning design. The method depicted in FIG. 13 is given from the perspective of an exemplary patient lifecycle event triggered shopping cart provisioning engine (SCPE) implemented via processor-executable program instructions executing on the SCPE processor 604, depicted in FIG. 5. In various embodiments, the processor 604 implementing the process 1300 may be configured in an exemplary system 100 as described herein with reference to any of FIGS. 1, 6, and 9. For example, the depicted process may execute as processor executable program instructions on processor 604 configured in the application server 116, depicted in FIGS. 1, 6, and 9. In various embodiments, the method depicted in FIG. 13 may also be understood as from the perspective of processor-executable program instructions executing on a mobile device operably coupled with the network 150, depicted at least in FIGS. 1, 6, and 9. In the illustrated embodiment, the SCPE executes as program instructions on the processor 604, depicted in FIG. 5. In some embodiments, the SCPE may execute as a cloud service communicatively and operatively coupled with system services, hardware resources, or software elements local to and/or external to the SCPE processor 604. The depicted method 1300 begins at step 1305 with the processor 604 creating a default service bundle. The default service bundle created by the processor 604 may include a service for which a patient is already registered. The service for which the patient is already registered may be a primary service. The default service bundle may include a service window parameter related to a bundled service, such as, for example, location, facility, time slot, or doctor. The processor 604 may create the default service bundle as an empty bundle with no service, or no service window.

Then, the method continues at step 1310 with the processor 604 identifying appropriate optional services to offer to the patient based on patient medical data. The processor 604 may determine an optional service is appropriate to a patient if the optional service considered is not contraindicated by medical care standards, in view of the patient's medical condition. The patient's medical condition may be determined by the processor 604 using techniques like those described herein with reference to process 1200, depicted by FIG. 12.

Then, the method continues at step 1315 with the processor 604 determining if any of the optional services determined at step 1310 by the processor 604 as appropriate are medically indicated for the patient based on the current patient lifecycle event and patient medical data. The processor 604 may determine an optional service is medically indicated for a patient if the service is related by medical care standards to the patient condition. For example, if a medical care standard suggests a doctor treating a patient with a given condition should also consider treatment with a particular class of drug or screening by a particular test for another condition, the processor 604 may determine that consideration of the drug treatment or screening test may be medically indicated for the patient based on the current patient lifecycle event and patient medical data. The current patient lifecycle event may be determined by the processor 604 using techniques similar to those described herein with reference to process 1200, depicted by FIG. 12.

Then, the method continues at step 1320 with the processor 604 performing a test to determine if medically indicated procedures should be added to the default service bundle, based on the determination by the processor 604 at step 1315, as to whether appropriate optional services may be medically indicated. Upon a determination at step 1320 by the processor 604 some appropriate optional service is medically indicated; the method continues at step 1325 with the processor 604 adding at least one medically indicated appropriate optional service to the default service bundle. The service added to the service bundle by the processor 604 may include a service window parameter related to the added service, such as, for example, location, facility, time slot, or doctor.

Upon a determination at step 1320 by the processor 604 no appropriate optional service is medically indicated; the method continues at step 1330 with the processor 604 performing a test to determine if a follow-up service may be added to the service bundle. A follow-up service may be, for example, mandatory, such as a post-surgical visit for suture removal. In some cases, a follow-up service may be optional. A candidate follow-up service considered by the processor 604 for addition to the service bundle may be a follow-up service to a primary service, or a follow-up service to an optional service. Upon a determination by the processor 604 at step 1330 some follow-up service may be added to the service bundle, the method continues at step 1335 with the processor 604 adding at least one follow-up service to the service bundle.

Upon a determination by the processor 604 at step 1330 no follow-up service may be added to the service bundle, the method continues at step 1340 with the processor 604 determining if additional optional services are available within the same service window (for example, location, facility, time slot, or doctor) as a primary service.

Then, the method continues at step 1345 with the processor 604 performing a test to determine if an optional service available in the same service window as a primary service may be added to the service bundle. Upon a determination at step 1345 by the processor 604 an optional service available in the same service window as a primary service may be added to the service bundle, the method continues at step 1350 with the processor 604 adding to the service bundle an optional service available within the same service window as a primary service.

Upon a determination at step 1345 by the processor 604 no optional service available in the same service window as a primary service may be added to the service bundle, the method continues at step 1355 with the processor 604 determining if performing bundled services in another optional service window (that is, a service window different from, or alternative to, the primary service window) would improve resource utilization. The resource utilization data evaluated by the processor 604 at step 1355 may include facility, equipment, or medical professional cost per unit time, percent idle time, or percent active time. The processor 604 may determine if resource utilization may be improved based on comparing calculated projected utilization of one or more resource based on the resource utilization data for more than one service window. The processor 604 may determine the relative cost to provide service in various service windows, to facilitate offering a discount determined by the processor 604 as a function of relative resource utilization between the service windows.

Then the method continues at step 1360 with the processor 604 performing a test to determine if offering service in an alternative service window would improve resource utilization, based on the evaluation of resource utilization in optional service windows performed by the processor 604 at step 1355. Upon a determination by the processor 604 at step 1360 offering service in an alternative service window would improve resource utilization, the method continues at step 1365 with the processor 604 adding an optional service window to the service bundle.

Upon a determination by the processor 604 at step 1360 offering service in an alternative service window would not improve resource utilization, the method continues at step 1370 with the processor 604 adding a prepayment discount determined as a function of relative service window resource utilization to the service bundle offer. In various embodiments, the method may repeat. In some designs, the method may end.

FIG. 14 is a process flow illustrative of an example aspect of patient lifecycle event triggered shopping cart provisioning design. The method depicted in FIG. 14 is given from the perspective of an exemplary patient lifecycle event triggered shopping cart provisioning engine (SCPE) implemented via processor-executable program instructions executing on the SCPE processor 604, depicted in FIG. 5. In various embodiments, the processor 604 implementing the process 1400 may be configured in an exemplary system 100 as described herein with reference to any of FIGS. 1, 6, and 9. For example, the depicted process may execute as processor executable program instructions on processor 604 configured in the application server 116, depicted in FIGS. 1, 6, and 9. In various embodiments, the method depicted in FIG. 14 may also be understood as from the perspective of processor-executable program instructions executing on a mobile device operably coupled with the network 150, depicted at least in FIGS. 1, 6, and 9. In the illustrated embodiment, the SCPE executes as program instructions on the processor 604, depicted in FIG. 5. In some embodiments, the SCPE may execute as a cloud service communicatively and operatively coupled with system services, hardware resources, or software elements local to and/or external to the SCPE processor 604. The depicted method 1400 begins at step 1405 with the processor 604 constructing a shopping cart based on the service bundle offer predetermined by the processor 604 executing the process 1300, depicted by FIG. 13.

Then, the method continues at step 1410 with the processor 604 presenting the shopping cart of bundled services to a patient as a function of service window (for example, a service window may include location, facility, time slot, doctor, or other variables) and a prepayment discount. The shopping cart of bundled services may be presented to the patient in an email, text message, mobile app, web page, chat window, or automated phone call. Various designs may enable the patient to select from among the offered services presented in the shopping cart. In an illustrative example, the shopping cart may offer a choice of service window with some services. For example, given an offered service such as a particular medical procedure, a service window choice presented to the patient with the medical procedure may include a choice of location, facility, time slot, doctor, or other optional procedures available within the service window. In some cases, more than one service window may be presented to a patient for selection. The service window choice may include a prepayment discount. More than one prepayment discount amount or prepayment discount percentage may be offered to a patient. The prepayment discount may vary as a function of the service window. The prepayment discount may be determined as a function of medical practice resource utilization, medical practice cost per unit time to provide a service in the service window, or medical professional availability during the service window. The prepayment discount may be a prepayment discount valid for prepayment before a predetermined date.

Then, the method continues at step 1415 with the processor 604 receiving an indication of patient service selection from the shopping cart of bundled services presented to the patient by the processor 604 at step 1410. The indication of patient service selection may be an indication the patient did not select an offered service after a predetermined time. The indication of patient service selection may be an indication the patient rejected the offered services.

Then, the method continues at step 1420 with the processor 604 performing a test to determine if the patient selected a service. Upon a determination by the processor 604 at step 1420 the patient did not select a service, the method continues at step 1425 with the processor 604 optionally adjusting the prepayment discount, and the method continues at step 1405 with the processor 604 constructing a shopping cart based on a service bundle offer.

Upon a determination by the processor 604 at step 1420 the patient selected a service, the method continues at step 1430 with the processor 604 applying the prepayment discount to the selected services, and the method continues at step 1435 with the processor 604 accepting payment. In various embodiments, the method may repeat. In some designs, the method may end.

Although various embodiments have been described with reference to the Drawings, other embodiments are possible.

In an aspect, an apparatus may comprise a processor; and a memory configured to be operably coupled to the processor, wherein the memory comprises encoded processor executable program instructions and data, wherein said instructions and data jointly program and configure the processor and wherein the instructions when executed by the processor cause the processor to perform operations comprising: receiving payment for a bundled set of a plurality of healthcare services comprising at least one dental service to be provided individually by a plurality of respective providers, wherein the received payment is pre-paid in an amount of a bundle price based on a location at which at least one healthcare service of the bundled set of healthcare services will be provided; and in response to receiving the payment, generating a purchase data record identified by a unique confirmation number selectively redeemable by a user to receive each healthcare service of the plurality of healthcare services individually.

The operations performed by the processor may further comprise storing the purchase data record and the unique confirmation number in the memory.

The operations performed by the processor may further comprise sending the unique confirmation number to the user.

The received payment may comprise real currency.

The received payment may comprise virtual funds.

The received virtual funds payment may further comprise promotional credit.

The operations performed by the processor may further comprise creating a virtual funds account for the user.

The received payment may be received from the virtual funds account created for the user.

The operations performed by the processor may further comprise disbursing payment to at least one of the plurality of respective providers.

The at least one of the plurality of respective providers to which payment is disbursed may further comprise at least one of a physician, a dentist, an orthodontist, a periodontist, an oral surgeon, a radiologist, an anesthesiologist, a dental hygienist, a practice group, a hospital or an insurer.

The disbursed payment may comprise real currency.

The disbursed payment may comprise virtual funds.

The disbursed payment may comprise a plurality of payments allocated from the received payment, wherein the plurality of payments may be disbursed to each of the plurality of respective providers.

The user may have a health insurance policy having a health insurance deductible and wherein the operations performed by the processor may further comprise applying an amount of the received payment to the health insurance deductible.

The amount of the received payment applied to the health insurance deductible may be determined by the processor as a function of the health insurance policy.

The operations performed by the processor may further comprise setting the bundle price based on the health insurance deductible.

The purchase data record may persist in a data store operably coupled with the processor and wherein the purchase data record may be redeemable until each of the plurality of healthcare services in the bundled set is redeemed.

The operations performed by the processor may further comprise: presenting to the user a plurality of healthcare services comprising at least one bundled set of the plurality of healthcare services to be performed separately by the plurality of respective providers; and receiving an indication of at least one bundled set of healthcare services selected by the user, wherein the bundle price may be further determined by the processor based on a time at which at least one of the plurality of services will be provided.

The bundle price may be a real currency price.

The bundle price may be a virtual funds price.

The bundle price may be an undiscounted price.

The bundle price may be a discounted price.

The purchase data record may further comprise a distinct redemption status for each individual healthcare service of the bundled set of healthcare services, and wherein the operations performed by the processor may further comprise setting each individual redemption status in the purchase data record to indicate the purchase has not been redeemed for each individual healthcare service of the bundled set of healthcare services.

The operations performed by the processor may further comprise receiving the unique confirmation number with a request for redemption of at least one healthcare service and using the purchase data record to selectively determine the redemption status of the at least one healthcare service.

The operations performed by the processor may further comprise updating the redemption status of the purchase data record to indicate redemption of at least one of the plurality of healthcare services.

The purchase data record may further comprise a transaction information record of the bundled set of healthcare services, and wherein updating the redemption status may further comprise updating in a data store operably coupled with the processor the transaction information record of the bundled set of healthcare services.

The at least one bundled set may further comprise a drug.

The at least one bundled set of healthcare services may further comprise a primary service and a secondary service associated with the primary service, and wherein the received payment may further comprise payment for the secondary service.

The purchase data record may be a voucher.

The voucher may be selectively redeemable for each healthcare service individually.

The at least one dental service may further comprise cleaning.

The at least one dental service may further comprise examination.

The at least one dental service may further comprise extraction.

The at least one dental service may further comprise restoration.

The at least one dental service may further comprise imaging.

The bundled set of the plurality of healthcare services may further comprise at least one dental service determined by the processor in response to a patient lifecycle event detected as a function of updated dental data received in an Electronic Health Record (EHR).

In an aspect, an apparatus may comprise: a processor; and a memory configured to be operably coupled to the processor, wherein the memory comprises encoded processor executable program instructions and data, wherein said instructions and data jointly program and configure the processor and wherein the instructions when executed by the processor cause the processor to perform operations comprising: receiving payment for a bundled set of a plurality of healthcare services comprising at least one veterinary service to be provided individually by a plurality of respective providers, wherein the received payment is pre-paid in an amount of a bundle price based on a location at which at least one healthcare service of the bundled set of healthcare services will be provided; and in response to receiving the payment, generating a purchase data record identified by a unique confirmation number selectively redeemable by a user to receive each healthcare service of the plurality of healthcare services individually.

The operations performed by the processor may further comprise storing the purchase data record and the unique confirmation number in the memory.

The operations performed by the processor may further comprise sending the unique confirmation number to the user.

The received payment may comprise real currency.

The received payment may comprise virtual funds.

The received virtual funds payment may further comprise promotional credit.

The operations performed by the processor may further comprise creating a virtual funds account for the user.

The received payment may be received from the virtual funds account created for the user.

The operations performed by the processor may further comprise disbursing payment to at least one of the plurality of respective providers.

The at least one of the plurality of respective providers to which payment is disbursed may further comprise at least one of a physician, a veterinarian, an anesthesiologist, a radiologist, a veterinary technician, a practice group, a hospital or an insurer.

The disbursed payment may comprise real currency.

The disbursed payment may comprise virtual funds.

The disbursed payment may comprise a plurality of payments allocated from the received payment, wherein the plurality of payments may be disbursed to each of the plurality of respective providers.

The user may have a health insurance policy having a health insurance deductible and wherein the operations performed by the processor may further comprise applying an amount of the received payment to the health insurance deductible.

The amount of the received payment applied to the health insurance deductible may be determined by the processor as a function of the health insurance policy.

The operations performed by the processor may further comprise setting the bundle price based on the health insurance deductible.

The purchase data record may persist in a data store operably coupled with the processor and wherein the purchase data record may be redeemable until each of the plurality of healthcare services in the bundled set is redeemed.

The operations performed by the processor may further comprise: presenting to the user a plurality of healthcare services comprising at least one bundled set of the plurality of healthcare services to be performed separately by the plurality of respective providers; and receiving an indication of at least one bundled set of healthcare services selected by the user, wherein the bundle price may be further determined by the processor based on a time at which at least one of the plurality of services will be provided.

The bundle price may be a real currency price.

The bundle price may be a virtual funds price.

The bundle price may be an undiscounted price.

The bundle price may be a discounted price.

The purchase data record may further comprise a distinct redemption status for each individual healthcare service of the bundled set of healthcare services, and wherein the operations performed by the processor may further comprise setting each individual redemption status in the purchase data record to indicate the purchase has not been redeemed for each individual healthcare service of the bundled set of healthcare services.

The operations performed by the processor may further comprise receiving the unique confirmation number with a request for redemption of at least one healthcare service and using the purchase data record to selectively determine the redemption status of the at least one healthcare service.

The operations performed by the processor may further comprise updating the redemption status of the purchase data record to indicate redemption of at least one of the plurality of healthcare services.

The purchase data record may further comprise a transaction information record of the bundled set of healthcare services, and wherein updating the redemption status may further comprise updating in a data store operably coupled with the processor the transaction information record of the bundled set of healthcare services.

The at least one bundled set may further comprise a drug.

The at least one bundled set of healthcare services may further comprise a primary service and a secondary service associated with the primary service, and wherein the received payment may further comprise payment for the secondary service.

The purchase data record may be a voucher.

The voucher may be selectively redeemable for each healthcare service individually.

The at least one veterinary service further may comprise a dental service.

The at least one veterinary service may further comprise a vaccination service.

The at least one veterinary service may further comprise prescribing a drug.

The at least one veterinary service may further comprise a service related to surgery.

The at least one veterinary service may further comprise room and board.

The operations performed by the processor may further comprise associating an identification code transmitted by a transponder in a non-human animal patient with the unique confirmation number using the purchase data record.

The operations performed by the processor may further comprise receiving the identification code.

The bundled set of healthcare services may further comprise at least one service related to room and board pre-paid for the non-human animal patient.

The bundled set of healthcare services may further comprise an additional pre-paid amount of funds redeemable to a person who found the non-human animal patient.

The bundled set of the plurality of healthcare services may further comprise at least one veterinary service determined by the processor in response to a patient lifecycle event detected as a function of updated veterinary medical data received in an Electronic Health Record (EHR).

For example, at least one service of a bundled set of healthcare services may comprise a dental service. An implementation in accordance with the present disclosure may comprise processor executable program instructions and data configured to cause the processor 604 to perform operations comprising presenting users a selection of at least one bundled set of healthcare services comprising a dental service, wherein the healthcare services are provided discretely and/or individually by a plurality of respective providers, determining a bundle price for the bundled set of healthcare services, receiving payment for the user selected bundled set, generating a purchase data record selectively redeemable by the user to receive each of the bundled healthcare services in the bundled set, transmitting a unique confirmation number generated for the purchase data record to track the redemption status of the purchase data record, disbursing payment allocated from the received payment to the plurality of respective providers and updating the redemption status of the purchase data record as each of the plurality of services of the bundled set are redeemed. The bundle price for a bundled set of services comprising a dental service may be based on the user's health insurance deductible as well as the location and/or time at which the bundled set of services will be provided. The purchase data record may be a voucher. The dental service may be a dental service for a human patient. The dental service may be a dental service for a non-human patient.

The dental service may comprise a service related to tooth care. The dental service may comprise a service related to mouth care. The dental service related to tooth care may comprise, for example, cleaning, examination, treatment, filling, extraction, or restoration. An implementation in accordance with the present disclosure may create and maintain a persistent selectively redeemable purchase data record for a bundled set of healthcare services comprising one or more dental service.

The dental service related to mouth care may be a screening for a disease involving the patient's oral cavity. The disease involving the patient's oral cavity may be, for example, cancer. A dental service provider may be a dentist. The dentist may be, for example, a general dentist, an orthodontist, a periodontist, or an oral surgeon. A dental service provider may be a dental hygienist. A dental service may further comprise one or more anesthesia service. The anesthesia service may be provided by the dentist. The anesthesia service may be provided by an anesthesiologist. A dental service may further comprise one or more service provided by a radiologist.

A dental service comprising cleaning may further comprise periodic or regularly scheduled cleaning of a patient's teeth. A dental cleaning service may be prescribed because of a dental examination. A dental cleaning service may comprise one cleaning procedure. A dental cleaning service may comprise more than one cleaning procedure. For example, a dental cleaning service may be a single cleaning procedure encompassing cleaning all the teeth in a patient's mouth in one procedure or visit. A dental cleaning service may comprise a set of individual cleaning procedures performed at different times wherein each individual cleaning procedure is a component of the dental cleaning service. For example, multiple individual cleaning procedure components of a dental cleaning service may each be directed to clean different groups of a patient's teeth. Some dental cleaning services may partition a patient's teeth into groups and each group of teeth may be cleaned during a separate dental cleaning procedure scheduled on a distinct day.

A dental service provided by the dentist may comprise examination of a patient's teeth. Examination of the patient's teeth may further comprise the dentist determining the condition of individual teeth, based on the dentist manually probing individual teeth. The dentist may record in an Electronic Health Record (EHR) an individual condition of one or more patient tooth determined by the dentist's examination. The EHR comprising the dentist's determination of the patient's tooth condition may be stored by the processor 604 in one or more data store. The processor 604 may compare the EHR comprising updated dental data from the dentist's determination of the patient's tooth condition with archived patient tooth condition data. The processor 604 may determine a patient lifecycle event occurred based on the comparison, as disclosed, for example, with reference to FIGS. 11-14. In response to determining a patient lifecycle event occurred, the processor 604 may further determine additional services or bundled sets of services to be presented to the patient as disclosed, for example, with reference to FIGS. 11-14. For example, the processor 604 may determine additional tooth treatment services to be offered to the patient, based on the updated data.

Examination of the patient's mouth may further comprise examination of the patient's gums. Examination of the patient's gums may further comprise the dentist determining the condition of the patient's gumline in proximity to one or more tooth. For example, the dentist may determine the condition of the patient's gumline based on the dentist manually measuring the depth of gum pockets along the patient's gumline. The dentist may record in an Electronic Health Record (EHR) an individual condition or depth of one or more gum pocket along a patient's gumline, based on the dentist's examination. The EHR comprising the dentist's determination of the patient's gum pocket depth or gumline condition may be stored by the processor 604 in one or more data store. The processor 604 may compare the EHR comprising updated dental data from the dentist's determination of the patient's gum pocket depth or gumline condition with archived patient gum pocket depth or gumline condition data. The processor 604 may determine a patient lifecycle event occurred based on the comparison, as disclosed, for example, with reference to FIGS. 11-14. In response to determining a patient lifecycle event occurred, the processor 604 may further determine additional services or bundled sets of services to be presented to the patient as disclosed, for example, with reference to FIGS. 11-14. For example, the processor 604 may determine additional periodontal services to be offered to the patient, based on the updated data.

Examination of the patient's teeth may further comprise a diagnostic imaging procedure. The diagnostic imaging procedure may further comprise one or more radiographic imaging procedure. The radiographic imaging procedure may further comprise, for example, an X-ray, Computed Tomography (CT), Cone-beam Computed Tomography (CBCT), or Magnetic Resonance Imaging (MM) procedure. The diagnostic imaging procedure may be performed by the dentist. The diagnostic imaging procedure may be performed by an imaging service provider separate from the dentist. The diagnostic imaging procedure may result in one or more diagnostic image. The one or more diagnostic image may be evaluated by the dentist. One or more diagnostic image may be evaluated by a dental radiologist. The dentist or dental radiologist may determine the condition of one or more of the patient's teeth based on evaluation of the one or more diagnostic image. The dentist or dental radiologist may record in an EHR an individual condition of one or more patient tooth determined based on an evaluation of the one or more diagnostic image. The EHR comprising the individual tooth condition determined using the one or more diagnostic image may be stored by the processor 604 in one or more data store. The processor 604 may compare the EHR comprising updated dental data from the determination of the individual tooth condition with archived patient tooth condition data. The processor 604 may determine a patient lifecycle event occurred based on the comparison, as disclosed, for example, with reference to FIGS. 11-14. In response to determining a patient lifecycle event occurred, the processor 604 may further determine additional services or bundled sets of services to be presented to the patient as disclosed, for example, with reference to FIGS. 11-14. For example, the processor 604 may determine additional tooth treatment services to be offered to the patient, based on the updated data.

A dental service comprising treatment may further comprise drilling, filling, extraction, or restoration, of one or more tooth. A dental service may further comprise one or more service provided by a dental lab. A dental lab service may include crafting or manufacturing a dental prosthetic device or dental appliance. Dental prosthetic devices may include an implant, crown, cap, bridge, denture, or other device used to restore, replace, or enhance appearance or function of a dental patient's teeth. A dentist may place, install, or set the dental prosthetic device or dental appliance in a patient's mouth. A dental service may further comprise a dentist placing, installing, or setting a dental prosthetic device or dental appliance in a patient's mouth. A dental service may further comprise installing or adjusting braces. In illustrative examples a bundled set of services may comprise one or more service related to planning, visualization of abnormal teeth, evaluation of the jaws and face, cleft palate assessment, diagnosis of dental caries (cavities), endodontic (root canal) diagnosis, or diagnosis and/or treatment of dental trauma.

At least one service of a bundled set of healthcare services may comprise a veterinary service. A veterinary service may further comprise a dental service in accordance with the present disclosure. An implementation in accordance with the present disclosure may comprise processor executable program instructions and data configured to cause the processor 604 to perform operations comprising presenting users a selection of at least one bundled set of healthcare services comprising a veterinary service, wherein the healthcare services are provided discretely and/or individually by a plurality of respective providers, determining a bundle price for the bundled set of healthcare services, receiving payment for the user selected bundled set, generating a purchase data record selectively redeemable by the user to receive each of the bundled healthcare services in the bundled set, transmitting a unique confirmation number generated for the purchase data record to track the redemption status of the purchase data record, disbursing payment allocated from the received payment to the plurality of respective providers and updating the redemption status of the purchase data record as each of the plurality of services of the bundled set are redeemed. The bundle price for a bundled set of services comprising a veterinary service may be based on the user's health insurance deductible as well as the location and/or time at which the bundled set of services will be provided. The purchase data record may be a voucher.

The veterinary service may comprise a service related to healthcare for a non-human animal patient. The non-human animal patient may be a pet. The veterinary service may be provided by a veterinarian. The veterinary service may be provided by a veterinary technician. The veterinary service may comprise a service related to vaccination. The veterinary service may comprise a service related to a patient's skeletal system. The veterinary service may comprise a service related to a patient's skin or fur. The veterinary service may comprise one or more drug. The one or more drug may further comprise a prescription drug. The veterinary service may comprise a service related to a patient's external appendages. The patient's external appendages may further comprise fins, flippers, beaks, trunks, tails, legs, arms, or the like. The veterinary service may comprise a service related to internal medicine. The veterinary service related to internal medicine may comprise a service related to a patient's blood. The veterinary service related to internal medicine may comprise a service related to a condition that may result due to a parasite. The veterinary service related to internal medicine may comprise a service related to a condition that may result due to a poison. The veterinary service may comprise a service related to surgery. The veterinary service may comprise an anesthesia service. The anesthesia service may be provided by the veterinarian. The anesthesia service may be provided by an anesthesiologist. The veterinary service may comprise a service related to trimming claws. The veterinary service may comprise a service related to cleaning teeth. The veterinary service related to cleaning teeth may comprise, for example, cleaning, examination, treatment, filling, extraction, or restoration. The veterinary service may comprise a service related to a condition that may result due to the non-human animal patient or pet being lost or separated from their human family. An implementation in accordance with the present disclosure may create and maintain a persistent selectively redeemable purchase data record for a bundled set of healthcare services comprising one or more veterinary service.

In some cases, a veterinarian may record in an Electronic Health Record (EHR) a medical condition or diagnostic result. The medical condition or diagnostic result recorded in the EHR may be a result of the veterinarian providing a healthcare service to a patient. The medical condition or diagnostic result recorded in the EHR may be a medical condition or diagnostic result determined by the veterinarian during examination of the patient. The EHR comprising the medical condition or diagnostic result determined by the veterinarian may be stored by the processor 604 in one or more data store. The processor 604 may compare the EHR comprising updated veterinary medical data from the veterinarian's determination of the patient's condition with archived patient condition data. The processor 604 may determine a patient lifecycle event occurred based on the comparison, as disclosed, for example, with reference to FIGS. 11-14. In response to determining a patient lifecycle event occurred, the processor 604 may further determine additional veterinary services or bundled sets of services to be presented to the patient as disclosed, for example, with reference to FIGS. 11-14. For example, the processor 604 may determine additional treatment services to be offered to the patient, based on the updated data.

In an implementation in accordance with the present disclosure, a veterinary service may comprise providing food, water, medical care, transportation, or a safe place to sleep for the non-human animal patient. Such services may be known as room and board services. In some cases, the veterinary services comprising room and board may be provided to a patient as a result of the non-human animal patient or pet being lost or separated from their human family. An implementation in accordance with the present disclosure may be configured to permit pre-paid purchase of a bundled set of healthcare services comprising veterinary services, wherein the bundled set of healthcare services further comprises providing food, water, medical care, transportation, or a safe place to sleep for the non-human animal patient. An implementation in accordance with the present disclosure may be configured with processor executable program instructions to cause the processor 604 to perform operations comprising associating an identification code transmitted by a transponder in the non-human animal patient with the unique confirmation number generated by the processor 604 that identifies the bundled set of healthcare services using the purchase data record. A copy of the identification code may be encoded by the purchase data record to permit the processor 604 to associate the identification code with the unique confirmation number that identifies the bundled set of services. The copy of the identification code may be stored in or with the purchase data record during a registration step. The copy of the identification code may be stored in or with the purchase data record when the bundled set of services is purchased. The identification code transmitted by the transponder may be a code identifying an animal. The transponder may be a transponder configured for radio frequency identification (RFID) of animals in accordance with ISO 11784, ISO 11785, or ISO 14223 standards, or the like. The transponder may be any type of transponder as may be known by one of ordinary skill in the field of art relevant to radio frequency identification. The transponder may be known as a pet microchip. In an illustrative example, a concerned person finding a lost animal may take the lost animal to an animal shelter or veterinarian, permitting the animal to be scanned for the identification code transmitted by the transponder when scanned. The veterinarian or animal shelter may be equipped with a mobile device configured to receive the identification code transmitted by the transponder when the transponder is scanned. The mobile device may send the received identification code to a server implementation in accordance with the present disclosure. In this example, the server implementation in accordance with the present disclosure may receive the identification code using the processor 604, and associate the received identification code with the unique confirmation number encoded by the purchase data record, wherein the unique confirmation number was generated by the processor 604 to identify the bundled set of healthcare services, using the processor 604 and the purchase data record. The server implementation in accordance with the present disclosure may send an indication the bundled set of healthcare services comprises at least one service such as providing food, water, medical care, transportation, or a safe place to sleep for the non-human animal patient that was implanted with the transponder that transmitted the identification code. The server implementation in accordance with the present disclosure may send the unique confirmation number identifying the bundled set of healthcare services to the animal shelter or veterinarian, permitting redemption of one or more services of the bundled set of services using the purchase data record selectively redeemable to receive each of the bundled healthcare services in the bundled set. In some examples the bundled set of services may further comprise an additional prepaid amount of funds redeemable by the person who found the pet, and who transmitted the pet's identifying code to the server.

In the Summary above, in this Detailed Description, the Claims below, the content of each of the applications incorporated by reference herein and in the accompanying drawings, reference is made to features of various embodiments of the invention. It is to be understood that the disclosure of embodiments of the invention in this specification includes all possible combinations of such features. For example, where a particular feature is disclosed in the context of a particular aspect or embodiment of the invention, or a particular claim, that feature can also be used—to the extent possible—in combination with and/or in the context of other aspects and embodiments of the invention, and in the invention generally.

Therefore, it is intended that the invention not be limited to the particular embodiments disclosed as the best mode contemplated for carrying out this invention, but that the invention will include all embodiments falling within the scope of the present application as set forth in the following claims, wherein reference to an element in the singular, such as by use of the article "a" or "an" is not intended to mean "one and only one" unless specifically so stated, but rather "one or more." Moreover, no claim element is to be construed under the provisions of 35 U.S.C. § 112(f), or 35 U.S.C. § 112, sixth paragraph (pre-AIA), unless the element is expressly recited using the phrase "means for" or "step for." These following claims should be construed to maintain the proper protection for the present invention.

What is claimed is:

1. A method comprising:
   receiving an electronic message comprising user selection of a plurality of healthcare services to be performed separately by a plurality of providers, wherein the selected plurality of healthcare services comprises at least one selectively redeemable healthcare service to be provided for a patient via a telehealth visit comprising a face-to-face video conversation with at least one provider of the plurality of providers, using a processor; and
   in response to receiving the electronic message comprising the selection of the plurality of healthcare services,
      generating an electronic health record (EHR) comprising a purchase data record identified by and with a unique confirmation number, using the processor;
      presetting an initial individual redemption status in the purchase data record for each selectively redeemable healthcare service of the selected plurality of healthcare services as unredeemed, using the processor; and
      providing a user access to the purchase data record to receive each selectively redeemable healthcare service of the selected plurality of healthcare services, using the processor.

2. The method of claim 1, wherein the selected plurality of healthcare services comprises at least one healthcare service to be provided for a patient via an in-person visit with at least one provider of the plurality of providers.

3. The method of claim 1, wherein the selected plurality of services comprises at least one healthcare service to be provided remotely.

4. The method of claim 1, wherein the selected plurality of services comprises at least one healthcare service to be provided for a patient at a patient location remote from a provider location of at least one provider of the plurality of providers.

5. The method of claim 1, wherein the telehealth visit further comprises at least one of: video, audio, a telephone call, text messaging, or chat messaging.

6. The method of claim 1, wherein the telehealth visit further comprises a new prescription or a prescription refill recommended by the at least one provider.

7. The method of claim 1, wherein the telehealth visit further comprises referral by the at least one provider for a lab test, imaging, or a specialist.

8. The method of claim 1, wherein the telehealth visit further comprises urgent care.

9. The method of claim 1, wherein the telehealth visit further comprises symptom assessment by the at least one provider.

10. The method of claim 1, wherein the selected plurality of healthcare services further comprises providing at least one drug.

11. The method of claim 1, wherein the selected plurality of healthcare services further comprises at least one lab test.

12. The method of claim 1, wherein the selected plurality of healthcare services further comprises at least one imaging procedure.

13. The method of claim 1, wherein the selected plurality of healthcare services further comprises at least one surgical procedure.

14. The method of claim 1, wherein in response to receiving the electronic message comprising user selection of the plurality of healthcare services, the method further comprises:
   storing the EHR in a memory operably coupled with the processor, using the processor; and
   sending the EHR to at least one provider of the plurality of providers, using the processor.

15. The method of claim 1, wherein the method further comprises sending the unique confirmation number to the user, using the processor.

16. The method of claim 1, wherein the purchase data record is the EHR.

17. The method of claim 1, wherein the purchase data record is selectively redeemable for each healthcare service individually, using the processor.

18. The method of claim 1, wherein the purchase data record persists in a data store operably coupled with the processor and wherein the purchase data record is redeemable using the processor until each of the plurality of healthcare services in the selected plurality of services is redeemed.

19. The method of claim 1, wherein the method further comprises receiving payment for the selected plurality of healthcare services, using the processor.

20. The method of claim 19, wherein the selected plurality of healthcare services further comprises at least one healthcare service selectively redeemable for a predetermined period of time, using the processor.

21. The method of claim 19, wherein the payment further comprises financing.

22. The method of claim 1, wherein the method further comprises setting the individual redemption status in the purchase data record for each selectively redeemable healthcare service of the selected plurality of services as unredeemed, using the processor.

23. The method of claim 1, wherein the method further comprises receiving a payment for a price determined as a function of a location where the at least one selectively redeemable healthcare service of the selected plurality of healthcare services will be provided, using the processor.

24. The method of claim 23, wherein the method further comprises disbursing at least one payment allocated from the received payment to at least one of the plurality of providers, wherein the at least one disbursed payment comprises virtual money, using the processor.

25. The method of claim 24, wherein the at least one of the plurality of providers to whom payment is disbursed comprises at least one of a physician, a dentist, an orthodontist, a periodontist, an oral surgeon, a radiologist, an anesthesiologist, a dental hygienist, a physician assistant, a nurse, a therapist, a counselor, a psychologist, a social worker, a practice group, a hospital, a facility or an insurer.

26. The method of claim 24, wherein the disbursed payment comprises a plurality of payments allocated among at least two providers of the plurality of providers, using the processor.

27. The method of claim 1, wherein the method further comprises providing an application server using the processor wherein the application server is accessible to a plurality of client systems communicatively coupled to the application server, wherein the application server implements a web application, and wherein each client system implements a client application configured to provide a web-based user interface for accessing a network service provided by the application server via the web application.

* * * * *